United States Patent
Wang et al.

(10) Patent No.: US 9,745,266 B2
(45) Date of Patent: Aug. 29, 2017

(54) INDOLINE ALKALOID COMPOUNDS

(71) Applicants: THE REGENTS OF THE UNIVERSITY OF COLORADO, A BODY CORPORATE, Denver, CO (US); Xiang Wang, Superior, CO (US); Jessica Podoll, Boulder, CO (US); Le Chang, Boulder, CO (US)

(72) Inventors: Xiang Wang, Superior, CO (US); Jessica Podoll, Boulder, CO (US); Le Chang, Boulder, CO (US)

(73) Assignee: The Regents of the University of Colorado, Denver, CO (US)

( * ) Notice: Subject to any disclaimer, the term of this patent is extended or adjusted under 35 U.S.C. 154(b) by 0 days.

(21) Appl. No.: 14/781,639

(22) PCT Filed: Apr. 1, 2014

(86) PCT No.: PCT/US2014/032585
§ 371 (c)(1),
(2) Date: Oct. 1, 2015

(87) PCT Pub. No.: WO2014/165548
PCT Pub. Date: Oct. 9, 2014

(65) Prior Publication Data
US 2016/0060219 A1    Mar. 3, 2016

Related U.S. Application Data

(60) Provisional application No. 61/807,071, filed on Apr. 1, 2013.

(51) Int. Cl.
| | | |
|---|---|---|
| C07D 209/86 | (2006.01) |
| C07D 209/88 | (2006.01) |
| A61K 31/403 | (2006.01) |
| A61K 45/06 | (2006.01) |
| A61K 31/404 | (2006.01) |
| A61K 31/407 | (2006.01) |
| A61K 31/424 | (2006.01) |
| A61K 31/43 | (2006.01) |
| A61K 31/437 | (2006.01) |
| A61K 31/454 | (2006.01) |
| A61K 31/475 | (2006.01) |
| A61K 31/546 | (2006.01) |

(52) U.S. Cl.
CPC .......... *C07D 209/86* (2013.01); *A61K 31/403* (2013.01); *A61K 31/404* (2013.01); *A61K 31/407* (2013.01); *A61K 31/424* (2013.01); *A61K 31/43* (2013.01); *A61K 31/437* (2013.01); *A61K 31/454* (2013.01); *A61K 31/475* (2013.01); *A61K 31/546* (2013.01); *A61K 45/06* (2013.01)

(58) Field of Classification Search
CPC .. C07D 209/86; C07D 209/88; A61K 31/403; A61K 45/06
USPC ......... 548/439, 444, 443, 442, 441; 514/411
See application file for complete search history.

(56) References Cited

U.S. PATENT DOCUMENTS

| | | |
|---|---|---|
| 2010/0069441 A1 | 3/2010 | Gordeev et al. |
| 2011/0294723 A1 | 12/2011 | Wadman |
| 2013/0123225 A1 | 5/2013 | Melander et al. |

FOREIGN PATENT DOCUMENTS

WO    2012006276 A1    1/2012

OTHER PUBLICATIONS

Mori, M., M. Nakanishi, D. Kajishima, and Y. Sata "A New and General Synthetic Pathway to Strychnos Indole Alkaloids: Total Syntheses of (-)-Dehydrotubifoline and (-)-Tubifoline by Palladium-catalyzed Asymmetric Allylic Substitution" Org. Lett. (2001), 3 (12), pp. 1913-1916.*
Yongxiang Liu; Wenqing Xu, and Xiang Wang: Gold(I)-Catalyzed Tandem Cyclization Approach to Tetracyclic Indolines. Organic Letters, vol. 12, No. 7, pp. 1448-1451. 2010.

* cited by examiner

*Primary Examiner* — Matthew Coughlin
*Assistant Examiner* — Sagar Patel
(74) *Attorney, Agent, or Firm* — Don D. Cha; Hamilton DeSanctis & Cha, LLP.

(57) ABSTRACT

The present invention relates to indoline alkaloid compounds. In particular, indoline alkaloid compounds of the invention have antibacterial activity and/or are capable of resensitizing the susceptibility of methicillin-resistant *S. aureus* to a β-lactam antibiotic. The present invention also relates to a method for producing and using the same.

9 Claims, 8 Drawing Sheets a.

b.

a.

b.

INDOLINE ALKALOID COMPOUNDS

CROSS-REFERENCE TO RELATED APPLICATIONS

This application claims the priority benefit of U.S. Provisional Application No. 61/807,071, filed Apr. 1, 2013, which is incorporated herein by reference in its entirety.

FIELD OF THE INVENTION

The present invention relates to indoline alkaloid compounds. In particular, indoline alkaloid compounds of the invention have antibacterial activity and/or are capable of re-sensitizing methicillin-resistant S. aureus to a β-lactam antibiotic. The present invention also relates to a method for producing and using the same.

BACKGROUND OF THE INVENTION

Antibiotics are one of the most important and widely used medicines. Their extensive use has led to the resistance development by their pathogenic bacterial targets. The emergence of multi-drug resistant bacteria has become a global public health threat. Serious infection of multi-drug resistant microorganisms often causes considerable patient mortality and modality. For example, more people died from methicillin-resistant Staphylococci aureus (MRSA) infection than those from HIV/AIDS, Parkinson's disease and homicide combined. The development of structural analogs of existing antibiotics had kept up with the emergence of new resistance until 20 years ago. Currently, there are not enough analogs in the antibiotic pipeline to combat imminent and future resistance emergence. In addition, the search for new structural classes of antibiotics has yielded only two new classes of antibacterials since 1960. The Pharmaceutical industry has devoted significant resources to high-throughput screening of large compound libraries against targets identified from genetic methods in recent years. However, these efforts have made limited progress.

Resistance-modifying agents (RMAs) are a highly favorable alternative. These target non-essential resistance conferring genes and can further expand the life span of antibiotics that are currently used in the clinics, which have already been optimized for toxicity and large-scale production. For example, clavulanic acid is a β-lactamase inhibitor. Its use in combination with amoxicillin restores the efficacy of amoxicillin against many β-lactamase producing bacteria.

Despite current efforts in identification and synthesis of RMAs, there is a continuing and urgent need for RMAs that can extend the usefulness of antibiotics for the treatment of drug resistant bacteria.

SUMMARY OF THE INVENTION

Some aspects of the invention provide a resistance-modifying agent ("RMA"). Without being bound by any theory, it is believed that RMAs target non-essential, resistance-conferring genes and restore antibiotic sensitivity of a bacteria. A notable advantage of RMAs is that they are capable of extending the market lifespan of known antibiotics that have already been optimized for large-scale production with well-studied toxicity profiles. One particular aspect of the invention provides an indoline alkaloid compound ("indoline alkaloid") that selectively re-sensitizes methicillin-resistant S. aureus to β-lactam antibiotics, such as oxacillin, amoxicillin/clavulanic acid, meropenem and cefazolin. Indoline alkaloids of the invention can be used in combination with β-lactam antibiotics to treat antibiotic resistant bacterial infections. Moreover, some of the indoline alkaloid compounds of the invention are effective antibiotics in and of themselves, e.g., compounds Of4 and Kf4 have antibacterial activity with MIC values of 32 μg/mL for both methicillin-sensitive S. aureus and methicillin-resistant S. aureus.

Thus, one particular aspect of the invention provides an indoline alkaloid compound that is capable of re-sensitizing methicillin-resistant S. aureus to a β-lactam antibiotic. In one particular embodiment, the indoline alkaloid is of the formula:

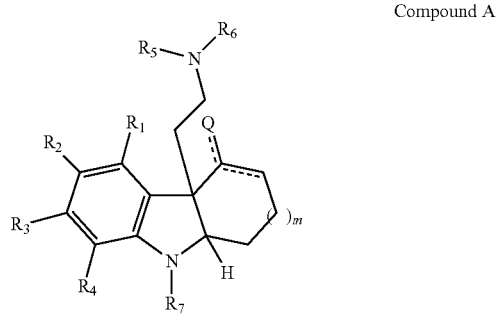

Compound A where each of m and n is independently 1 or 2; one of the dotted lines is a double bond, provided Q is $CH_2$ when the double bond is exocyclic, and Q is H when the double bond is endocyclic; each of $R_1$, $R_3$ and $R_4$ is independently hydrogen or halide, or $R_3$ and $R_4$ together with the carbon atoms to which they are attached form phenyl; $R_2$ is hydrogen, halide, alkyl, or alkoxide; $R_5$ is hydrogen, alkyl, $—S(O)_2\,Ar^1$ or $—COAr^1$; $R_6$ is hydrogen, $—S(O)_2Ar^2$, $—COAr^2$ or $—COR^8$; $R_7$ is hydrogen, alkyl, $—S(O)_2Ar^3$ or $—COAr^3$; $R^8$ is alkyl or haloalkyl; each of $Ar^1$ and $Ar^3$ is independently optionally substituted aryl; and $Ar^2$ is optionally substituted aryl or optionally substituted heteroaryl. In some embodiments, when $R_6$ is $—S(O)_2$-Ph-p-Cl and $R_2$ is Br, at least one of $R_1$, $R_3$, $R_4$, $R_5$ and $R_7$ is not hydrogen. The notation -Ph-p-Cl refers to para-chloro substituted phenyl.

In other embodiments, $R_1$ is hydrogen or Br; and/or $R_2$ is Br, Cl, F, alkyl (e.g., methyl), or alkoxy (e.g., methoxy); and/or $R_3$ is hydrogen or Br; and/or $R^4$ is hydrogen, Br, Cl or F; and/or $R_3$ and $R_4$ together with the carbon atoms to which they are attached form phenyl. The term "and/or" refers to in combination or alternatively, i.e., in combination or separately. Yet in other embodiments, $R^5$ is hydrogen and/or $R^7$ is hydrogen. In another embodiment, $R^6$ is $—S(O)_2\,Ar^2$. Yet in other embodiments, $R^8$ is perfluoroalkyl (e.g., trifluoromethyl) or alkyl (e.g., methyl). In some embodiments, $Ar^1$ and $Ar^3$ is independently para-substituted halophenyl; and/or $Ar^2$ is phenyl, para-substituted phenyl, or di-substituted phenyl, or heteroaryl. Within these embodiments, in some instances, $Ar^1$ and $Ar^3$ is independently para-chlorophenyl; and/or $Ar^2$ is phenyl, para-substituted halophenyl, para-substituted alkylphenyl, para-substituted cyanophenyl, para-substituted acetamidephenyl, 2,4- or 3,4-substituted dihalophenyl, or pyridyl.

In another embodiment, the indoline alkaloid is of the formula:

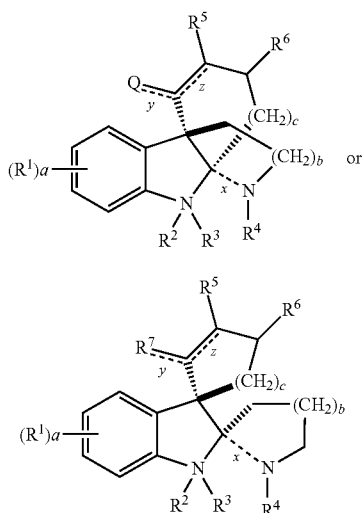

Compound I

Compound II where at most only one of the dotted lines y or z is a double bond (in some embodiments neither y or z is a double bond, yet in other embodiments y is a double bond, still in some embodiments, z is a double bond), provided Q is $CH_2$ when the double bond is exocyclic (i.e., y is a double bond), and Q is H when the double bond is endocyclic (i.e., z is a double bond); a is an integer from 0 to 4; each of b and c is independently 1 or 2; dotted bond x can optionally be absent in which case the nitrogen atom of the dotted bond x further comprises $R^a$, wherein $R^a$ is hydrogen or alkyl; $R^7$ is $CH_2$ or when the dotted double bond y is absent, $R^7$ is a hydrogen atom or $CH_3$; each of $R^1$ is independently halide, alkyl, or alkoxide, or when a is an integer of at least two, two of $R^1$'s together with the carbon atoms to which they are attached to can form an optionally substituted aryl group; $R^2$ is absent, hydrogen or alkyl; $R^3$ is hydrogen, alkyl, a nitrogen protecting group, (cycloalkyl)alkyl, (optionally substituted aryl) alkyl, alkenyl, or alkynyl; $R^4$ is hydrogen, alkyl, or a nitrogen protecting group; and $R^5$ and $R^6$ are hydrogen or together along with the carbon atoms to which they are attached to form an optionally substituted aryl group, provided that when $R^5$ and $R^6$ along with the carbon atoms to which they are attached to form an optionally substituted aryl group the dotted double bond z is absent. In some embodiments, a is 0, 1 or 2; and/or each of $R^1$ is independently selected from the group consisting of fluoro, methyl, bromo, chloro, or methoxy; and/or $R^2$ is absent. Yet in other embodiments, a is 2 and $R^1$'s together along with the carbon atoms to which they are attached to form an optionally substituted aryl group. Still in other embodiments, $R^3$ is selected from the group consisting of hydrogen, alkyl, (optionally substituted phenyl) methyl, alkynyl, alkenyl, (cyclohexyl)methyl, —C(=O)$R^b$, and —SO$_2$Ar$^1$, wherein $R^b$ is alkyl, haloalkyl, alkoxy, or optionally substituted phenyl, and Ar$^1$ is optionally substituted aryl; and/or c is 1 or 2. Still in other embodiments, $R^4$ is selected from the group consisting of hydrogen, alkyl, tosylate, —C(=O)$R^b$, and —SO$_2$Ar$^1$, wherein $R^b$ is alkyl, haloalkyl, alkoxy, alkenyl, or optionally substituted phenyl, and Ar$^1$ is optionally substituted aryl; and/or $R^5$ and $R^6$ together along with the carbon atoms to which they are attached to form an optionally substituted aryl group.

Another aspect of the invention provides an antibiotic composition comprising an indoline alkaloid compound disclosed herein. In some embodiments, the antibiotic composition further comprises a β-lactam antibiotic or a β-lactam antibiotic in combination with a β-lactamase inhibitor.

Yet another aspect of the invention provides a method for treating bacterial infection in a subject comprising administering to the subject in need of such a treatment a therapeutically effective amount of a β-lactam antibiotic and an indoline alkaloid compound disclosed herein.

Still other aspects of the invention provide methods for producing various compounds and/or intermediate compounds disclosed herein.

Some of the specific substituents for Compounds A, I, II, IA, and IB are disclosed in specific compounds disclosed herein. It should be noted that combinations of various groups described herein form other embodiments. In this manner, a variety of compounds are embodied within the present invention.

DETAILED DESCRIPTION OF THE INVENTION

Compounds of the Invention

Figure 1:
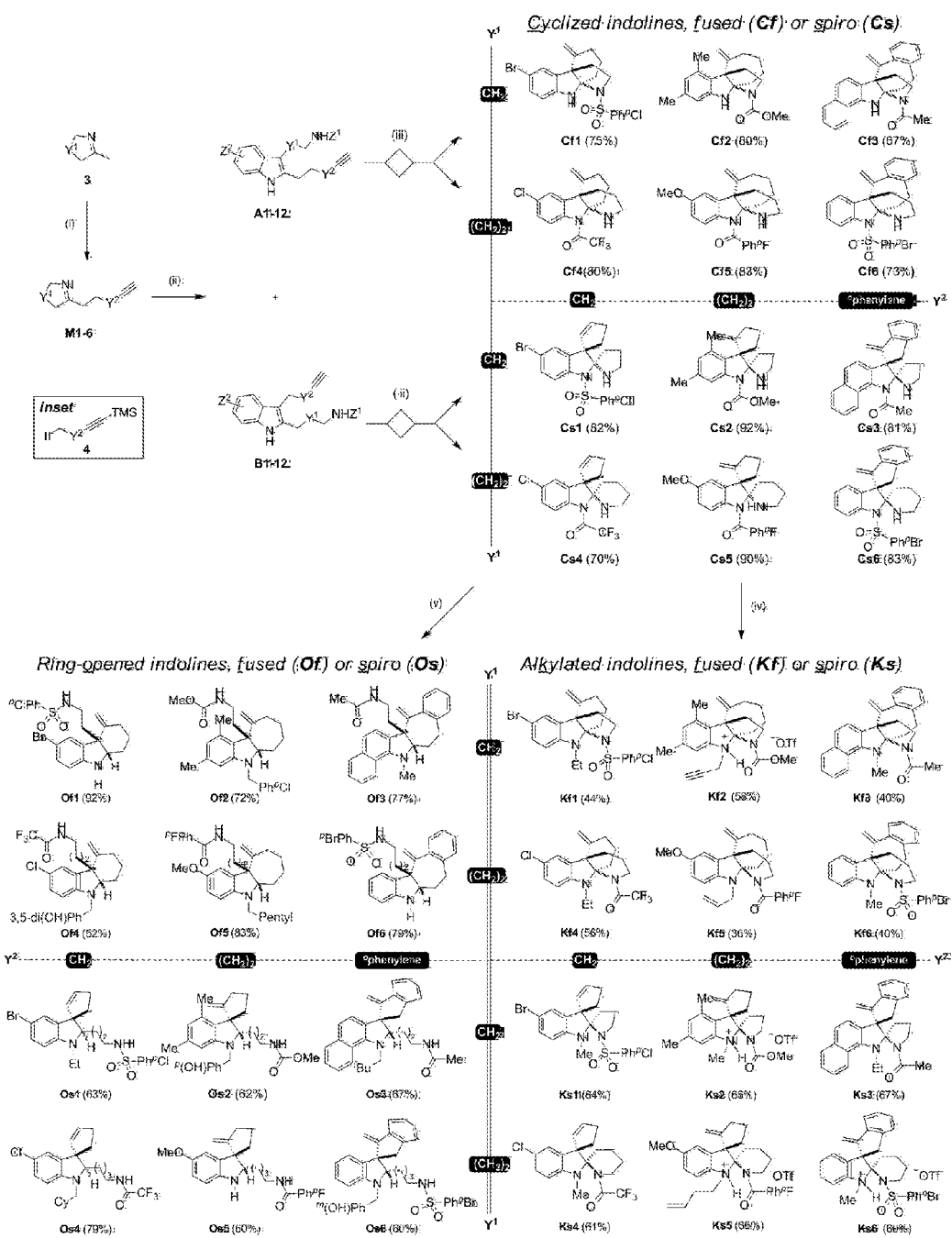
FIG. 1 shows one synthetic method of polycyclic indoline alkaloids. (i) LDA, 4, THF, −78° C.→23° C., 12 h; TBAF, THF, 23° C., 10 min; (ii) 1, DMAP, 23° C., 0.5 h, DMF; M, 2-12 h; TsOH.H$_2$O, 23° C.→80° C., 24 h; (iii) Ph$_3$PAuNTf$_2$, 50° C., toluene, 1-12 h; (iv) R$^1$OTf, DCM, 23° C., 2-12 h; (v) AcOH, NaBH$_3$CN, MeOH, 0° C., 0.5 h; then aldehyde, 0° C.→23° C., 2-12 h.
Figure 2:
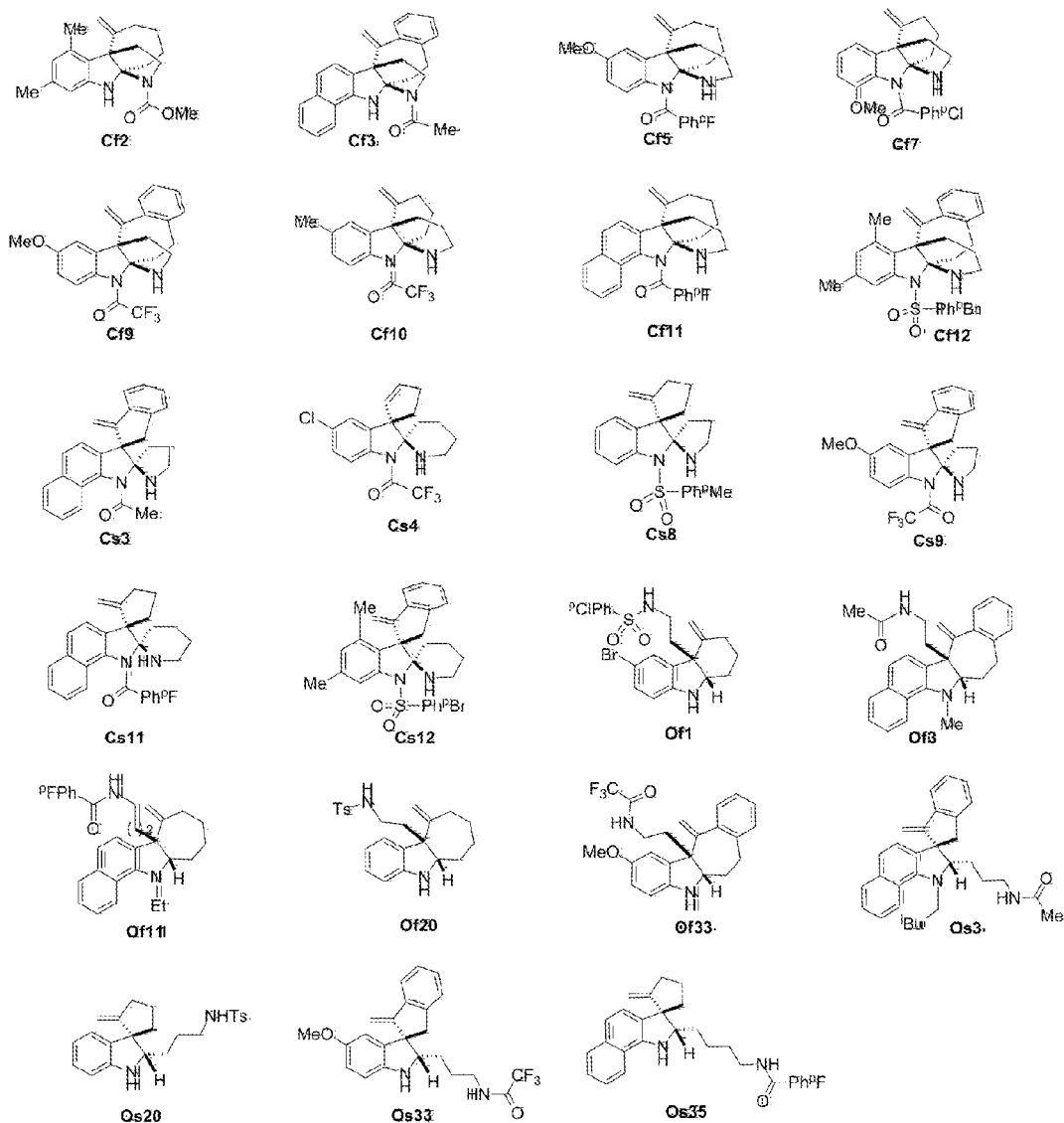
FIG. 2 shows some of the representative indoline compounds of the invention.
Figure 3:
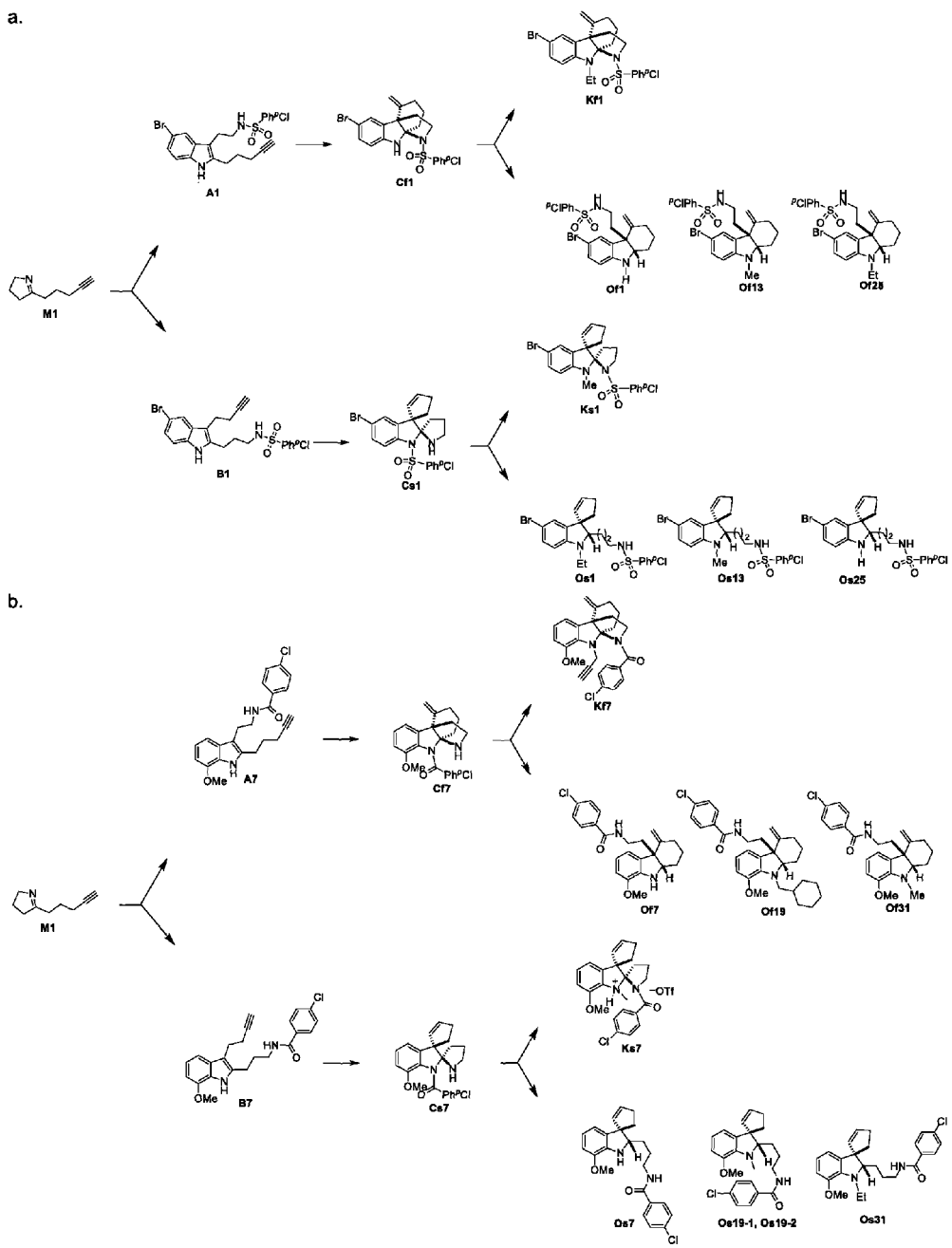
FIGS. 3-8 shows some of the indoline compounds synthesized from alkynyl imines M1-M6, respectively.
Figure 4:
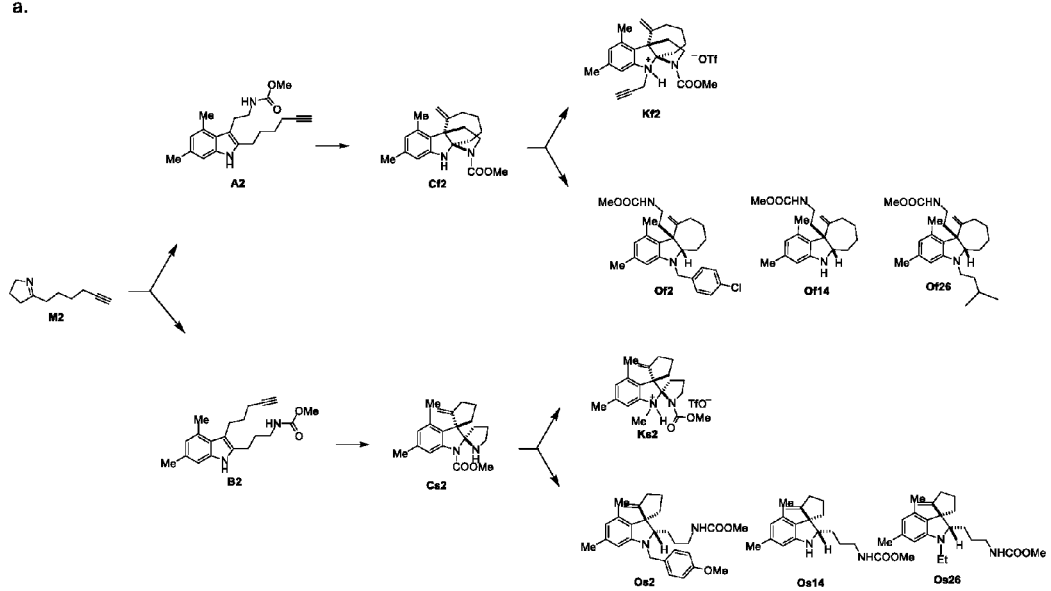
Figure 4:
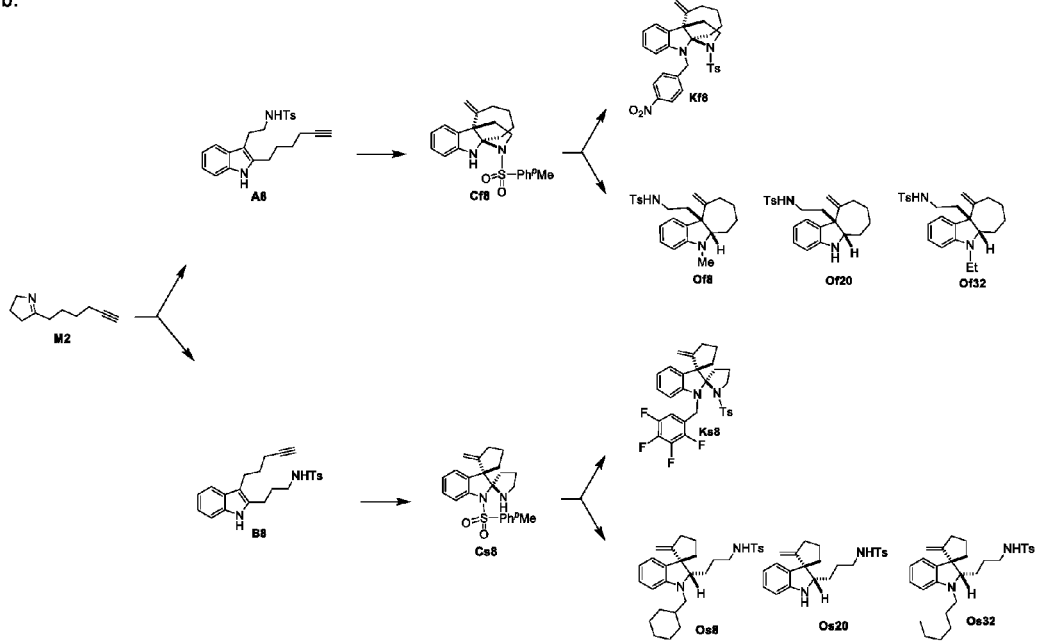
Figure 5:
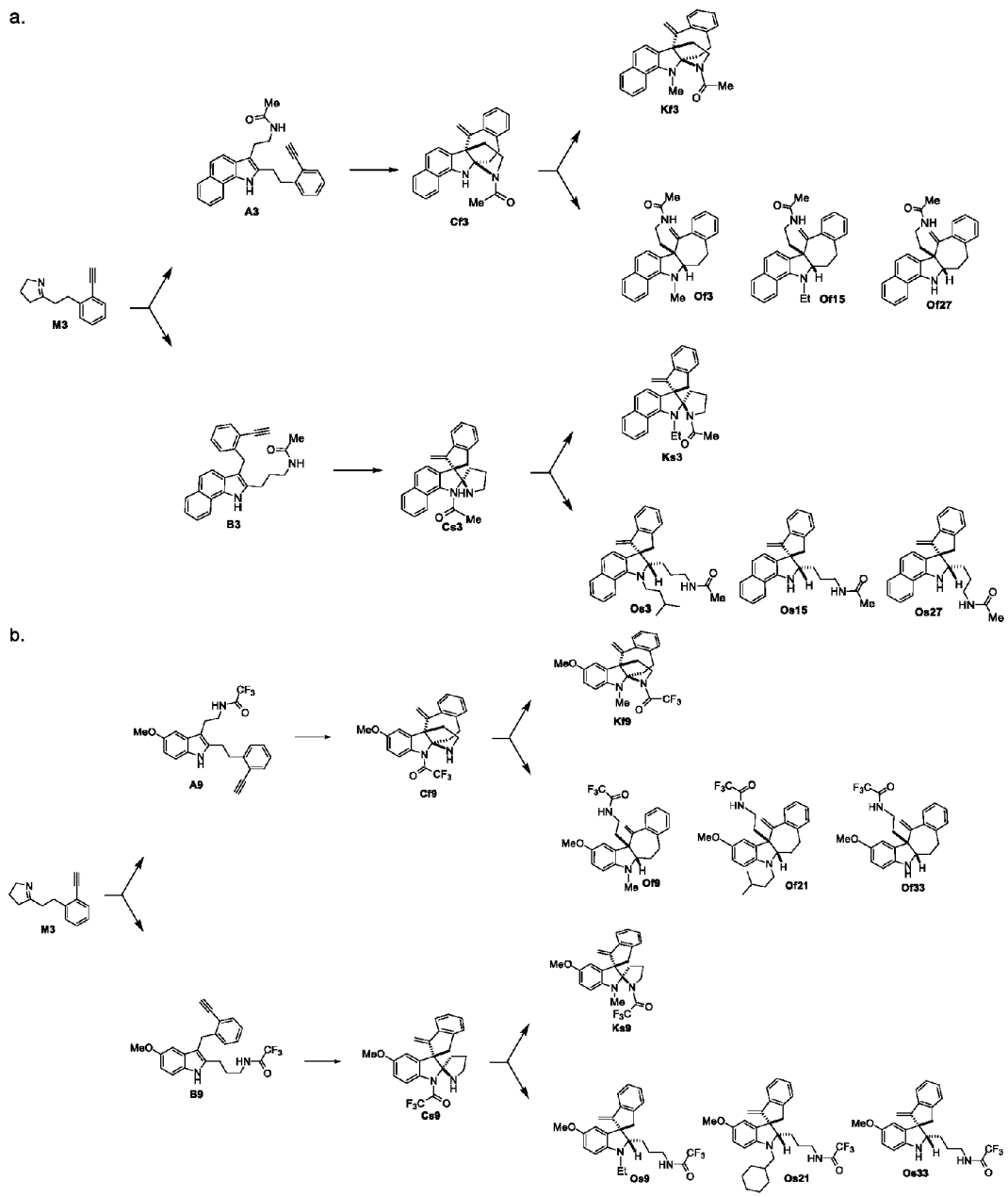
Figure 6:
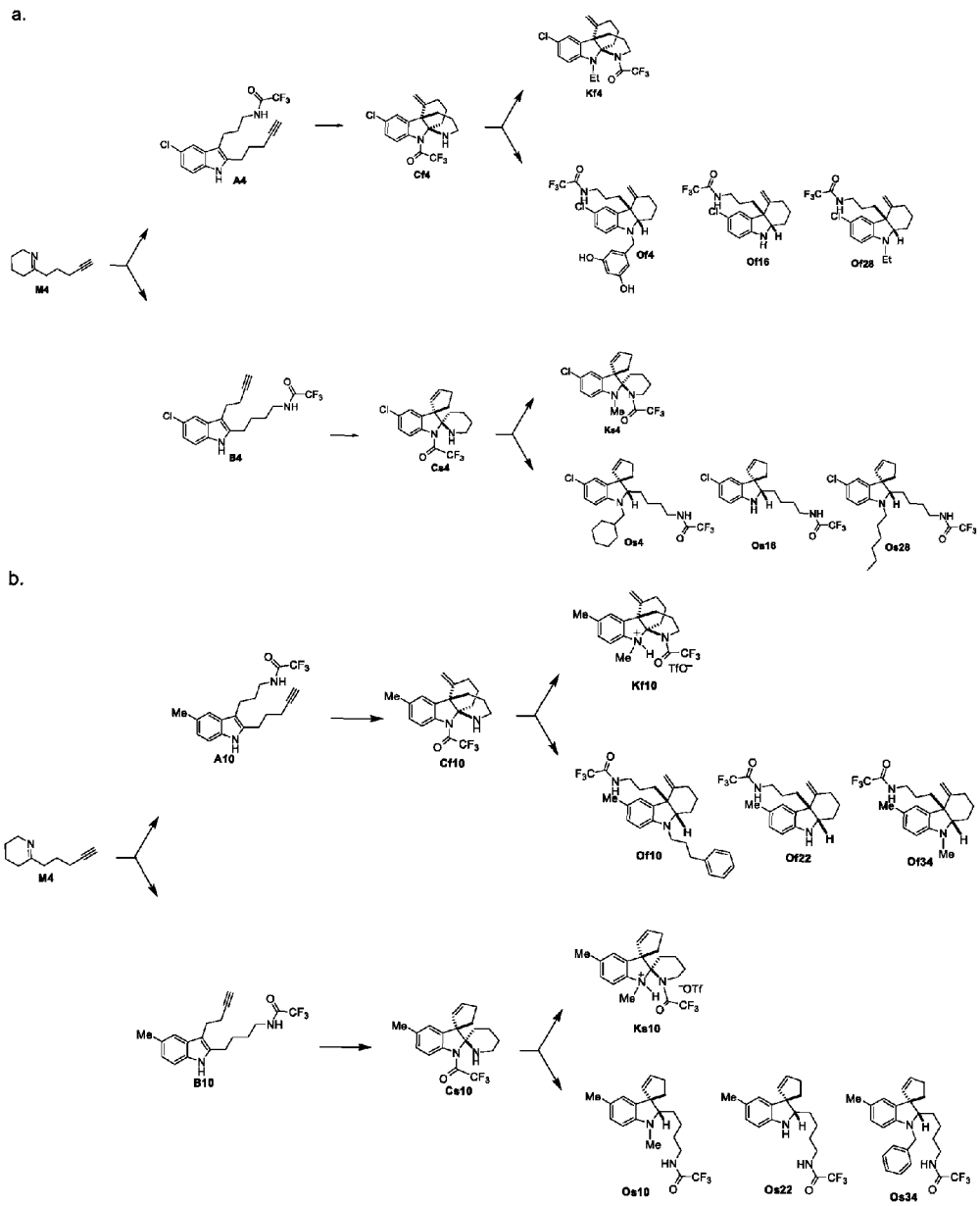
Figure 7:
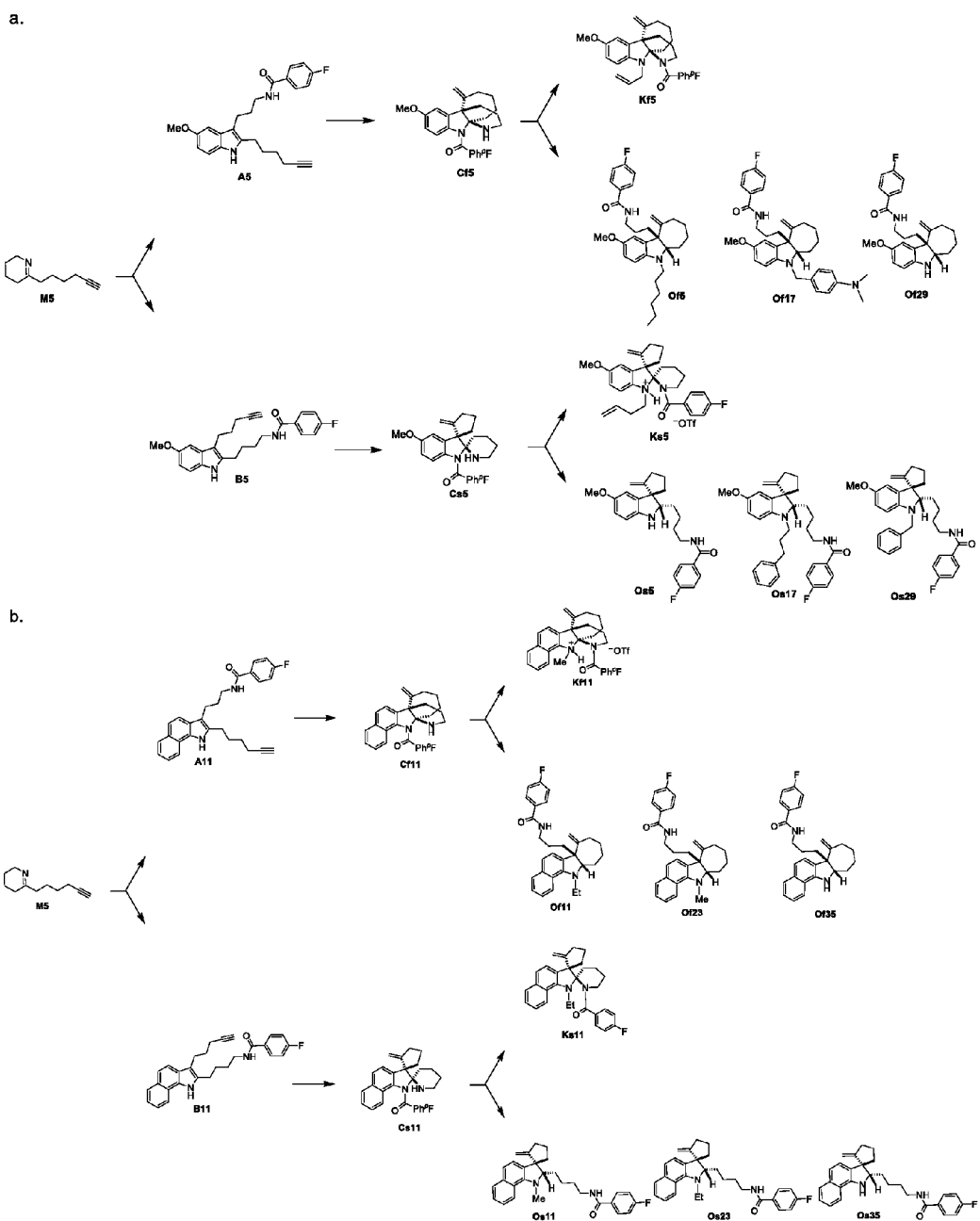
Figure 8:
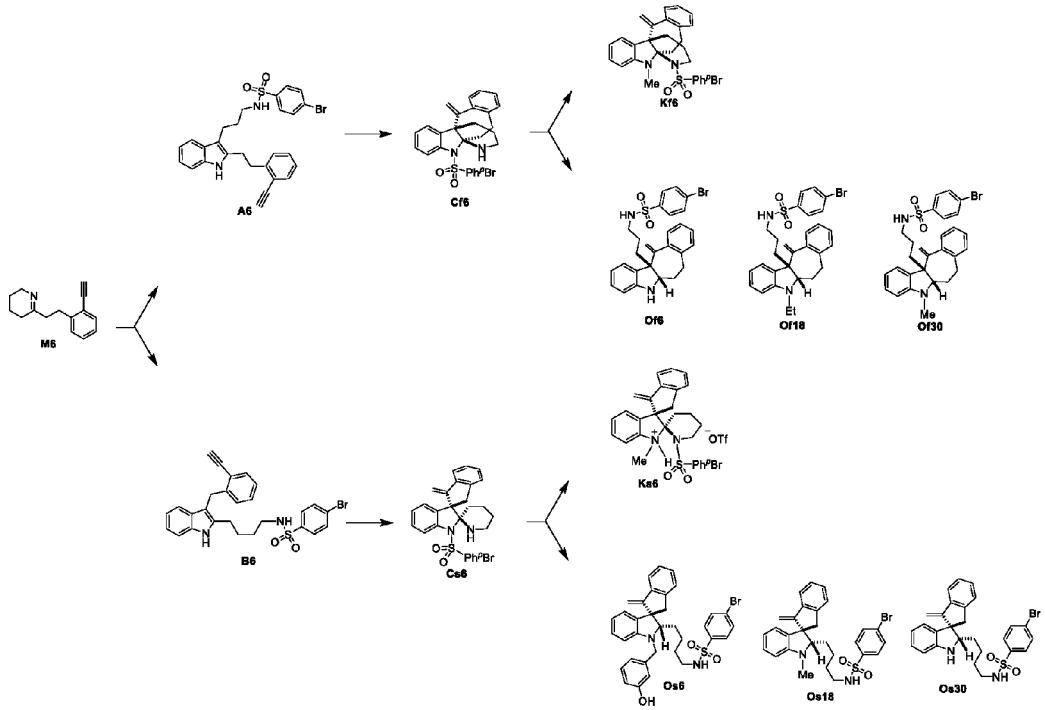
Figure 8:
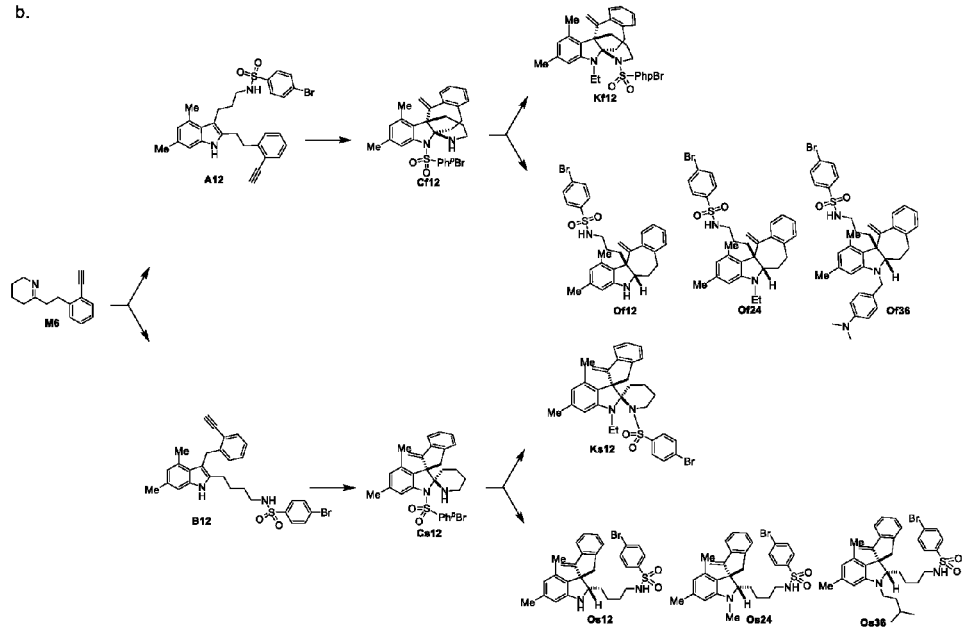

Some aspects of the invention provide an indoline alkaloid compound that is capable of re-sensitizing the susceptibility of methicillin-resistant S. aureus to a β-lactam antibiotic. In one particular embodiment, the indoline alkaloid compound is of the formula:

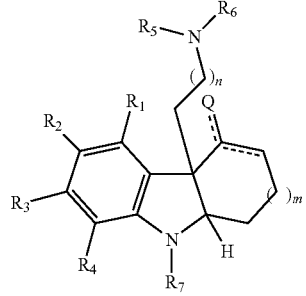

Compound A where each of m and n is independently 1 or 2; one of the dotted lines is a double bond, provided Q is $CH_2$ when the double bond is exocyclic, and Q is H when the double bond is endocyclic; each of $R_1$, $R_3$ and $R_4$ is independently hydrogen or halide, or $R_3$ and $R_4$ together with the carbon atoms to which they are attached form phenyl; $R_2$ is hydrogen, halide, alkyl, or alkoxide; $R_5$ is hydrogen, alkyl, —S(O)$_2$ Ar$^1$ or —COAr$^1$; $R_6$ is hydrogen, —S(O)$_2$Ar$^2$, —COAr$^2$ or —COR$^8$; $R_7$ is hydrogen, alkyl, —S(O)$_2$Ar$^3$ or —COAr$^3$; $R^8$ is alkyl or haloalkyl; each of Ar$^1$ and Ar$^3$ is independently optionally substituted aryl; and Ar$^2$ is optionally substituted aryl or optionally substituted heteroaryl. In some embodiments, when $R_6$ is —S(O)$_2$-Ph-p-Cl and $R_2$ is Br, at least one of $R_1$, $R_3$, $R_4$, $R_5$ and $R_7$ is not hydrogen. In one embodiment, m is 1. Yet in another embodiment, n is 1.

In another embodiment, the indoline alkaloid is of the formula:

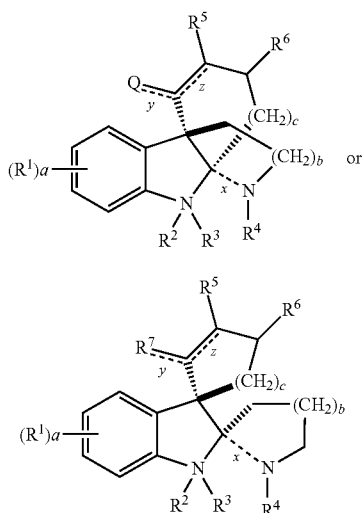

Compound I

Compound II where at most only one of the dotted lines y or z is a double bond (in some embodiments neither y or z is a double bond, yet in other embodiments y is a double bond, still in some embodiments, z is a double bond), provided Q is $CH_2$ when the double bond is exocyclic, and Q is H when the double bond is endocyclic; a is an integer from 0 to 4; each of b and c is independently 1 or 2; dotted bond x can optionally be absent in which case the nitrogen atom of the dotted bond x further comprises $R^a$, wherein $R^a$ is hydrogen or alkyl; $R^7$ is $CH_2$ or when the dotted double bond y is absent, $R^7$ is a hydrogen atom or $CH_3$; each of $R^1$ is independently halide, alkyl, or alkoxide, or when a is an integer of at least two, two of $R^1$'s together with the carbon atoms to which they are attached to can form an optionally substituted aryl group; $R^2$ is absent, hydrogen or alkyl; $R^3$ is hydrogen, alkyl, a nitrogen protecting group, (cycloalkyl)alkyl, (optionally substituted aryl)alkyl, alkenyl, or alkynyl; $R^4$ is hydrogen, alkyl, or a nitrogen protecting group; and $R^5$ and $R^6$ are hydrogen or together along with the carbon atoms to which they are attached to form an optionally substituted aryl group, provided that when $R^5$ and $R^6$ along with the carbon atoms to which they are attached to form an optionally substituted aryl group the dotted double bond z is absent. In some embodiments, a is 0, 1 or 2; and/or each of $R^1$ is independently selected from the group consisting of fluoro, methyl, bromo, chloro, or methoxy; and/or $R^2$ is absent. Yet in other embodiments, a is 2 and $R^1$'s together along with the carbon atoms to which they are attached to form an optionally substituted aryl group. Still in other embodiments, $R^3$ is selected from the group consisting of hydrogen, alkyl, (optionally substituted phenyl) methyl, alkynyl, alkenyl, (cyclohexyl)methyl, —C(=O)$R^b$, and —SO$_2$Ar$^1$, wherein $R^b$ is alkyl, haloalkyl, alkoxy, or optionally substituted phenyl, and Ar$^1$ is optionally substituted aryl; and/or c is 1 or 2. Still in other embodiments, $R^4$ is selected from the group consisting of hydrogen, alkyl, tosylate, —C(=O)$R^b$, and —SO$_2$Ar$^1$, wherein $R^b$ is alkyl, haloalkyl, alkoxy, alkenyl, or optionally substituted phenyl, and Ar$^1$ is optionally substituted aryl; and/or $R^5$ and $R^6$ together along with the carbon atoms to which they are attached to form an optionally substituted aryl group.

As used herein, the terms "halide," "halogen" and "halo" are used interchangeably herein and refer to fluoro, chloro, bromo, or iodo. The term "alkyl" refers to a saturated linear monovalent hydrocarbon moiety of one to twenty, typically one to fifteen, and often one to ten carbon atoms or a saturated branched monovalent hydrocarbon moiety of three to twenty, typically three to fifteen, and often three to ten carbon atoms. Exemplary alkyl group include, but are not limited to, methyl, ethyl, n-propyl, 2-propyl, tert-butyl, pentyl, iso-pentyl, hexyl, and the like. "Alkylene" refers to a saturated linear divalent hydrocarbon moiety of one to twenty, typically one to fifteen and often one to ten carbon atoms or a branched saturated divalent hydrocarbon moiety of three to twenty, typically three to fifteen and often three to ten carbon atoms. Exemplary alkylene groups include, but are not limited to, methylene, ethylene, propylene, butylene, pentylene, and the like. "Alkoxide" or "alkoxy" refers to a moiety of the formula —OR$^x$, where R$^x$ is alkyl as defined herein. "Alkoxycarbonyl" refers to a moiety of the formula —C(=O)OR$^z$, where R$^z$ is alkyl, aralkyl, aryl, haloalkyl or the like as defined herein. "Haloalkyl" refers to an alkyl group as defined herein in which one or more hydrogen atom is replaced by same or different halide atoms. The term "haloalkyl" also includes perhalogenated alkyl groups in which all alkyl hydrogen atoms are replaced by halogen atoms. Exemplary haloalkyl groups include, but are not limited to, —CH$_2$Cl, —CF$_3$, —CH$_2$CF$_3$, —CH$_2$CCl$_3$, and the like. "Cycloalkyl" refers to a non-aromatic, typically saturated, monovalent mono- or bicyclic hydrocarbon moiety of three to ten ring carbons. The cycloalkyl can be optionally substituted with one or more, typically one, two, or three, substituents within the ring structure. When two or more substituents are present in a cycloalkyl group, each substituent is independently selected. The terms "(cycloalkyl)alkyl" and "cycloalkylalkyl" are used interchangeably herein and refer to a moiety of the formula —R$^d$R$^e$ where R$^d$ is an alkylene group and R$^e$ is a cycloalkyl group as defined herein. Exemplary cycloalkylalkyl groups include, but are not limited to, cyclopropylmethyl, cyclohexylpropyl, 3-cyclohexyl-2-methylpropyl, and the like. "Aryl" refers to a monovalent mono-, bi- or tricyclic aromatic hydrocarbon moiety of 6 to 15 ring atoms such as phenyl, naphthyl, etc. "Optionally substituted aryl" refers to an aryl group that is optionally substituted with one or more, typically one, two, or three substituents within the aryl ring structure. When two or more substituents are present in an aryl group, each substituent is independently selected. The terms "aralkyl" and "(aryl)alkyl" are used interchangeably herein and refer to a moiety of the formula —R$^d$R$^e$ where R$^d$ is alkylene and R$^e$ is aryl as defined herein. Exemplary aralkyl or arylalkyl groups include, but are not limited to, phenylmethyl (i.e., benzyl), naphthylmethyl, phenylethyl, phenylpropyl, and the like. "Aralkoxy" refers to a moiety of the formula —OR$^b$Ar$^b$, where R$^b$ is alkylene and Ar$^b$ is optionally substituted aryl as defined herein. "Alkenyl" means a linear monovalent hydrocarbon moiety of two to ten carbon atoms or a branched monovalent hydrocarbon moiety of three to ten carbon atoms, containing at least one carbon-carbon double bond, e.g., ethenyl, propenyl, and the like. "Alkynyl" means a linear monovalent hydrocarbon moiety of two to ten carbon atoms or a branched monovalent hydrocarbon moiety of three to ten carbon atoms, containing at least one carbon-carbon triple bond, e.g., ethenyl, propenyl, and the like. "Acyl" refers to a moiety of the formula —C(O)R', where R' is alkyl, haloalkyl, aryl, or aralkyl. "Sulfonyl" refers to a moiety of the formula —S(O)$_2$R$^y$, where R$^y$ is alkyl, haloalkyl, optionally substitute aryl, optionally substituted aralkyl, or (cycloalkyl)alkyl. "Enantiomeric excess" refers to the difference between the amount of enantiomers. The percentage of enantiomeric excess (% ee) can be calculated by subtracting the percentage of one enantiomer from the percentage of the other enantiomer. For example, if the % ee of (R)-enantiomer is 99% and % ee of (S)-enantiomer is 1%, the % ee of (R)-isomer is 99%–1% or 98%. "Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like. "Pharmaceutically acceptable excipient" refers to an excipient that is useful in preparing a pharmaceutical composition that is generally safe, non-toxic and neither biologically nor otherwise undesirable, and includes excipient that is acceptable for veterinary use as well as human pharmaceutical use. "Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. The terms "pro-drug" and "prodrug" are used interchangeably herein and refer to a pharmacologically substantially inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo when they undergo solvolysis under physiological conditions or undergo enzymatic degradation. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, *Design of Prodrugs*, pp. 7-9, 21-24, Elsevier, Amsterdam 1985 and Silverman, *The Organic Chemistry of Drug Design and Drug Action*, pp. 352-401, Academic Press, San Diego, Calif., 1992). Prodrugs commonly known in the art include acid derivatives that are well known to one skilled in the art, such as, but not limited to, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability. For example, a compound of the invention having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of the invention. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters which are covalently bonded to the above substituents of a compound of the invention through the carbonyl carbon prodrug sidechain. "Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino or amine protecting groups include, formyl, acyl groups (such as acetyl, trifluoroacetyl, and benzoyl), benzyl, alkoxycarbonyl (such as benzyloxycarbonyl (CBZ), and tert-butoxycarbonyl (Boc)), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), sulfonyl, and the like. "Corresponding protecting group" means an appropriate protecting group corresponding to the heteroatom (i.e., N, O, P or S) to which it is attached. "A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated. "Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms. When describing a chemical reaction, the terms "treating", "contacting" and "reacting" are used interchangeably herein, and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. As used herein, the terms "those defined above" and "those defined herein" when referring to a variable incorporates by reference the broad definition of the variable as well as any narrow definitions, if any.

With respect to Compounds I and/or II, in some embodiments, a is 0, 1 or 2. Still in other embodiments, each of $R^1$ is independently selected from the group consisting of fluoro, methyl, bromo, chloro, or methoxy. Yet in other embodiments, a is 2 and $R^1$'s together along with the carbon atoms to which they are attached to form an optionally substituted aryl group, typically a phenyl group such that together with the phenyl group already present comprises a naphthyl group. In other embodiments, $R^2$ is absent. Yet in other embodiments, $R^3$ is selected from the group consisting of hydrogen, alkyl, (optionally substituted phenyl)methyl, alkynyl, alkenyl, (cyclohexyl)methyl, a nitrogen protecting group. Within these embodiments, in some instances, the nitrogen protecting group is selected from the group consisting of an acyl, alkoxycarbonyl, and sulfonyl. Within these instances, in some cases, acyl is of the formula —C(=O)$R^b$, alkoxycarbonyl is of the formula —C(=O)O$R^b$, and the sulfonyl group is of the formula —SO$_2$Ar$^1$, wherein $R^b$ is alkyl, haloalkyl, alkoxy, aralkoxy, or optionally substituted phenyl, and Ar$^1$ is optionally substituted aryl. Still in other embodiments, $R^4$ is selected from the group consisting of hydrogen, alkyl, tosylate, —C(=O)$R^b$, and —SO$_2$Ar$^1$, where $R^b$ is alkyl, haloalkyl, alkoxy, alkenyl, or optionally substituted phenyl, and Ar$^1$ is optionally substituted aryl. In some embodiments, $R^5$ and $R^6$ together along with the carbon atoms to which they are attached to form an optionally substituted aryl group. Within these embodiments, in some cases $R^5$ and $R^6$ together along with the carbon atoms to which they are attached to form a phenyl group. Yet in other embodiments, c is 1. And in other embodiments, c is 2.

Another aspect of the invention provides an antibiotic composition comprising an indoline alkaloid compound that is capable of re-sensitizing the susceptibility of methicillin-resistant S. aureus to said β-lactam antibiotic. In some embodiments, the antibiotic composition further includes a β-lactam antibiotic. Suitable β-lactam antibiotics are well known to one skilled in the art, and exemplary β-lactam antibiotics can be found in Merck Index, 15th Ed., Edited by Maryadele J O'Neil, Royal Society of Chemistry, 2013, and Physicians' Desk Reference (i.e., "PDR") 67th Ed., 2013, all of which are incorporated herein by reference in their entirety. In some embodiments, the antibiotic composition comprises an indoline alkaloid compound described herein.

Still another aspect of the invention provides a method for treating bacterial infection in a subject comprising administering to the subject in need of such a treatment a therapeutically effective amount of a β-lactam antibiotic and an indoline alkaloid compound (such as those disclosed herein) that is capable of re-sensitizing the susceptibility of methicillin-resistant S. aureus to said β-lactam antibiotic.

Still another aspect of the invention provides a method for producing a fused-indoline alkaloid compound of the formula:

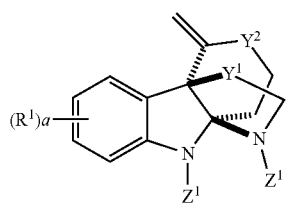

Compound IA said method comprising contacting a substituted indole compound of the formula:

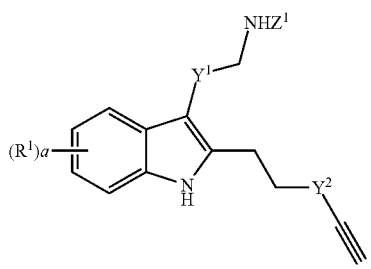

with a gold catalyst under conditions sufficient to produce the fused-indoline alkaloid compound of Formula IA, where a is an integer from 0 to 4; each of $R^1$ is independently halide, alkyl, or alkoxide, or alternatively, when a is an integer of at least two, two of $R^1$'s together with the carbon atoms to which they are attached to can form an aryl group; $Y^1$ is (CH$_2$)$_b$, wherein b is 1 or 2; $Y^2$ is

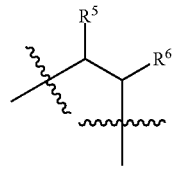

or (CH$_2$)$_c$, wherein c is 1 or 2, and wherein $R^5$ and $R^6$ are hydrogen or together along with the carbon atoms to which they are attached to form an optionally substituted aryl group; and one of $Z^1$ is hydrogen and the other is alkyl, a nitrogen protecting group, (cycloalkyl)alkyl, (optionally substituted aryl)alkyl, alkenyl, or alkynyl.

In general, the gold catalyst can be any Au(I)-containing organometallic complexes that can effect cyclization of the starting material to produce the desired indoline alkaloid compound. Such gold catalysts include, but are not limited to, a commercially available Ph$_3$PAuNTf$_2$. In some embodiments, the gold catalyst is Ph$_3$PAuNTf$_2$, or any other Au(I)-containing organometallic complexes.

Compound IA can be converted to compound I (where dotted line x is a single bond) or compound A, by any of the reductive amination processes known to one skilled in the art. Typically, compound IA is converted to compound I or compound A by reacting compound IA with a borohydride reducing agent. Suitable borohydride reducing agents include, but are not limited to, MBH$_4$ and MBH$_3$CN, where M is Na, Li, K, or other metal. In some embodiments, the reductive amination step also includes an acid, such as a carboxylic acid, e.g., acetic acid.

Another aspect of the invention provides, a method for producing a spiro-indoline alkaloid compound of the formula:

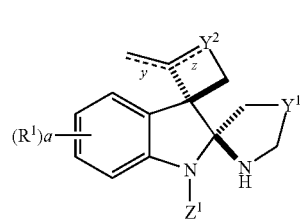

Compound IB said method comprising, contacting a substituted indole compound of the formula:

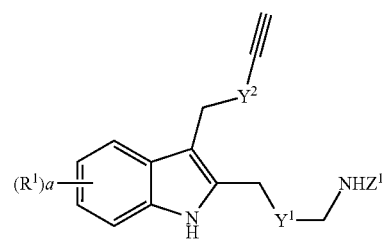

with a gold catalyst under conditions sufficient to produce the spiro-indoline alkaloid compound of Formula IB, where a is an integer from 0 to 4; at most only one of y and z dotted double bond is present; each of $R^1$ is independently halide, alkyl, or alkoxide, or alternatively, when a is an integer of at least two, two of $R^1$'s together with the carbon atoms to which they are attached to can form an aryl group; $Y^1$ is $(CH_2)_b$, wherein b is 1 or 2; $Y^2$ is

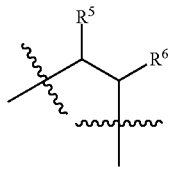

or $(CH_2)_c$, wherein c is 1 or 2, and wherein $R^5$ and $R^6$ are hydrogen or together along with the carbon atoms to which they are attached to form an optionally substituted aryl group, provided that when $R^5$ and $R^6$ along with the carbon atoms to which they are attached to form an optionally substituted aryl group the dotted double bond z is absent; and $Z^1$ is alkyl, a nitrogen protecting group, (cycloalkyl) alkyl, (optionally substituted aryl)alkyl, alkenyl, or alkynyl.

A similar gold catalyst as that described above can be used in producing the spiro-indoline alkaloid compound of Formula IB. In some embodiments, the gold catalyst is $Ph_3PAuNTf_2$, or any other Au(I)-containing organometallic complexes.

The starting materials for producing compounds of Formulas IA and IB are readily apparent to those having read the present disclosure. In addition, as disclosed below, methods of the invention can also include further transformation of compounds of Formulas IA and IB, e.g., "ring opening" or "alkylation" reaction.

Still further, combinations of various particular embodiments described herein form other embodiments. For example, in one particularly embodiment a is 1, and $R^1$ is bromo, $R^2$ is absent, $R^3$ is $-C(=O)R^b$, $R^b$ is trifluoromethyl, $R^4$ is hydrogen, $R^5$ and $R^6$ together along with the carbon atoms to which they are attached to form a phenyl group, b is 1 and c is 2. In this manner, a variety of specific compounds are embodied within the present invention.

Some of the representative compounds of Formula A and antibacterial activities are provided in the following tables:

| analogs of Ofl |
|---|

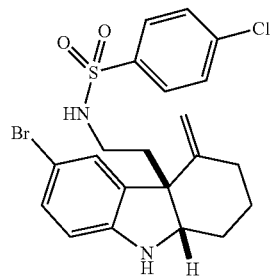 [SMILES: C=C1CCC[C@@H]2Nc3ccc(Br)cc3[C@]12CCNS(=O)(=O)c1ccc(Cl)cc1]

Ofl

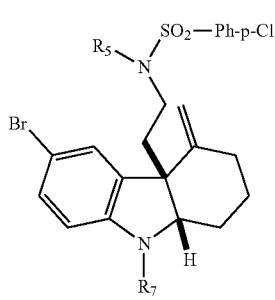

1a-1

| Cpd | $R_7$ | $R_5$ | amox/clav[a,b] | cefazolin[a,b] | methicillin[a,b] | meropenem[a,c] |
|---|---|---|---|---|---|---|
| 1a | Me | — | >32 | >32 | >32 | >32 |
| 1b | $SO_2Ph^pCl$ | — | >32 | >32 | >32 | >32 |
| 1c | $COPh^pCl$ | — | >32 | >32 | >32 | >32 |
| 1d | Cbz | — | >32 | >32 | >32 | >32 |
| 1e | Allyl | — | >32 | >32 | >32 | >32 |
| 1f | Tetraethylene glycol | — | >32 | >32 | >32 | >32 |
| 1g | — | Me | >32 | >32 | >32 | >32 |
| 1h | — | $SO_2Ph^pCl$ | >32 | >32 | >32 | >32 |
| 1i | — | $COPh^pCl$ | >32 | >32 | >32 | >32 |
| 1j | — | Cbz | >32 | >32 | >32 | >32 |
| 1k | — | Allyl | >32 | >32 | >32 | >32 |
| 1l | Cbz | Cbz | >32 | >32 | >32 | >32 |

[a]All MRC values are in μg/mL;
[b]MRSA ATCC BAA-44;
[c]MRSA ATCC 33592.

Activities listed in the table show the ability of the compounds of the invention to resensitize MRSA to a collection of β-lactam antibiotics. For these activity tests, AMOXICILLIN® was used in combination with clavulanic acid (a.k.a., AUGMENTIN®), CEFAZOLIN®, and MEROPENEM® (an ultra-broad-spectrum carbapenem). AMOXICILLIN®/clavulanic acid and CEFAZOLIN® resensitizing experiments were performed using MRSA ATCC BAA-44 in which the minimum inhibitory concentrations (MICs) of these two antibiotics were found to be 32/16 μg/ml and 128 μg/ml, respectively. Experiments using MEROPENEM® were performed using MRSA ATCC 33592, since this strain has demonstrated greater level of resistance to MEROPENEM®, with an MIC of 16 μg/ml. To assess activity of each analog as a resistance-modifying agent (RMA), a modified broth microdilution assay was used. Briefly, this involves incubating MRSA with 2-fold serial dilutions of a compound in the presence of each individual antibiotic at its Clinical Laboratory Standards Institutes (CLSI)-defined sensitive concentration. For AMOXICILLIN®/clavulanic acid, this concentration is 4/2 μg/ml (8-fold potentiation), for CEFAZOLIN®, 8 μg/ml (16-fold potentiation) and for MEROPENEM®, 4 μg/ml (4-fold potentiation). Following overnight incubation, plates were examined for bacterial growth, or lack thereof. Compounds were tested at concentrations ranging from 0.5-32 μg/ml. The minimum resensitizing concentration (MRC) was defined as the concentration of compound at which no overnight growth was observed in the presence of a sensitive concentration of antibiotic. Compounds that displayed similar or improved RMA activity relative to compound Of1 were further tested for their toxicity against 'human cervical adenocarcinoma HeLa cells by incubating a range of concentrations of each compound with cells for 24 hours and assessing viability at each concentration using the CellTiter Glo™ mammalian viability assay (Promega). The half growth inhibitory concentration ($GI_{50}$) of each analog was determined by fitting the data using KaleidaGraph (v4.1.1, Synergy Software). Compounds 1a-1 are synthesized as shown in Scheme 1 below.

Scheme 1. Functionalization of the indoline and sulfonamide nitrogen

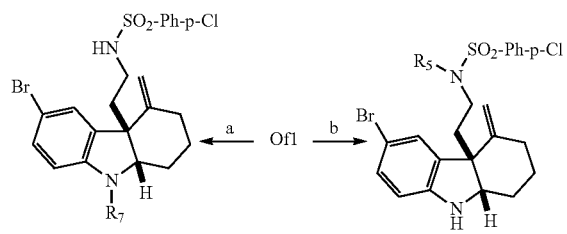

(a) $R_1X$, $K_2CO_3$, 0° C., $CH_3CN$; for 1f, standard reductive amination conditions;
(b) For 1g, NaH 0° C., then MeI 0-60° C., DMF; for 1h-1, $R_2X$, $Et_3N$, 0° C., DCM Table below shows activity of compounds with various aromatic ring substituents, which were prepared according to Scheme 2:

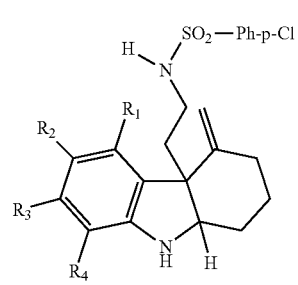

6a-n

| Cpd | $R_1$ | $R_2$ | $R_3$ | $R_4$ | amox/clav[a,b] | cefazolin[a,b] | methicillin[a,b] | meropenem[a,c] | $GI_{50}$[d] |
|---|---|---|---|---|---|---|---|---|---|
| Of1 | H | Br | H | H | 4 | 4 | 8 | 4 | 17.1 |
| 6a | H | Cl | H | H | 8 | 4 | 8 | 8 | 35 |
| 6b | H | Me | H | H | 16 | 16 | 32 | 32 | — |
| 6c | H | MeO | H | H | >32 | >32 | >32 | >32 | — |
| 6d | H | F | H | H | 16 | 16 | 16 | 16 | — |
| 6e | H | H | H | H | 16 | 16 | 16 | 16 | — |
| 6f | H | H | phenylene | | >32 | >32 | >32 | >32 | — |
| 6g | H | H | H | Br | >32 | 32 | >32 | 8 | — |
| 6h | H | H | Br | H | 16 | 16 | 32 | 16 | — |
| 6i | Br | H | H | H | 32 | 16 | >32 | 16 | — |
| 6j | H | Cl | H | F | 16 | 16 | 32 | 32 | — |
| 6k | H | Cl | H | Cl | 4 | 4 | 4 | 4 | 13.6 |
| 6l | H | Br | H | F | 2 | 4 | 2 | 4 | 18.1 |
| 6m | Br | H | H | F | >32 | >32 | >32 | 8 | — |
| 6n | Br | H | H | Br | >32 | >32 | >32 | 4 | — |

[a]MRC values are in μg/mL;
[b]MRSA ATCC BAA-44;
[c]MRSA ATCC 33592;
[d]HeLa cells,
$GI_{50}$ values are in μg/mL.

Scheme 2. Synthesis of compounds 6a-n

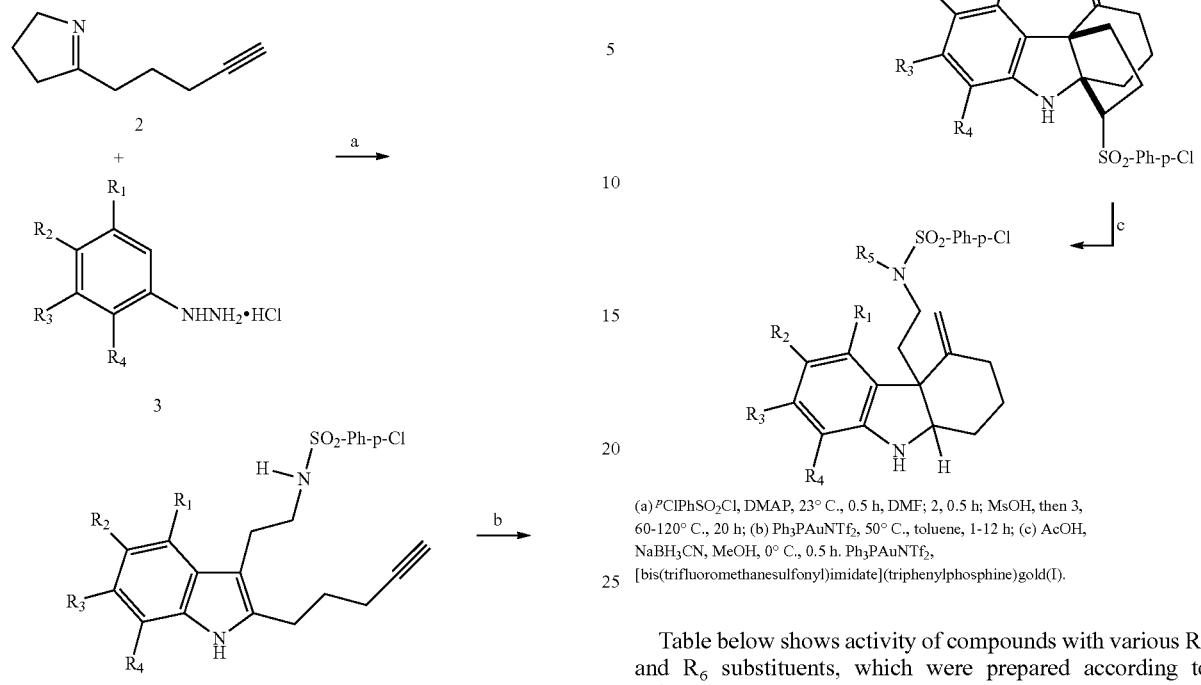

(a) $^p$ClPhSO$_2$Cl, DMAP, 23° C., 0.5 h, DMF; 2, 0.5 h; MsOH, then 3, 60-120° C., 20 h; (b) Ph$_3$PAuNTf$_2$, 50° C., toluene, 1-12 h; (c) AcOH, NaBH$_3$CN, MeOH, 0° C., 0.5 h. Ph$_3$PAuNTf$_2$, [bis(trifluoromethanesulfonyl)imidate](triphenylphosphine)gold(I).

Table below shows activity of compounds with various R$_4$ and R$_6$ substituents, which were prepared according to Scheme 3:

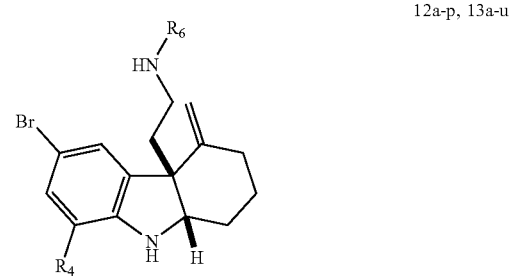

12a-p, 13a-u

| Cpd | R$_4$ | R$_6$ | amox/clav$^{a,b}$ | cefazolin$^{a,b}$ | methicillin$^{a,b}$ | meropenem$^{a,c}$ | GI$_{50}$$^d$ |
|---|---|---|---|---|---|---|---|
| 0f1 | H | SO$_2$Ph$^p$Cl | 4 | 4 | 8 | 4 | 17.1 |
| 11a | H | H | 32 | 32 | 16 | 32 | — |
| 11b | F | H | >32 | 32 | 32 | 16 | 16.2 |
| 12a | H | TFA | >32 | >32 | >32 | 32 | — |
| 12b | H | COBu | >32 | >32 | >32 | 32 | — |
| 12c | H | COPh$^p$Cl | >32 | >32 | >32 | >32 | — |
| 12d | H | SO$_2$Ph | 8 | 8 | 32 | 16 | — |
| 12e | H | SO$_2$Ph$^p$Me | >32 | >32 | 32 | >32 | — |
| 12f | H | SO$_2$Ph$^p$F | >32 | >32 | >32 | >32 | — |
| 12g | H | SO$_2$Ph$^p$Br | 4 | 4 | 8 | 8 | 40 |
| 12h | H | SO$_2$Ph$^p$I | 4 | 4 | 32 | 32 | 33 |
| 12i | H | SO$_2$Ph$^{3,4}$Cl | 4 | 2 | 4 | 4 | 12.8 |
| 12j | H | SO$_2$Ph$^{2,4}$Cl | 8 | >32 | 32 | 4 | — |
| 12k | H | SO$_2$Ph$^p$CN | 16 | 8 | 16 | 16 | — |
| 12l | H | SO$_2$Ph$^p$NHAc | >32 | >32 | 32 | 32 | — |
| 12m | H | SO$_2$$^5$Py | 32 | 32 | 32 | 32 | — |
| 12n | H | SO$_2$Ph$^p$NO$_2$ | >32 | >32 | >32 | >32 | — |
| 12o | H | SO$_2$Ph$^p$NH$_2$ | 16 | 16 | 16 | 16 | — |
| 12p | H | Troc | >32 | >32 | >32 | >32 | — |
| 10a | H | Cbz | >32 | >32 | >32 | >32 | — |
| 13a | F | SO$_2$Ph$^p$OMe | 8 | 4 | 4 | 8 | 49 |
| 13b | F | SO$_2$Ph$^p$Me | 4 | 4 | 4 | 4 | 22 |
| 13c | F | SO$_2$Ph$^p$F | 4 | 4 | 4 | 4 | 18.3 |
| 6l | F | SO$_2$Ph$^p$Cl | 2 | 4 | 2 | 4 | 18.1 |
| 13d | F | SO$_2$Ph$^p$Br | 1 | 1 | 0.25 | 1 | 22 |
| 13e | F | SO$_2$Ph$^p$I | 4 | 2 | 2 | 4 | 19.6 |
| 13f | F | SO$_2$Ph$^{3,4}$Cl | 4 | 4 | 4 | 4 | 31 |

-continued

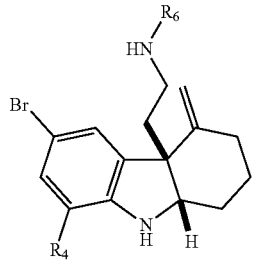

12a-p, 13a-u

| Cpd | R4 | R6 | amox/clav[a,b] | cefazolin[a,b] | methicillin[a,b] | meropenem[a,c] | GI50[d] |
|---|---|---|---|---|---|---|---|
| 13g | F | SO2Ph[p]NHAc | 32 | 32 | 32 | 16 | 32 |
| 13h | F | SO2Ph[p]CN | 8 | 4 | 4 | 4 | 17.0 |
| 13i | F | SO2Ph[p]CF3 | 4 | 4 | 2 | 4 | 8.7 |
| 13j | F | SO2Ph[3,4]Br | 4 | 4 | 2 | 4 | 20 |
| 13k | F | SO2Ph[3]F[4]Br | 4 | 4 | 4 | 4 | 17.5 |
| 13l | F | SO2Ph[2]CF3[4]Br | >32 | >32 | >32 | 4 | 21 |
| 13m | F | SO2Ph[3]CF3[4]Br | 4 | 4 | 2 | 4 | 8.3 |
| 13n | F | SO2Ph[2]Me[4]Br | 4 | 4 | 2 | 4 | 13.5 |
| 13o | F | SO2Ph[3]Me[4]Br | 4 | 4 | 2 | 4 | 12.5 |
| 13p | F | SO2[2]Thiophene[4,5]Br | 4 | 4 | 2 | 4 | 14.6 |
| 13q | F | SO2[3]Py[5]Br | 8 | 8 | 8 | 8 | 11.2 |
| 13r | F | SO2[3]Py[6]Cl | 8 | 8 | 8 | 8 | 16.7 |
| 13s | F | SO2[4]NMI | 32 | 32 | >32 | 32 | 23 |
| 13t | F | SO2[2]Benzofuran | 4 | 4 | 4 | 2 | 12.3 |
| 13u | F | SO2Ph[3]Cl[4]OCF2H | 4 | 4 | 4 | 4 | 15.4 |
| 10b | F | Cbz | >32 | >32 | >32 | >32 | — |

[a]MRC values are in μg/mL;
[b]MRSA ATCC BAA-44;
[c]MRSA ATCC 33592;
[d]HeLa cells,
GI50 values are in μg/mL.

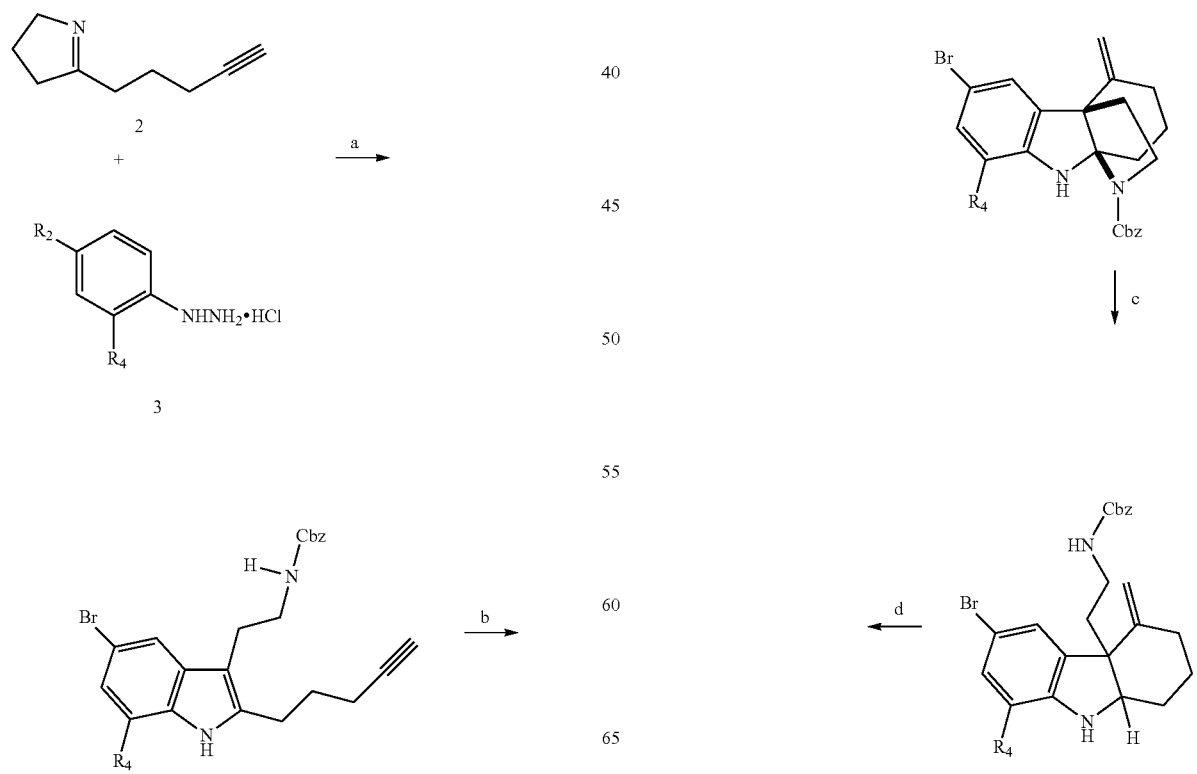

Scheme 3. Synthesis of 12a-p and 13a-u

19
-continued

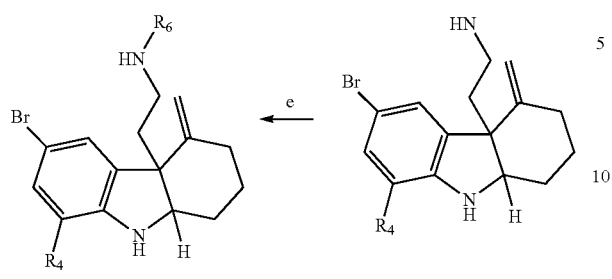

20
-continued

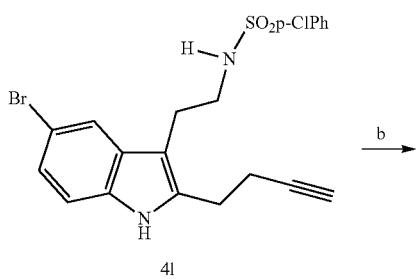

(a) CbzCl, DMAP, 23° C., 0.5 h, DMF; 2, 2-12 h; MsOH, then 3, 60-120° C.; (b) Ph$_3$PAuNTf$_2$, 50° C., toluene, 1-12 h; (c) AcOH, NaBH$_3$CN, MeOH, 0° C., 0.5 h; (d) BF$_3$·Et$_2$O, Me$_2$S, DCM, 23° C., 1.5 h; (e) R$_2$X, Et$_3$N, DCM, 0° C., 5-2 h.

Syntheses of other compounds are illustrated in the following reaction schemes.

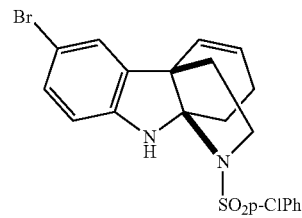

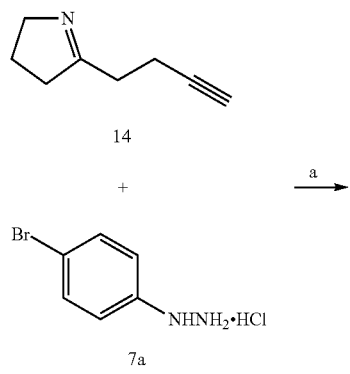

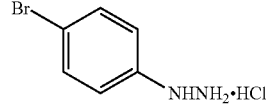

Synthesis of Compound 16: (a) $^p$ClPhSO$_2$Cl, DMAP, 23° C., 0.5 h, DMF; 2, 0.5 h; MsOH, then 3, 120° C., 20 h; (b) Ph$_3$PAuNTf$_2$, 50° C., toluene, 2 h; (c) AcOH, NaBH$_3$CN, MeOH, 0° C., 0.5 h.

Synthesis of Compounds 20, 21a-b

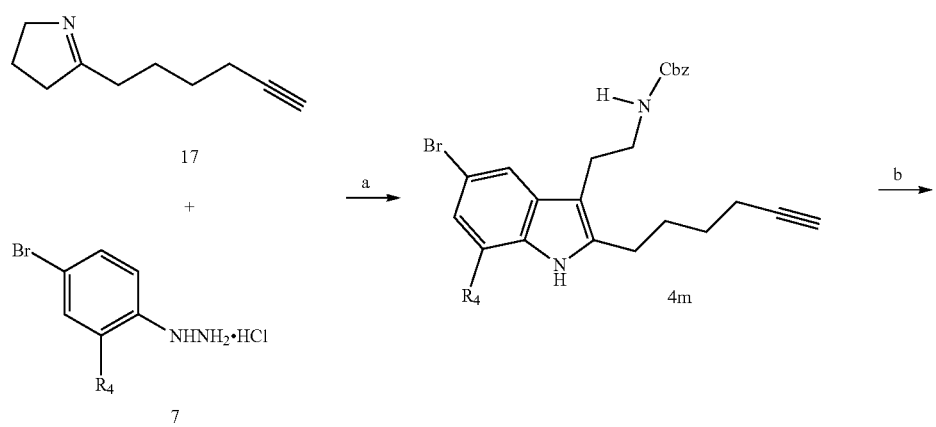

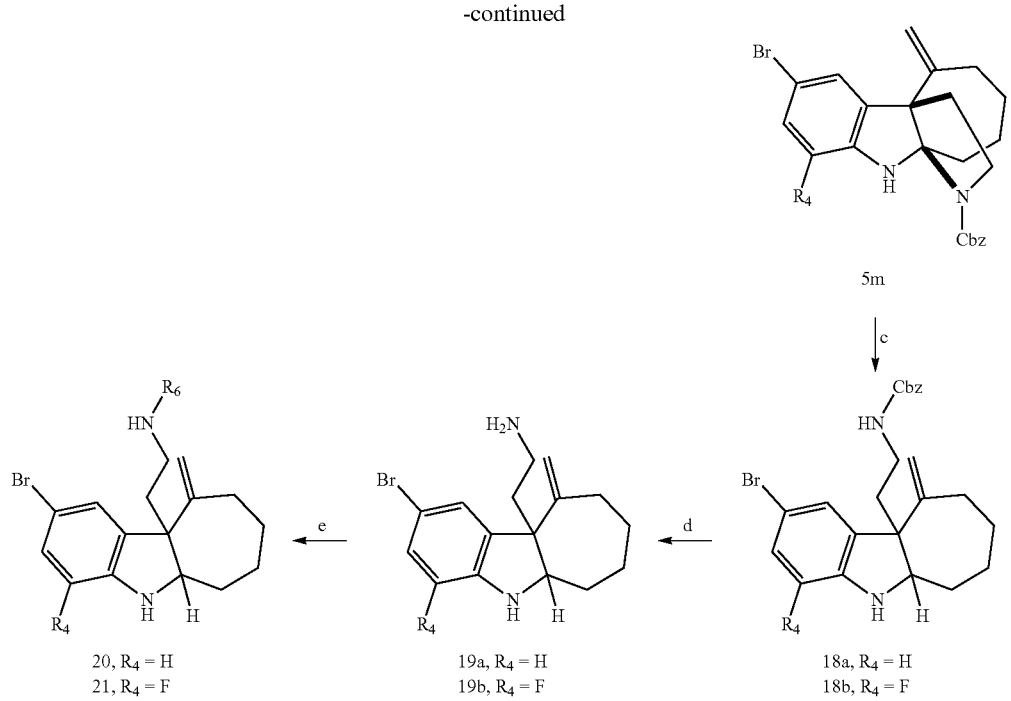

(a) CbzCl, DMAP, 23° C., 0.5 h, DMF; 2, 2-12 h; MsOH, then 3, 60-120° C.; (b) Ph₃PAuNTf₂, 50° C., toluene, 1-12 h; (c) AcOH, NaBH₃CN, MeOH, 0° C., 0.5 h; (d) BF₃·Et₂O, Me₂S, DCM, 23° C., 1.5 h; (e) R₂X, Et₃N, DCM, 0° C., 0.5-2 h.

Synthesis of Compound 23

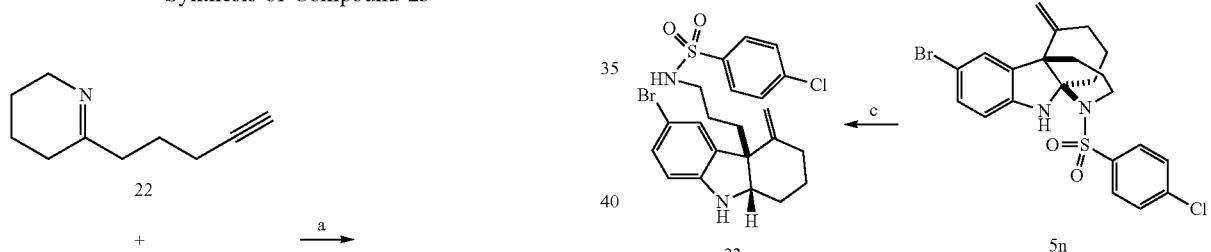

(a) $^p$ClPhSO₂Cl, DMAP, 23° C., 0.5 h, DMF; 2, 0.5 h; MsOH, then 3, 120° C., 20 h; (b) Ph₃PAuNTf₂, 50° C., toluene, 2 h; (c) AcOH, NaBH₃CN, MeOH, 0° C., 0.5 h.

Table below shows activity of various other compounds of the invention:

| Cpd | R₄ | R₆ | amox/clav[a,b] | cefaz-olin[a,b] | meth-icillin[a,b] | meropenem[a,c] |
|---|---|---|---|---|---|---|
| Ofl | H | SO₂Ph$^p$Cl | 4 | 4 | 8 | 4 |
| 16 | H | SO₂Ph$^p$Cl | 4 | 4 | 4 | 8 |
| 20 | H | SO₂Ph$^p$Cl | 4 | 4 | 2 | 4 |
| 18b | F | Cbz | >32 | >32 | >32 | >32 |
| 19b | F | H | 32 | 16 | 16 | 16 |
| 21a | F | SO₂Ph$^p$Br | 16 | 16 | 2 | 16 |
| 21b | F | SO₂Ph$^{3,4}$Cl | 8 | 4 | 8 | 4 |
| 23 | H | SO₂Ph$^p$Cl | 8 | 8 | 4 | 8 |

MRC values are in µg/mL;
[b] MRSA ATCC BAA-44;
[c] MRSA ATCC 33592;
[d] HeLa cells, GI₅₀ values are in µg/mL.

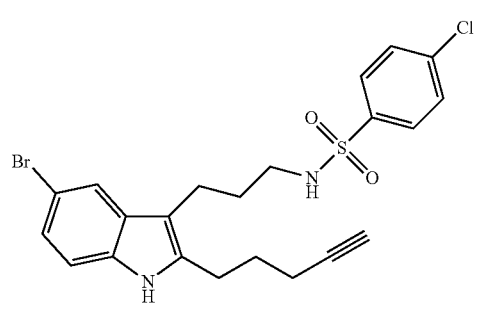

Exemplary compounds of the invention that were prepared include, but are not limited to, the following compounds: 4-Chloro-N-{2-[5-chloro-2-(pent-4-yn-1-yl)-1H- indol-3-yl]ethyl}benzene-1-sulfonamide (4a); 4-Chloro-N-{2-[5-methyl-2-(pent-4-yn-1-yl)-1H-indol-3-yl]ethyl}benzene-1-sulfonamide (4b); 4-Chloro-N-{2-[5-methoxy-2-(pent-4-yn-1-yl)-1H-indol-3-yl]ethyl}benzene-1-sulfonamide (4c); 4-Chloro-N-{2-[5-fluoro-2-(pent-4-yn-1-yl)-1H-indol-3-yl]ethyl}benzene-1-sulfonamide (4d); 4-Chloro-N-{2-[2-(pent-4-yn-1-yl)-1H-indol-3-yl]ethyl}benzene-1-sulfonamide (4e); 4-Chloro-N-{2-[2-(pent-4-yn-1-yl)-1H-benzo[g]indol-3-yl]ethyl}benzene-1-sulfonamide (4f); N-{2-[7-bromo-2-(pent-4-yn-1-yl)-1H-indol-3-yl]ethyl}-4-chlorobenzene-1-sulfonamide (4g); N-{2-[6-bromo-2-(pent-4-yn-1-yl)-1H-indol-3-yl]ethyl}-4-chlorobenzene-1-sulfonamide (4h); N-{2-[4-bromo-2-(pent-4-yn-1-yl)-1H-indol-3-yl]ethyl}-4-chlorobenzene-1-sulfonamide (4i); 4-Chloro-N-{2-[5-chloro-7-fluoro-2-(pent-4-yn-1-yl)-1H-indol-3-yl]ethyl}benzene-1-sulfonamide (4j); 4-Chloro-N-{2-[5,7-dichloro-2-(pent-4-yn-1-yl)-1H-indol-3-yl]ethyl}benzene-1-sulfonamide (4k); Benzyl {2-[5-bromo-2-(pent-4-yn-1-yl)-1H-indol-3-yl]ethyl}carbamate (8a); Benzyl {2-[5-bromo-7-fluoro-2-(pent-4-yn-1-yl)-1H-indol-3-yl]ethyl}carbamate (8b); 4-Chloro-16-(4-chlorobenzenesulfonyl)-13-methylidene-8,16-diazatetracyclo[7.4.3.0$^{1,9}$.0$^{2,7}$]hexadeca-2,4,6-triene (5a); 16-(4-Chlorobenzenesulfonyl)-4-methyl-13-methylidene-8,16-diazatetracyclo[7.4.3.0$^{1,9}$.0$^{2,7}$]hexadeca-2,4,6-triene (5b); 16-(4-Chlorobenzenesulfonyl)-4-methoxy-13-methylidene-8,16-diazatetracyclo[7.4.3.0$^{1,9}$.0$^{2,7}$]hexadeca-2,4,6-triene (5c); 16-(4-Chlorobenzenesulfonyl)-4-fluoro-13-methylidene-8,16-diazatetracyclo[7.4.3.0$^{1,9}$.0$^{2,7}$]hexadeca-2,4,6-triene (5d); 16-(4-Chlorobenzenesulfonyl)-13-methylidene-8,16-diazatetracyclo[7.4.3.0$^{1,9}$.0$^{2,7}$]hexadeca-2,4,6-triene (5e); 20-(4-Chlorobenzenesulfonyl)-17-methylidene-12,20-diazapentacyclo[11.4.3.0$^{1,13}$.0$^{2,11}$.0$^{5,10}$]icosa-2,4,6,8,10-pentaene (5f); 6-Bromo-16-(4-chlorobenzenesulfonyl)-13-methylidene-8,16-diazatetracyclo[7.4.3.0$^{1,9}$.0$^{2,7}$]hexadeca-2,4,6-triene (5g); 5-Bromo-16-(4-chlorobenzenesulfonyl)-13-methylidene-8,16-diazatetracyclo[7.4.3.0$^{1,9}$.0$^{2,7}$]hexadeca-2,4,6-triene (5h); 3-Bromo-16-(4-chlorobenzenesulfonyl)-13-methylidene-8,16-diazatetracyclo[7.4.3.0$^{1,9}$.0$^{2,7}$]hexadeca-2,4,6-triene (5i); 4-Chloro-16-(4-chlorobenzenesulfonyl)-6-fluoro-13-methylidene-8,16-diazatetracyclo[7.4.3.0$^{1,9}$.0$^{2,7}$]hexadeca-2,4,6-triene (5j); (4,6-Dichloro-16-(4-chlorobenzenesulfonyl)-13-methylidene-8,16-diazatetracyclo[7.4.3.0$^{1,9}$.0$^{2,7}$]hexadeca-2,4,6-triene (5k); N-(2-(6-Bromo-4-methylene-2,3,4,4a,9,9a-hexahydro-1H-carbazol-4a-yl)ethyl)-4-chlorobenzenesulfonamide (Of1); 4-Chloro-N-[2-(6-chloro-4-methylidene-2,3,4,4a,9,9a-hexahydro-1H-carbazol-4a-yl)ethyl]benzene-1-sulfonamide (6a); 4-Chloro-N-[2-(6-methyl-4-methylidene-2,3,4,4a,9,9a-hexahydro-1H-carbazol-4a-yl)ethyl]benzene-1-sulfonamide (6b); 4-Chloro-N-[2-(6-methoxy-4-methylidene-2,3,4,4a,9,9a-hexahydro-1H-carbazol-4a-yl)ethyl]benzene-1-sulfonamide (6c); 4-Chloro-N-[2-(6-fluoro-4-methylidene-2,3,4,4a,9,9a-hexahydro-1H-carbazol-4a-yl)ethyl]benzene-1-sulfonamide (6d); 4-Chloro-N-[2-(4-methylidene-2,3,4,4a,9,9a-hexahydro-1H-carbazol-4a-yl)ethyl]benzene-1-sulfonamide (6e); 4-Chloro-N-(2-{7-methylidene-6bH,7H,8H,9H,10H,10aH,11H-benzo[a]carbazol-6b-yl}ethyl)benzene-1-sulfonamide (6f); N-[2-(8-bromo-4-methylidene-2,3,4,4a,9,9a-hexahydro-1H-carbazol-4a-yl)ethyl]-4-chlorobenzene-1-sulfonamide (6g); N-[2-(7-bromo-4-methylidene-2,3,4,4a,9,9a-hexahydro-1H-carbazol-4a-yl)ethyl]-4-chlorobenzene-1-sulfonamide (6h); N-(2-((4aS,9aS)-5-bromo-4-methylene-2,3,4,4a,9,9a-hexahydro-1H-carbazol-4a-yl)ethyl)-4-chlorobenzenesulfonamide (6i); 4-Chloro-N-[2-(6-chloro-8-fluoro-4-methylidene-2,3,4,4a,9,9a-hexahydro-1H-carbazol-4a-yl)ethyl]benzene-1-sulfonamide (6j); 4-Chloro-N-[2-(6,8-dichloro-4-methylidene-2,3,4,4a,9,9a-hexahydro-1H-carbazol-4a-yl)ethyl]benzene-1-sulfonamide (6k); N-[2-(6-bromo-8-fluoro-4-methylidene-2,3,4,4a,9,9a-hexahydro-1H-carbazol-4a-yl)ethyl]-4-chlorobenzene-1-sulfonamide (6l); 4-chloro-N-[2-(5,8-dibromo-4-methylidene-2,3,4,4a,9,9a-hexahydro-1H-carbazol-4a-yl)ethyl]benzene-1-sulfonamide; N-[2-(5-bromo-8-fluoro-4-methylidene-2,3,4,4a,9,9a-hexahydro-1H-carbazol-4a-yl)ethyl]-4-chlorobenzene-1-sulfonamide; Benzyl N-[2-(6-bromo-4-methylidene-2,3,4,4a,9,9a-hexahydro-1H-carbazol-4a-yl)ethyl]carbamate (10a); 2-(6-Bromo-4-methylidene-2,3,4,4a,9,9a-hexahydro-1H-carbazol-4a-yl)ethan-1-amine (11a); N-[2-(6-bromo-4-methylidene-2,3,4,4a,9,9a-hexahydro-1H-carbazol-4a-yl)ethyl]-2,2,2-trifluoroacetamide (12a); N-[2-(6-bromo-4-methylidene-2,3,4,4a,9,9a-hexahydro-1H-carbazol-4a-yl)ethyl]pentanamide (12b); N-[2-(6-bromo-4-methylidene-2,3,4,4a,9,9a-hexahydro-1H-carbazol-4a-yl)ethyl]-4-chlorobenzamide (12c); N-[2-(6-bromo-4-methylidene-2,3,4,4a,9,9a-hexahydro-1H-carbazol-4a-yl)ethyl]benzenesulfonamide (12d); N-[2-(6-bromo-4-methylidene-2,3,4,4a,9,9a-hexahydro-1H-carbazol-4a-yl)ethyl]-4-methylbenzene-1-sulfonamide (12e); N-[2-(6-bromo-4-methylidene-2,3,4,4a,9,9a-hexahydro-1H-carbazol-4a-yl)ethyl]-4-fluorobenzene-1-sulfonamide (12f); 4-Bromo-N-[2-(6-bromo-4-methylidene-2,3,4,4a,9,9a-hexahydro-1H-carbazol-4a-yl)ethyl]benzene-1-sulfonamide (12h); N-[2-(6-bromo-4-methylidene-2,3,4,4a,9,9a-hexahydro-1H-carbazol-4a-yl)ethyl]-4-iodobenzene-1-sulfonamide (12i); N-[2-(6-bromo-4-methylidene-2,3,4,4a,9,9a-hexahydro-1H-carbazol-4a-yl)ethyl]-3,4-dichlorobenzene-1-sulfonamide (12j); N-[2-(6-bromo-4-methylidene-2,3,4,4a,9,9a-hexahydro-1H-carbazol-4a-yl)ethyl]-2,4-dichlorobenzene-1-sulfonamide (12k); N-[2-(6-bromo-4-methylidene-2,3,4,4a,9,9a-hexahydro-1H-carbazol-4a-yl)ethyl]-4-cyanobenzene-1-sulfonamide (12l); N-(4-{[2-(6-bromo-4-methylidene-2,3,4,4a,9,9a-hexahydro-1H-carbazol-4a-yl)ethyl]sulfamoyl}phenyl)acetamide (12m); N-[2-(6-bromo-4-methylidene-2,3,4,4a,9,9a-hexahydro-1H-carbazol-4a-yl)ethyl]-2-nitrobenzene-1-sulfonamide (12n); 2-Amino-N-[2-(6-bromo-4-methylidene-2,3,4,4a,9,9a-hexahydro-1H-carbazol-4a-yl)ethyl]benzene-1-sulfonamide (12o); N-[2-(6-bromo-4-methylidene-2,3,4,4a,9,9a-hexahydro-1H-carbazol-4a-yl)ethyl]pyridine-2-sulfonamide (12p); 2,2,2-trichloro ethyl N-[2-(6-bromo-4-methylidene-2,3,4,4a,9,9a-hexahydro-1H-carbazol-4a-yl)ethyl]carbamate; 2-(6-Bromo-8-fluoro-4-methylidene-2,3,4,4a,9,9a-hexahydro-1H-carbazol-4a-yl)ethan-1-amine (11b); Benzyl N-[2-(6-bromo-8-fluoro-4-methylidene-2,3,4,4a,9,9a-hexahydro-1H-carbazol-4a-yl)ethyl]carbamate (10b); N-[2-(6-bromo-8-fluoro-4-methylidene-2,3,4,4a,9,9a-hexahydro-1H-carbazol-4a-yl)ethyl]-4-methoxybenzene-1-sulfonamide (13a); N-[2-(6-bromo-8-fluoro-4-methylidene-2,3,4,4a,9,9a-hexahydro-1H-carbazol-4a-yl)ethyl]-4-methylbenzene-1-sulfonamide (13b); N-[2-(6-bromo-8-fluoro-4-methylidene-2,3,4,4a,9,9a-hexahydro-1H-carbazol-4a-yl)ethyl]-4-fluorobenzene-1-sulfonamide (13c); 4-Bromo-N-[2-(6-bromo-8-fluoro-4-methylidene-2,3,4,4a,9,9a-hexahydro-1H-carbazol-4a-yl)ethyl]benzene-1-sulfonamide (13d); N-[2-(6-bromo-8-fluoro-4-methylidene-2,3,4,4a,9,9a-hexahydro-1H-carbazol-4a-yl)ethyl]-4-iodobenzene-1-sulfonamide (13e); N-[2-(6-bromo-8-fluoro-4-methylidene-2,3,4,4a,9,9a-hexahydro-1H-carbazol-4a-yl)ethyl]-3,4-dichlorobenzene-1-sulfonamide (13f); N-(4-{[2-(6-bromo-8-fluoro-4-methylidene-2,3,4,4a,9,9a-hexahydro-1H-carbazol-4a-yl)ethyl]sulfamoyl}phenyl)acetamide (13g); N-[2-(6-bromo-8-fluoro-4-methylidene-2,3,4,4a,9,9a-hexahydro-1H-carbazol-4a-yl)ethyl]-4-cyanobenzene-1-sulfonamide (13h); N-[2-(6-bromo-8-fluoro-4-methylidene-2,3,4,4a,9,9a-hexahydro-1H-carbazol-4a-yl)ethyl]-4-(trifluoromethyl)benzene-1-sulfonamide (13i); 3,4-Dibromo-N-[2-(6-bromo-8-fluoro-4-methylidene-2,3,4,4a,9,9a-hexahydro-1H-carbazol-4a-yl)ethyl]benzene-1-sulfonamide (13j); 4-Bromo-N-[2-(6-bromo-8-fluoro-4-methylidene-2,3,4,4a,9,9a-hexahydro-1H-carbazol-4a-yl)ethyl]-3-fluorobenzene-1-sulfonamide (13k); 4-Bromo-N-[2-(6-bromo-8-fluoro-4-methylidene-2,3,4,4a,9,9a-hexahydro-1H-carbazol-4a-yl)ethyl]-2-(trifluoromethyl)benzene-1-sulfonamide (13l); 4-Bromo-N-[2-(6-bromo-8-fluoro-4-methylidene-2,3,4,4a,9,9a-hexahydro-1H-carbazol-4a-yl)ethyl]-3-(trifluoromethyl)benzene-1-sulfonamide (13m); 3-bromo-N-[2-(6-bromo-8-fluoro-4-methylidene-2,3,4,4a,9,9a-hexahydro-1H-carbazol-4a-yl)ethyl]-4-(difluoromethoxy)benzene-1-sulfonamide; N-[2-(6-bromo-8-fluoro-4-methylidene-2,3,4,4a,9,9a-hexahydro-1H-carbazol-4a-yl)ethyl]-1-benzo furan-2-sulfonamide; N-[2-(6-bromo-8-fluoro-4-methylidene-2,3,4,4a,9,9a-hexahydro-1H-carbazol-4a-yl)ethyl]-1-methyl-1H-imidazole-4-sulfonamide; N-[2-(6-bromo-8-fluoro-4-methylidene-2,3,4,4a,9,9a-hexahydro-1H-carbazol-4a-yl)ethyl]-6-chloropyridine-3-sulfonamide; 5-bromo-N-[2-(6-bromo-8-fluoro-4-methylidene-2,3,4,4a,9,9a-hexahydro-1H-carbazol-4a-yl)ethyl]pyridine-3-sulfonamide; 4-bromo-N-[2-(6-bromo-8-fluoro-4-methylidene-2,3,4,4a,9,9a-hexahydro-1H-carbazol-4a-yl)ethyl]-2-methylbenzene-1-sulfonamide; 4,5-dibromo-N-[2-(6-bromo-8-fluoro-4-methylidene-2,3,4,4a,9,9a-hexahydro-1H-carbazol-4a-yl)ethyl]thiophene-2-sulfonamide; 4-bromo-N-[2-(6-bromo-8-fluoro-4-methylidene-2,3,4,4a,9,9a-hexahydro-1H-carbazol-4a-yl)ethyl]-3-methylbenzene-1-sulfonamide; 3,4-dichloro-N-[2-(6,8-dichloro-4-methylidene-2,3,4,4a,9,9a-hexahydro-1H-carbazol-4a-yl)ethyl]benzene-1-sulfonamide; N-[2-(6-bromo-2,4a,9,9a-tetrahydro-1H-carbazol-4a-yl)ethyl]-4-chlorobenzene-1-sulfonamide; benzyl N-(2-{2-bromo-4-fluoro-10-methylidene-5H,5aH,6H,7H,8H,9H,10H,10aH-cyclohepta[b]indol-10a-yl}ethyl)carbamate; N-(2-{2-bromo-10-methylidene-5H,5aH,6H,7H,8H,9H,10H,10aH-cyclohepta[b]indol-10a-yl}ethyl)-4-chlorobenzene-1-sulfonamide; N-(2-{2-bromo-4-fluoro-10-methylidene-5H,5aH,6H,7H,8H,9H,10H,10aH-cyclohepta[b]indol-10a-yl}ethyl)-3,4-dichlorobenzene-1-sulfonamide; 4-bromo-N-(2-{2-bromo-4-fluoro-10-methylidene-5H,5aH,6H,7H,8H,9H,10H,10aH-cyclohepta[b]indol-10a-yl}ethyl)benzene-1-sulfonamide; N-[3-(6-bromo-4-methylidene-2,3,4,4a,9,9a-hexahydro-1H-carbazol-4a-yl)propyl]-4-chlorobenzene-1-sulfonamide; N-[2-(6-bromo-4-methylidene-2,3,4,4a,9,9a-hexahydro-1H-carbazol-4a-yl)ethyl]-4-chloro-N-methylbenzene-1-sulfonamide (1d); N-(2-(6-Bromo-9-methyl-4-methylene-2,3,4,4a,9,9a-hexahydro-1H-carbazol-4a-yl)ethyl)-4-chlorobenzenesulfonamide (Of13); N-[2-(6-bromo-4-methylidene-2,3,4,4a,9,9a-hexahydro-1H-carbazol-4a-yl)ethyl]-4-chloro-N-(4-chlorobenzenesulfonyl)benzamide (1f); 2-(6-Bromo-4-methylidene-2,3,4,4a,9,9a-hexahydro-1H-carbazol-4a-yl)-N-(4-chlorobenzenesulfonyl)-S-(4-chlorophenyl)ethane-1-sulfonamido (1e); N-{2-[6-bromo-9-(4-chlorobenzoyl)-4-methylidene-2,3,4,4a,9,9a-hexahydro-1H-carbazol-4a-yl]ethyl}-4-chlorobenzene-1-sulfonamide (1c); N-{2-[6-bromo-9-(4-chlorobenzenesulfonyl)-4-methylidene-2,3,4,4a,9,9a-hexahydro-1H-carbazol-4a-yl]ethyl}-4-chlorobenzene-1-sulfonamide (1b); Benzyl 6-bromo-4a-[2-(4-chlorobenzenesulfonamido)ethyl]-4-methylidene-2,3,4,4a,9,9a-hexahydro-1H-carbazole-9-carboxylate; benzyl N-[2-(6-bromo-4-methylidene-2,3,4,4a,9,9a-hexahydro-1H-carbazol-4a-yl)ethyl]-N-(4-chlorobenzenesulfonyl)carbamate; benzyl 4a-(2-{N-[(benzyloxy)carbonyl]4-chlorobenzenesulfonamido}ethyl)-6-bromo-4-methylidene-2,3,4,4a,9,9a-hexahydro-1H-carbazole-9-carboxylate; N-[2-(6-bromo-4-methylidene-2,3,4,4a,9,9a-hexahydro-1H-carbazol-4a-yl)ethyl]-4-chloro-N-(prop-2-en-1-yl)benzene-1-sulfonamide; N-{2-[6-bromo-4-methylidene-9-(prop-2-en-1-yl)-2,3,4,4a,9,9a-hexahydro-1H-carbazol-4a-yl]ethyl}-4-chlorobenzene-1-sulfonamide; N-{2-[6-bromo-9-(2-{2-[2-(2-hydroxyethoxy)ethoxy]ethoxy}ethyl)-4-methylidene-2,3,4,4a,9,9a-hexahydro-1H-carbazol-4a-yl]ethyl}-4-chlorobenzene-1-sulfonamide.

Composition

The compounds of the invention can be administered to a patient or a subject to achieve a desired physiological effect. Generally, the patient is an animal, typically a mammal, and often a human. The compound can be administered in a variety of forms adapted to the chosen route of administration, i.e., orally or parenterally. Parenteral administration in this respect includes administration by the following routes: intravenous; intramuscular; subcutaneous; intraocular; intrasynovial; transepithelially including transdermal, ophthalmic, sublingual and buccal; topically including ophthalmic, dermal, ocular, rectal and nasal inhalation via insufflation and aerosol; intraperitoneal; and rectal systemic.

The active compound can be orally administered, for example, with an inert diluent or with an assimilable edible carrier, or it can be enclosed in hard or soft shell gelatin capsules, or it can be compressed into tablets, or it can be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparation can contain at least 0.1% of active compound. The percentage of the compositions and preparation can, of course, be varied and can conveniently be between about 1 to about 10% of the weight of the unit. The amount of active compound in such therapeutically useful compositions is such that a suitable dosage will be obtained. Typical compositions or preparations according to the invention are prepared such that an oral dosage unit form contains from about 1 to about 1000 mg of active compound.

The tablets, troches, pills, capsules and the like can also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin can be added or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound can be incorporated into sustained-release preparations and formulation. In addition to the common dosage forms set out above, the compounds of the invention may also be administered by controlled release means and/or delivery devices capable of releasing the active ingredient (prenylation inhibitor) at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. Examples of controlled release pharmaceutical compositions and delivery devices that may be adapted for the administration of the active ingredients of the present invention are described in U.S. Pat. Nos. 3,847,770; 3,916,899; 3,536,809; 3,598,123; 3,630,200; 4,008,719; 4,687,610; 4,769,027; 5,674,533; 5,059,595; 5,591,767; 5,120,548; 5,073,543; 5,639,476; 5,354,566; and 5,733,566, the disclosures of which are hereby incorporated by reference.

Pharmaceutical compositions for use in the methods of the present invention may be prepared by any of the methods of pharmacy, but all methods include the step of bringing the active ingredient into association with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent.

The active compound can also be administered parenterally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It can be stable under the conditions of manufacture and storage and must be preserved against the contaminating action of microorganisms such as bacterial and fungi. The carrier can be a solvent of dispersion medium containing, for example, water, ethanol, polyol (e.g., glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, e.g., sugars or sodium chloride. Prolonged absorption of the injectable compositions of agents delaying absorption, e.g., aluminum monostearate and gelatin.

Sterile injectable solutions are prepared by incorporating the active compound in the required amount in the appropriate solvent with various other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The compounds of the invention can be administered to a mammal alone or in combination with pharmaceutically acceptable carriers, as noted above, the proportion of which is determined by the solubility and chemical nature of the compound, chosen route of administration and standard pharmaceutical practice.

The physician can readily determine the dosage of the present therapeutic agents which will be most suitable for prophylaxis or treatment and it will vary with the form of administration and the particular compound chosen, and also, it will vary with the particular patient under treatment. The physician will generally wish to initiate treatment with small dosages by small increments until the optimum effect under the circumstances is reached. The therapeutic dosage can generally be from about 0.1 to about 1000 mg/day, and preferably from about 10 to about 100 mg/day, or from about 0.1 to about 50 mg/Kg of body weight per day and preferably from about 0.1 to about 20 mg/Kg of body weight per day and can be administered in several different dosage units. Higher dosages, on the order of about 2× to about 4×, may be required for oral administration.

Synthesis

A convergent evolutionary strategy is often utilized by a variety of organisms in Nature for the production of a wide range of bioactive secondary metabolites, such as nonribosomal peptides (e.g., vancomycin), polyketides (e.g., erythromycin A and tetracycline), terpenoids (e.g., taxol), and indoline alkaloids (e.g., vinblastine and ajmaline). This general strategy can be divided into three phases: (1) assembly: simple building blocks are assembled, (2) cyclization: the assemblies are cyclized to afford rigid core structures, and (3) modification: the secondary metabolites are matured for function by a series of modifications, such as oxidation, acylation, glycosylation, and oligomerization.

Some aspects of the invention are based on this common strategy. In one particular aspect of the invention, the present inventor has developed a synthetic process for a polycyclic indoline alkaloid compounds using a chemical reaction strategy instead of using a series of enzymatic reactions in each phase. In one particular embodiment, an alkynyl imine M (FIG. 1), an activating agent $Z^1X$ (1) and an aryl hydrazine (2) were used to produce a wide variety of indoline alkaloid compounds. In some instances, these reagents are combined using a one-pot three-component reaction process that was developed by the present inventor. See Yeo et al., *Tetrahedron*, 2012, 68, 813-818. Based on the present inventor's previous studies on gold catalysis (see, for example, Liu et al., *Org. Lett.*, 2010, 12, 1448-1451 and Noey et al., *J. Org. Chem.*, 2011, 76, 3477-3483), it was envisioned that the resulting two regioisomeric alkynyl indoles (A and B) could undergo gold(I)-catalyzed tandem cyclization reactions to form a fused (Cf) or spiro- (Cs) tetracyclic indoline, respectively. Bandini, M. *Chem. Soc. Rev.*, 2011, 40, 1358-1367. These indoline alkaloid compounds can be further modified, e.g., such as via alkylations of the aniline nitrogen to afford Kf and Ks, or tandem ring-opening reduction-reductive aminations to produce Of and Os series of compounds.

The alkynyl imine building blocks M were readily synthesized by alkylations of cyclic imine 3 with iodides 4 (FIG. 1) under basic conditions followed by desilylation. Only a single purification using basic alumina is required for each alkynyl imine M. Using this general procedure, six alkynyl imines M1-6 were obtained in good yields (60-91%) on multi-gram scale.

These six alkynyl imines were subjected to the one-pot three-component assembly reactions. Since the resulting two regioisomeric indole products were expected to provide distinct ring skeletons upon cyclizations, the reaction conditions were modified and dimethyl formamide (DMF) was used as the solvent to obtain moderate selectivity of regioisomers A and B. As shown in Table 1, under these modified conditions, all six alkynyl imines were converted to the corresponding indoles in moderate to good yields (45-83%). The two regioisomers A and B from each assembly reaction were separable by silica gel chromatography. This assembly reaction showed excellent compatibility with a wide range of activating reagents $Z^1X$, such as sulfonyl chlorides, acyl chlorides, anhydrides and chloroformates. In addition, a variety of aryl hydrazines substituted with either electron-donating groups (e.g., methoxy and methyl) or electron-withdrawing groups (e.g., bromo and chloro) were well tolerated in the reaction conditions. For each alkynyl imine, two different combinations of activating groups and hydrazines were chosen in the assembly reactions. As such, 12 reactions produced 24 highly functionalized alkynyl indoles.

the $Z^1$ groups appeared to migrate to the aniline nitrogens spontaneously after cyclizations, in order to avoid the severe steric interactions.

In order to further modify the cyclized indolines, two general methods were developed. When treated with alkyl triflates, the $Z^1$ groups migrated back to the amine nitrogens and the aniline nitrogens were alkylated to provide Kf and Ks series of compounds. Without being bound by any theory, it is believed that this is likely due to the poor accessibility of the amine nitrogens to the alkylating agents. In these transformations, the ring skeletons of the indolines were maintained. However, the migrations of the $Z^1$ groups caused significant changes of their pharmacological properties (e.g., pKa values). The alkyl triflates are either commercially available, or can be prepared from their corresponding alcohols easily. Alternatively, treatment of the cyclized products Cf and Cs series of compounds with acetic acid and NaBH$_3$CN at 0° C. afforded 24 ring-opened indoline products Of and Os series of compounds, respectively. The hydride was typically added to the iminium ion intermediates from the opposite face of the exo-methylene group (e.g., Of1 and Os5). For the endo-cyclization products (e.g., Cs1 and Cs4), the hydride was added non-selectively. Furthermore, subsequent addition of an aldehyde to the above reaction mixture produced the reductive amination product with a ring-opened indoline bearing an additional alkyl group on the aniline nitrogen. Two different aldehydes were chosen for each cyclized indoline, which provided another 48 ring-opened indoline products.

As discussed above, a concise and systematic synthetic process has been developed by the present inventor. Such a

TABLE 1

One-pot synthesis of alkynyl indoles A and B.

| Entry | M | $Y^1$ | $Y^2$ | $Z^1X$ | $Z^2$ [i.e., $(R^1)_a$] | Yield (%) | A:B |
|---|---|---|---|---|---|---|---|
| 1 | M1 | CH$_2$ | CH$_2$ | $^p$ClPhSO$_2$Cl | 4-Br | 49 | 0.56:1 |
| 2 | M2 | CH$_2$ | CH$_2$CH$_2$ | MeOCOCl | 3,5-diMe | 55 | 1.8:1 |
| 3 | M3 | CH$_2$ | $^o$phenylene | AcCl | $^o$phenylene | 60 | 1.1:1 |
| 4 | M4 | CH$_2$CH$_2$ | CH$_2$ | (CF$_3$CO)$_2$O | 4-Cl | 45 | 0.77:1 |
| 5 | M5 | CH$_2$CH$_2$ | CH$_2$CH$_2$ | $^p$FPhCOCl | 4-OMe | 55 | 1.3:1 |
| 6 | M6 | CH$_2$CH$_2$ | $^o$phenylene | $^p$BrPhSO$_2$Cl | H | 54 | 0.5:1 |
| 7 | M1 | CH$_2$ | CH$_2$ | $^p$ClPhCOCl | 2-OMe | 60 | 1:1 |
| 8 | M2 | CH$_2$ | CH$_2$CH$_2$ | $^p$ClPhSO$_2$Cl | H | 83 | 0.4:1 |
| 9 | M3 | CH$_2$ | $^o$phenylene | MeOCOCl | 4-OMe | 55 | 1.8:1 |
| 10 | M4 | CH$_2$CH$_2$ | CH$_2$ | (CF$_3$CO)$_2$O | 4-Me | 70 | 1:1 |
| 11 | M5 | CH$_2$CH$_2$ | CH$_2$CH$_2$ | $^p$FPhCOCl | $^o$phenylene | 60 | 1.3:1 |
| 12 | M6 | CH$_2$CH$_2$ | $^o$phenylene | $^p$BrPhSO$_2$Cl | 3,5-diMe | 65 | 0.28:1 |

For the cyclization step, the commercially available Ph$_3$PAuNTf$_2$ was used as the catalyst to simplify library production. When subjected to the standard gold catalysis conditions (5 mol % Ph$_3$PAuNTf$_2$, toluene, 50° C.), each of the 24 alkynyl indoles underwent the expected tandem cyclization to produce the corresponding indolines Cf1-12 or Cs1-12 as a single regio- and diastereomer in good to excellent yields (see representative examples in FIG. 1). Nearly all reactions were initiated by the exo-dig cyclizations followed by the intramolecular nucleophilic attack of the iminium ion by the nitrogen nucleophiles. The only exceptions were Cs1 and Cs4, which reacted in an endo-dig fashion due to the severe ring strain of an exo-dig cyclization if they cyclized in the exo mode (i.e., 5-endo-dig cyclization is favored over 4-exo-dig cyclization). Staben et al., *Angew. Chem. Int. Ed.,* 2004, 43, 5350-5352. Hence, more than 10 distinct polycyclic indoline skeletons were constructed under the same reaction condition in this step. In most cases, process enables rapid access to highly functionalized and structurally diverse polycyclic indoline alkaloid compounds. As discussed in detail below, compound Of1, a tricyclic indoline, was found to be a resistance-modifying agent that selectively re-sensitize multi-drug resistant MRSA to β-lactam antibiotics.

Although a particular aspect of the present invention is illustrated in the schemes and examples provided herein, those skilled in the art will recognize that all aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

It is to be understood that the scope of this invention encompasses not only the various isomers which may exist but also the various mixture of isomers which may be formed.

For the compounds that contain one or more chiral centers, the compound can be synthesized enantioselectively or a mixture of enantiomers and/or diastereomers can be prepared and separated. The resolution of the compounds of the present invention, their starting materials and/or the intermediates may be carried out by known procedures, e.g., as described in the four volume compendium *Optical Resolution Procedures for Chemical Compounds*: Optical Resolution Information Center, Manhattan College, Riverdale, N.Y., and in *Enantiomers, Racemates and Resolutions*, Jean Jacques, Andre Collet and Samuel H. Wilen; John Wiley & Sons, Inc., New York, 1981, which are incorporated herein in their entirety. Basically, the resolution of the compounds is based on the differences in the physical properties of diastereomers by attachment, either chemically or enzymatically, of an enantiomerically pure moiety results in forms that are separable by fractional crystallization, distillation or chromatography.

When the compound of the present invention contains an olefin moiety and such olefin moiety can be either cis- or trans-configuration, the compound can be synthesized to produce cis- or trans-olefin, selectively, as the predominant product. Alternatively, the compound containing an olefin moiety can be produced as a mixture of cis- and trans-olefins and separated using known procedures, for example, by chromatography as described in W. K. Chan, et al., *J. Am. Chem. Soc.*, 1974, 96, 3642, which is incorporated herein in its entirety.

Utility

Indoline alkaloid compounds were then screened for the ability to potentiate the activity of methicillin against MRSA. A multi-drug resistant MRSA strain (ATCC: BAA-44) was selected for the initial screening. In addition to methicillin, this MRSA strain is also resistant to many other β-lactams (e.g., amoxicillin/clavulanic acid and cefazolin) as well as erythromycin, tetracycline, ciprofloxacin, among others. The minimum inhibitory concentration (MIC) of methicillin for this MRSA strain was determined to be 128 µg/mL using the standard Clinical Laboratory Standards Institute (CLSI) broth microdilution method. Initial screen was adapted from this standard microdilution assay; however, the Mueller Hinton Broth (MHB) was supplemented with methicillin at ¼ of its MIC value (i.e., 32 µg/mL). To each well, 20 µM of each individual indoline alkaloid was added and the plates were incubated at 37° C. for 16 hrs. Nine indoline alkaloids were identified that reduced the MIC of methicillin for this MRSA strain to 32 µg/mL. Further evaluation of the ability of these nine compounds to potentiate methicillin activity was performed by assessing the MIC of methicillin for MRSA using the standard microdilution method in media supplemented with 20 µM of each alkaloid. It was discovered that Of1 was found to reduce the MIC of methicillin from 128 to 8 µg/mL. To evaluate the anti-proliferative activity of Of1 alone, the standard microdilution assay was performed for Of1 using both MRSA and methicillin-sensitive *S. aureus* (MSSA, ATCC: 25923) and found that its MIC values for both strains are >128 µg/mL (the highest concentration tested). Considering its effective activity (20 µM or ca. 10 µg/mL) to potentiate the activity of methicillin by 16 fold, it is highly likely that it has synergistic effect with methicillin. Since the sensitive range for methicillin against *S. aureus* is defined as ≤8 µg/mL according to the CLSI standard, again without being bound by any theory, it is believed that Of1 re-sensitizes this MRSA strain to methicillin.

Next Of1's potentiation ability was evaluated for several additional antibiotics, such as oxacillin (i.e., the replacement of methicillin), the extended spectrum β-lactam antibiotic amoxicillin/clavulanate, first-generation cephalosporins cephalexin and cefazolin, as well as erythromycin, tetracycline, and ciprofloxin. The results showed that Of1 potentiates all β-lactam antibiotics significantly (8-128 fold), but not antibiotics of other structure classes (Table 2). Although this MRSA strain is not resistant to meropenem, Of1 also showed 16-fold potentiation for meropenem. In addition, Of1 was evaluated in combination with several β-lactam antibiotics in a MSSA strain (ATCC: 25923), where it does not show any significant potentiation effect. Taken together, it appears that Of1 is a resistance-modifying agent specifically for β-lactam antibiotics.

TABLE 2

Of1 selectively potentiates β-lactam antibiotics in a multi-drug resistant MRSA strain (ATCC BAA-44).[a]

| Compound | MIC (µg/ml) | MIC (+Of1)[a] (µg/ml) | fold of potentiation | sensitive range[b] (µg/ml) |
|---|---|---|---|---|
| Of1 | >128 | — | — | — |
| methicillin | 128 | 8 | 16 | ≤8 |
| oxacillin | 64 | 0.5 | 128 | ≤2 |
| amoxicillin/clavulanate | 32/16 | 4/2 | 8 | ≤4/2 |
| meropenem | 4 | 0.25 | 16 | ≤4 |
| imipenem | 0.5 | .0625 | 8 | |
| cephalexin | 256 | 16 | 16 | |
| cefazolin | 128 | 4 | 32 | ≤8 |
| ciprofloxacin | 8 | 8 | 1 | ≤1 |
| tetracycline | 64 | 64 | 1 | ≤4 |
| erythromycin | >256 | >256 | — | ≤0.5 |

[a]MIC value in the presence of 20 µM Of1;
[b]values obtained from Clinical Laboratory Standards Institute (CLSI) Performance Standards for Antimicrobial Testing; 17th informational supplement.

The minimum concentrations of Of1 required to re-sensitize MRSA were also determined for three common β-lactam antibiotics: oxacillin, amoxicillin/clavulanate, and cefazolin. A modified broth microdilution assay was employed by incubating MRSA (ATCC: BAA-44) with Of1 in 2-fold series dilution in the presence of individual antibiotics at the highest sensitive concentration at 37° C. overnight. As shown in Table 3, Of1 re-sensitizes MRSA to all three antibiotics, while their minimum re-sensitizing concentrations (MRCs) of Of1 vary and are dependent on the antibiotic used. This is probably due to both the different sensitive concentration defined for each antibiotic and the different level of resistance of MRSA to various antibiotics. The MRC values were also determined for another three MRSA strains. The strain 33592 (ATCC) behaves similarly to BAA-44, and their MRCs for the three antibiotics tested are all 4 µg/mL. ATCC BAA-1683 is not resistant to cefazolin, but resistant to both oxacillin and amoxicillin/clavulanate. The MRC for oxacillin is found to be >32 µg/mL (the highest concentration tested), and the MRC for amoxicillin/clavulanate is 4 µg/mL, similar to the other two strains. ATCC 700789 is particularly interesting, because it is also known as a vancomycin intermediate resistant *S. aureus* (VISA). Results showed that Of1 is able to re-sensitize this VISA strain to amoxicillin/clavulanate at 4 µg/mL. Furthermore, the mammalian toxicity of Of1 was evaluated using human liver hepatocellular carcinoma HepG2 cell line in CellTiter Glo™ mammalian viability assay (Promega). Of1 showed no observable cytotoxic effect against HepG2 cells at 4 µg/mL (the effective concentration) and its half growth inhibitory concentration (GI$_{50}$) is approximately 8.9 µg/mL.

TABLE 3

Minimum concentrations of Of1 to re-sensitize MRSA to beta-lactam antibiotics.[a]

| Beta-lactam antibiotic | BAA-44 | 33592 | 700789 | BAA-1683 |
|---|---|---|---|---|
| oxacillin | 2 | 4 | >64 | >32 |
| amoxicillin/clavulanate | 4 | 4 | 4 | 4 |
| cefazolin | 4 | 4 | —[b] | —[b] |

[a]strain names are all ATCC numbers;
[b]this strain is not resistant to the antibiotic indicated.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

All NMR data were obtained using CDCl$_3$, unless otherwise noted.

Minimal Resensitizing Concentration (MRC) Determination.

MRC screens were performed as follows: antibiotic MIC values where *S. aureus* is considered susceptible were determined from the CLSI handbook supplement. Analogs of Of1 were diluted to 5 mg/ml in DMSO. Antibiotic was prepared at twice the intended final concentration in Mueller Hinton Broth (MHB). For amoxicillin/clavulanic acid, the initial concentration was 8/4 µg/ml, for meropenem 8 µg/ml and for cefazolin 16 µg/ml. 50 µl of the antibiotic containing media was added to each well of 96 well plates and 100 µl was added to the top row. 1.28 µl of 5 mg/ml alkaloid solution was added to the top row of each plate to afford a concentration of 64 µg/ml in the top row of each plate and two fold serial dilutions were performed down the columns. Once the plates were prepared, a day culture of MRSA was diluted to OD$_{600}$ 0.002 and 50 µl was added to each well. The final concentration of MRSA was OD$_{600}$ 0.001, the final concentration of amoxicillin/clavulanic acid was 4/2 µg/ml, the final concentration of meropenem was 4 µg/ml the final concentration of cefazolin was 8 µg/ml, and the highest concentration of Of1 analog tested was 32 µg/ml. Plates were incubated overnight at 37° C. with shaking. The MRC value was determined as the concentration of Of1 analog in the presence of antibiotic at which there was no observable overnight growth.

Microdilution Tests for Minimal Inhibitory Concentration (MIC) Determination.

The minimal inhibitory concentrations (MICs) of active Of1 analogs were determined by the broth microdilution method detailed in the Clinical and Laboratory Standards Institute handbook. All antimicrobial compounds were purchased from Sigma-Aldrich. The growth media used for all MIC experiments was Mueller Hinton Broth (MHB) purchased from HIMEDIA through VWR (cat: 95039-356). The inoculum was prepared by diluting a bacterial day culture (OD$_{600}$ 0.15-0.4) to OD$_{600}$ 0.002. This dilution was further diluted two fold when added to 96 well microplates (USA Scientific CytoOne 96-well TC plate, cat: CC7682-7596) for a final inoculum concentration of OD$_{600}$ 0.001. All plates were incubated at 37° C. with shaking for 18 hours (overnight) before results were interpreted.

Resistance Modifying Agent (RMA) Screen.

The MRSA strain ATCC BAA-44 was used to screen the indole alkaloid library for RMA activity. 96-well assay plates were prepared containing 50 µl MHB supplemented with 64 µg/ml of methicillin, ½ of its MIC against BAA-44. 500 nl of each indoline alkaloid (4 mM in DMSO) was pinned to the assay plate using the CyBi-Well 96-channel simultaneous pipettor (Cybio). These plates were inoculated with 50 µl MRSA BAA-44 diluted to OD$_{600}$ 0.002. The final concentration of methicillin for the screen was 32 µg/ml (¼ of the methicillin MIC), the final concentration of each alkaloid was 20 µM, and the final inoculum concentration was OD$_{600}$ 0.001. All plates were incubated at 37° C. with shaking for 18 hours before results were interpreted.

Determination of MIC in the Presence of Of1.

The MRSA strain ATCC BAA-44 and the methicillin-sensitive *S. aureus* (MSSA) strain ATCC 25923 were used to determine the MIC values of various antimicrobial compounds in the presence of 20 µM Of1. The experiment was conducted similarly to the CLSI MIC determination described previously; however, MHB was supplemented with 40 µM Of1 prior to set up and inoculation. The final concentration of Of1 after inoculation with BAA-44 was 20 µM.

Microdilution Checkerboard Tests for Drug Synergy.

Checkerboard assays were performed follows: antibiotics were diluted down the columns of a 96-well microplate, while 13d was diluted across the rows. Plates were prepared containing concentrations of antibiotics and 13d two fold higher than the intended final concentrations and were prepared in duplicate. All antimicrobial compounds were purchased from Sigma-Aldrich. The growth media was Mueller Hinton Broth (MHB) purchased from HIMEDIA through VWR (cat: 95039-356). The inoculum was prepared by diluting a bacterial day culture (OD$_{600}$ 0.15-0.4) to OD$_{600}$ 0.002. This dilution was further diluted two fold when added to 96 well microplates (USA Scientific CytoOne 96-well TC plate, cat: CC7682-7596) for a final inoculum concentration of OD$_{600}$ 0.001. All plates were incubated at 37° C. with shaking for 18 hours before results were interpreted.

Mammalian Cytotoxicity of Of1 Analogs in HeLa Cells.

To evaluate the cytotoxicity of Of1 in mammalian cells, a cell viability assay was carried out using CellTiter-Glo luminescent cell viability assay kit (Promega). Human cervixcal adenocarcinoma HeLa cells were seeded on white, cell-culture treated 96-well plates (Corning: 3917) with Dulbecco's modified Eagle's medium (DMEM) supplemented with 10% fetal calf serum (FCS), 1% penicillin/streptomycin, at the densities of 20,000 cells/well. The medium volume for each well was 100 µL. Cells were incubated at 37° C. in 5% CO$_2$/95% air for 16 hours. The medium was removed from each well and replaced with 99 µL of warmed fresh medium. To each well, 1 µL of Of1 analog was added in DMSO to final concentrations of 0.5-32 µg/mL. Each series was performed in triplicate. After incubation at 37° C. for another 24 hours, the plates were equilibrated to room temperature for 30 minutes. 100 µL of CellTiter-Glo reagent (Promega) was added to each well and mixed for 2 minutes on an orbital shaker. The plate was incubated at room temperature for another 10 minutes to stabilize luminescent signal. The luminescence of each sample was recorded in an Envision Multilabel Plate Reader (Perkin Elmer).

Hemolytic Activity Assay.

8 mL of freshly drawn, heparin stabilized, human blood was centrifuged at 3500 rpm for 5 minutes. The supernatant was removed and the human red blood cells (hRBCs) were washed with 8 mL D-PBS 3 times or until supernatant was clear. hRBCs were then re-suspended in 80 mL D-PBS. This was further diluted in D-PBS to a final concentration of 1% of the original pellet volume. 13d was dissolved in DMSO was and to 1 ml samples of the hRBC solution to final concentrations of 64, 16 and 4 μg/ml. A 1% Triton X-100 sample was used as the positive control, this was considered to produce 100% hemolysis, DMSO alone was used as the negative control. The mixtures were vortexed gently and incubated at 37° C. for 1 hr with shaking. The mixtures were then centrifuged at 3,000 rpm for 10 minutes. 50 μL of supernatant from each sample was transferred to a well of a sterile 96-well plate containing 50 μL of water. Presence of hemoglobin was measured by absorbance at 415 nm and percent hemolysis was calculated using the following equation:

$$\% \text{ Hemolysis} = [(A_{415,13d} - A_{415,DMSO}) / (A_{415,complete\ hemolysis} - A_{415,DMSO})] \times 100$$

Each condition was assayed in triplicate. The assay was performed within 3 hours of the blood draw.

General Protocol for the Preparation of Alkynyl Imines M1-6.

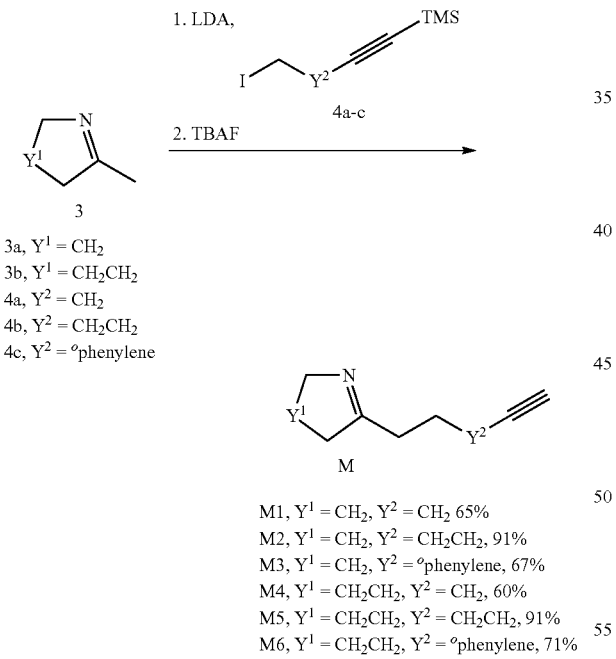

M1, $Y^1 = CH_2$, $Y^2 = CH_2$ 65%
M2, $Y^1 = CH_2$, $Y^2 = CH_2CH_2$, 91%
M3, $Y^1 = CH_2$, $Y^2 = {}^o$phenylene, 67%
M4, $Y^1 = CH_2CH_2$, $Y^2 = CH_2$, 60%
M5, $Y^1 = CH_2CH_2$, $Y^2 = CH_2CH_2$, 91%
M6, $Y^1 = CH_2CH_2$, $Y^2 = {}^o$phenylene, 71%

To a solution of freshly distilled diisopropylamine (6.5 mmol, 0.93 mL) in anhydrous THF (10 mL) at 0° C. was added slowly a solution of ⁿbutyllithium (1.6 M in hexanes, 3.75 mL, 6.0 mmol, 1.2 equiv.) under argon atmosphere. After 20 min this solution was cooled to −78° C. and a solution of cyclic imine 3 (5.0 mmol) in anhydrous THF (5.0 mL) was added dropwise. The resulting mixture was then stirred at −78° C. for 2 h. A solution of alkyl iodide 4 (6.0 mmol, 1.2 equiv.) in anhydrous THF (5.0 mL) was added slowly, after which the reaction mixture was slowly warmed to 23° C. and stirred overnight. An aqueous solution of sodium hydroxide (0.5 M, 20 mL) was then added and the aqueous layer was extracted with ether. The combined organic phases were washed with a solution of sodium hydroxide (0.5 M), dried over anhydrous $Na_2SO_4$. After filtration, the solvent was removed in vacuo to give the residue, which was used in the next step without further purification.

The residue obtained in the previous step was then dissolved in anhydrous THF (10.0 mL) and cooled to 0° C. Tetrabutylammonium fluoride (1.0 M in THF, 6.0 mL, 6.0 mmol, 1.2 equiv.) was added dropwise to the above solution, and the resulting mixture was stirred for 10 min at 0° C. The reaction was terminated by the addition of water (20.0 mL), and the aqueous layer was extracted with ethyl acetate. The combined organic layers were washed with a solution of sodium hydroxide (0.5 M), dried over anhydrous $Na_2SO_4$, and concentrated in vacuo to produce a crude oil, which was purified by column chromatography on basic aluminum oxide (hexanes/ethyl acetate=10:1) to afford M as a yellowish to red oil.

General Protocol or the One-Pot Three-Component Indole Synthesis.

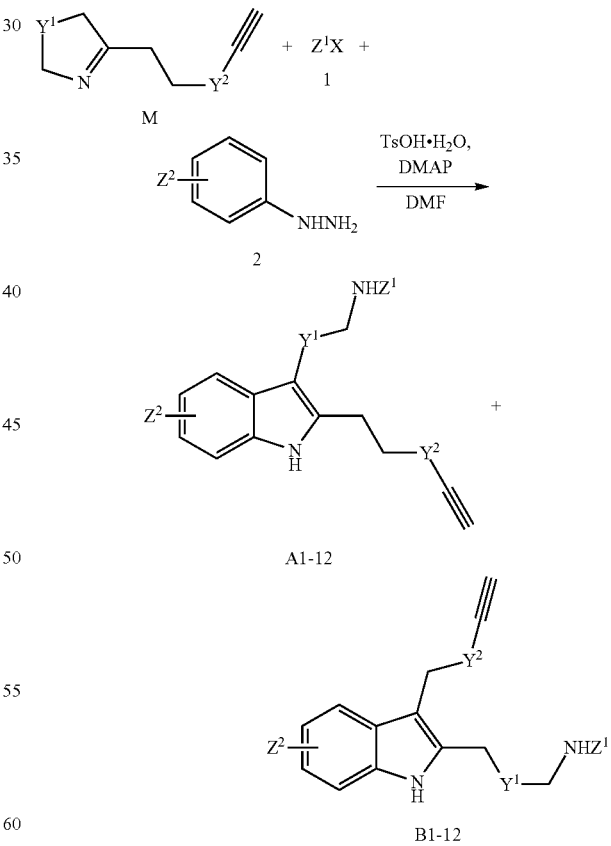

Activating agent 1 (e.g., 4-Chlorobenzenesulfonyl chloride) (1.2 mmol, 1.2 equiv.) was added to a solution of 4-dimethylaminopyridine (DMAP) (1.2 mmol, 1.2 equiv.) in anhydrous DMF (1.0 mL) at 0° C. The reaction was stirred at 23° C. for 30 min. A solution of the alkynyl imine M (1.0 mmol) in anhydrous DMF (1.0 mL) was added and the reaction was stirred at the same temperature for 2-12 h (2 h for 5-membered ring imine and 12 h for 6-membered ring imine). p-Toluenesulfonic acid monohydrate or methanesulfonic acid (3.0 mmol, 3.0 equiv.) was next added to the above mixture at 0° C. The reaction was then stirred at 23° C. for 2 h. Arylhydrazine 2 (1.5 mmol, 1.5 equiv.) was added and stirred for an addition 1 h at 23° C. The reaction was then heated to 50-120° C. (50° C. for electron rich arylhydrazines and 120° C. for electron poor arylhydrazines) for 24 h. The reaction was cooled down to room temperature. The residue was then dissolved in ethyl acetate and washed with brine and a saturated aqueous solution of NaHCO$_3$. The combined organic layers were dried over anhydrous Na$_2$SO$_4$, filtered and concentrated in vacuo to give a crude product, which was purified by column chromatography on silica gel to give the indoles A and B.

General Protocol for Gold (I)-Catalyzed Tandem Cyclization.

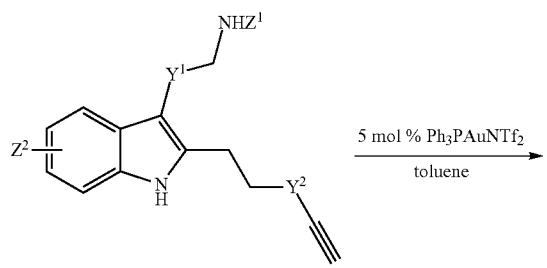

A1-12

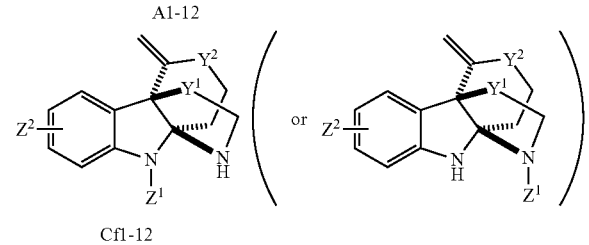

Cf1-12 or

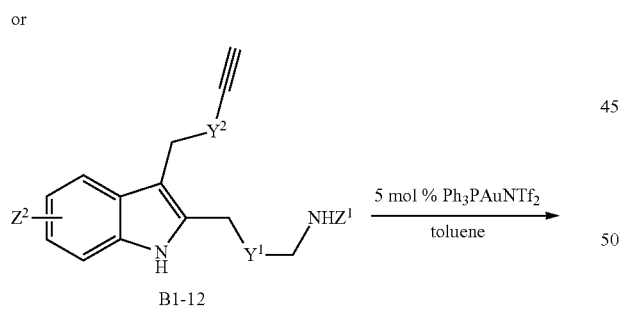

B1-12

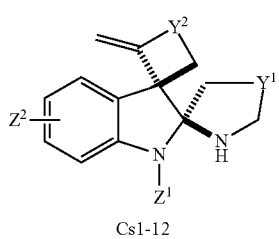

Cs1-12

To a suspension of Ph$_3$PAuNTf$_2$ (as the 2:1 toluene adduct) (7.9 mg, 5.0 μmmol, 0.05 equiv.) in anhydrous toluene was added a solution of indole A or B (0.1 mmol) in anhydrous toluene (2.0 mL). The suspension was heated to 50° C. until TLC showed that there was no starting material left (1-12 h)$^{S1}$ under argon atmosphere. The reaction mixture was then filtered through a short pad of silica gel. The filtrate was concentrated in vacuo and the residue was purified by column chromatography on silica gel to afford tetracyclic indoline product Cf or Cs.

General Protocol for the Alkylation of Indoline Alkaloids.

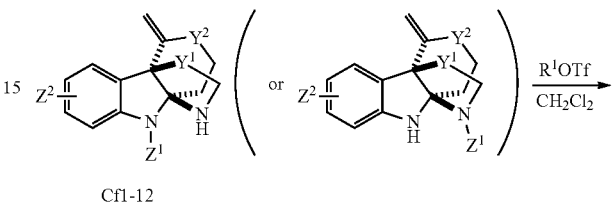

Cf1-12

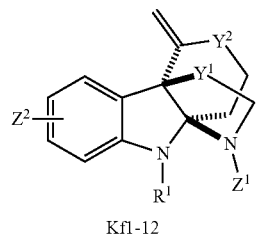

Kf1-12 or

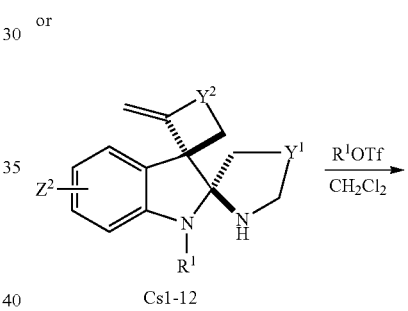

Cs1-12

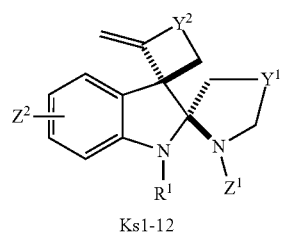

Ks1-12

To a solution of the tetracyclic indoline Cf or Cs (0.01 mmol) in anhydrous dichloromethane (0.2 mL) was added R$^1$OTf (0.1 mmol, 10.0 equiv.)$^{S2}$ at 0° C. The resulting mixture was stirred at 0° C. to 23° C. for 2-12 h under argon atmosphere. The solvent was removed in vacuo to give a residue, which was dissolved in ethyl acetate and the organic layers were washed with an aqueous solution of NaHCO$_3$.$^{S3}$ The combined organic layers were dried over anhydrous Na$_2$SO$_4$, filtered, and concentrated in vacuo to give a crude product, which was purified by column chromatography on silica gel to give the product Kf or Ks.

General Protocol or the Ring-Opening Reduction-Reductive Aminations.

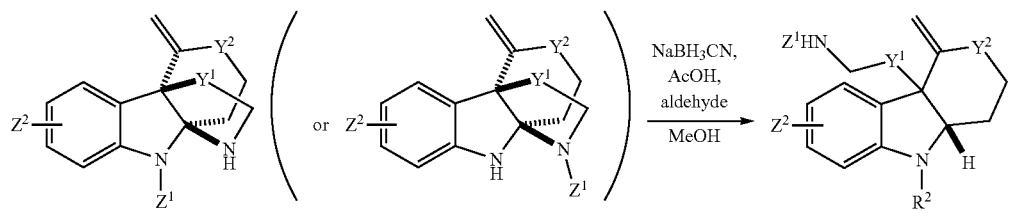

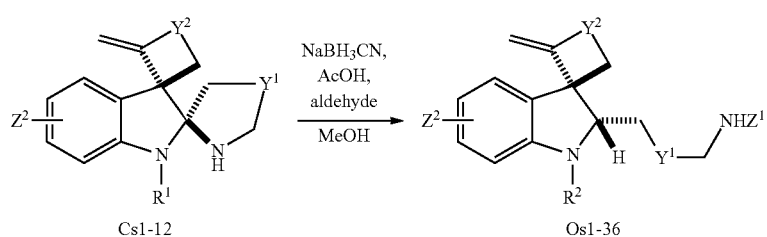

To a solution of the tetracyclic indoline Cf or Cs (0.1 mmol) in anhydrous methanol (0.5 mL) was added acetic acid (0.2 mmol, 12 μL, 2.0 equiv.) and sodium cyanoborohydride (0.4 mmol, 31.5 mg, 4.0 equiv.). After 30 min, aldehyde (0.12 mmol, 1.2 equiv.) was added. The resulting mixture was stirred at 23° C. for 2-12 h. The solvent was removed in vacuo to give a residue, which was dissolved in ethyl acetate and the organic layers were washed with a saturated aqueous solution of NaHCO$_3$. The combined organic layers were dried over anhydrous Na$_2$SO$_4$, filtered and concentrated in vacuo to give a crude product, which was purified by column chromatography on silica gel to afford the product Of or Os.

For the cyclization of B3, B5, B6, B9 and B12, only room temperature was required. Alkyl triflates other than MeOTf and EtOTf were prepared in situ by following the literature protocols. For the literature protocols, see (a). Vedejs, E., Engler, D. A. & Mullins, M. J. *J. Org. Chem.* 42, 3109-3113 (1977). (b). Núñez, A., Cuadro, A. M., Alvarez-Builla, J. & Vaquero, J. *J. Org. Lett.* 6, 4125-4127 (2004). S3. For some electron rich substrates (e.g., Kf2, Kf10, Kf11, Ks2, Ks5, Ks6, Ks7, Ks10), the corresponding triflate salts of the products were obtained and characterized. S4. No aldehyde was added when $R^2$ was proton.

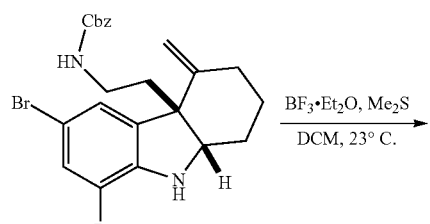

-continued

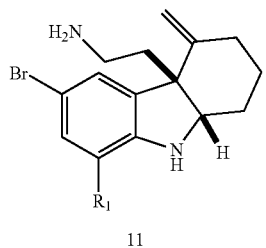

General Protocol for the Removal of Cbz Group.

To a solution of substrate 10 (1.0 equiv.) in dry dichloromethane was added boron trifluoride diethyl etherate (5.0 equiv.), dimethyl sulfide (10.0 equiv.) drop-wise at 23° C. The resulting mixture was stirred at this temperature for 2 h. After that TLC showed that there was no starting material left, the mixture was poured into water and 10% aqueous ammonium hydroxide and extracted with chloroform for 3 times. The combined extracts were washed with water then brine, and dried over anhydrous Na$_2$SO$_4$, filtered and concentrated in vacuo to give a crude product, which was purified by column chromatography on silica gel to afford the product 11.

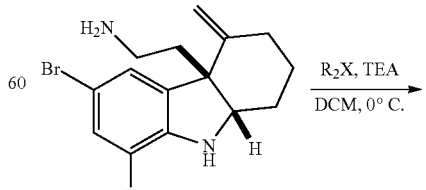

-continued

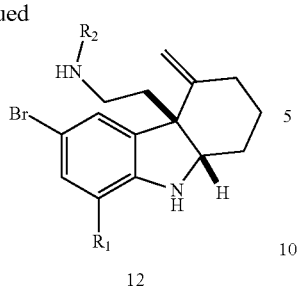

12

General protocol for the modification of free amine.

To a solution of substrate 11 (1.0 equiv.) in dry dichloromethane was added triethyl amine (3.0 equiv.), corresponding sulfonyl chloride or acetyl chloride (1.2 equiv.) drop-wise at 0° C. The resulting mixture was stirred at this temperature for 15 min. The reaction was quenched by aqueous sodium bicarbonate and extracted with dichloromethane for 3 times. The combined extracts were washed with water then brine, and dried over anhydrous $Na_2SO_4$, filtered and concentrated in vacuo to give a crude product, which was purified by column chromatography on silica gel to afford the product 12.

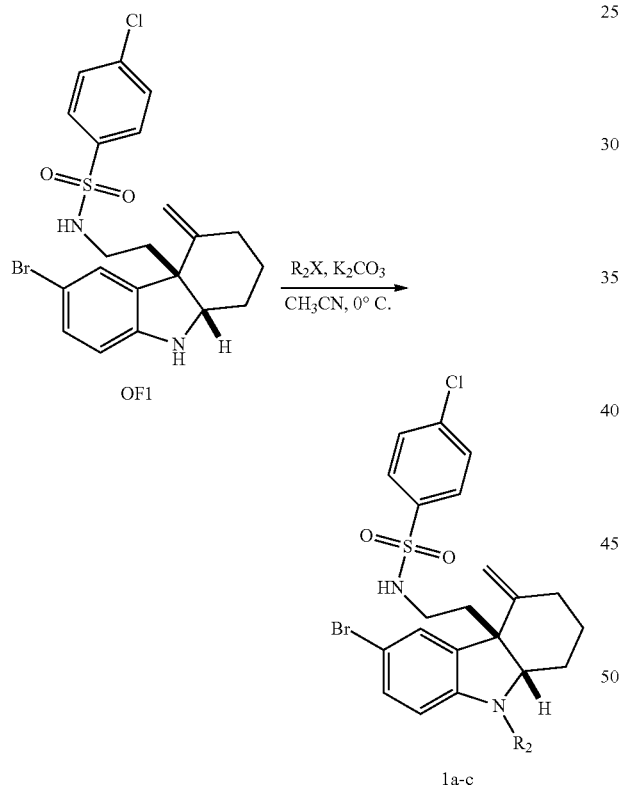

1a-c

General Protocol for the Modification of Of1's Indoline Amine.

To a solution of substrate Of1 (0.1 mmol) in dry acetonitrile was added potassium carbonate (0.3 mmol), corresponding sulfonyl chloride or acetyl chloride (0.12 mmol) drop-wise at 0° C. The resulting mixture was stirred at this temperature for 15 min. The reaction was quenched by aqueous sodium bicarbonate and extracted with dichloromethane for 3 times. The combined extracts were washed with water then brine, and dried over anhydrous $Na_2SO_4$, filtered and concentrated in vacuo to give a crude product, which was purified by column chromatography on silica gel to afford the products 1a-c.

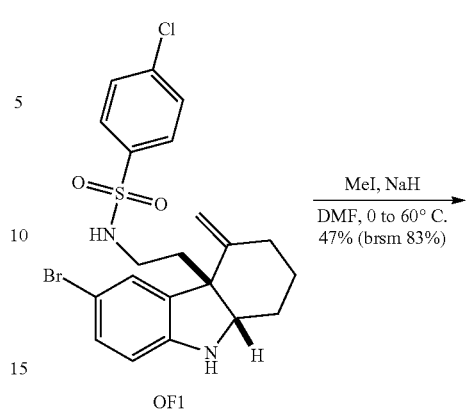

1d

Protocol for the Synthesis of 1d.

To a solution of sodium hydride (0.7 mg, 0.02 mmol) in dry N, N-dimethylformamide was added Of1 (6.0 mg, 0.012 mmol) drop-wise at 0° C. After 15 min, iodomethane (3.9 μL, 0.06 mmol) was added drop-wise at 0° C. The resulting mixture was stirred at this temperature for 15 min, and then warmed up to 60° C. for 30 min. The reaction was quenched by aqueous ammonium chloride and extracted with ethyl acetate for 3 times. The combined extracts were washed with water then brine, and dried over anhydrous $Na_2SO_4$, filtered and concentrated in vacuo to give a crude product, which was purified by column chromatography on silica gel to afford the products 1d.

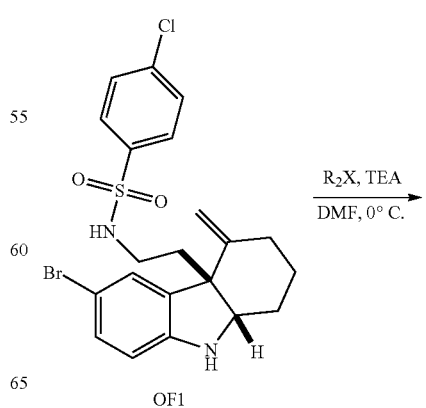

OF1

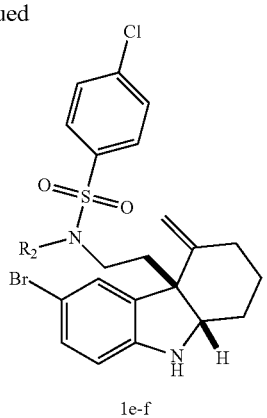

1e-f

General Protocol for the Modification of Of1's Side Chain Amine.

To a solution of substrate Of1 (1.0 equiv.) in dry dichloromethane was added triethyl amine (3.0 equiv.), corresponding sulfonyl chloride or acetyl chloride (1.2 equiv.) drop-wise at 0° C. The resulting mixture was stirred at this temperature for 15 min. The reaction was quenched by aqueous sodium bicarbonate and extracted with dichloromethane 3 times. The combined extracts were washed with water then brine, and dried over anhydrous Na$_2$SO$_4$, filtered and concentrated in vacuo to give a crude product, which was purified by column chromatography on silica gel to afford the products 1e or 1f.

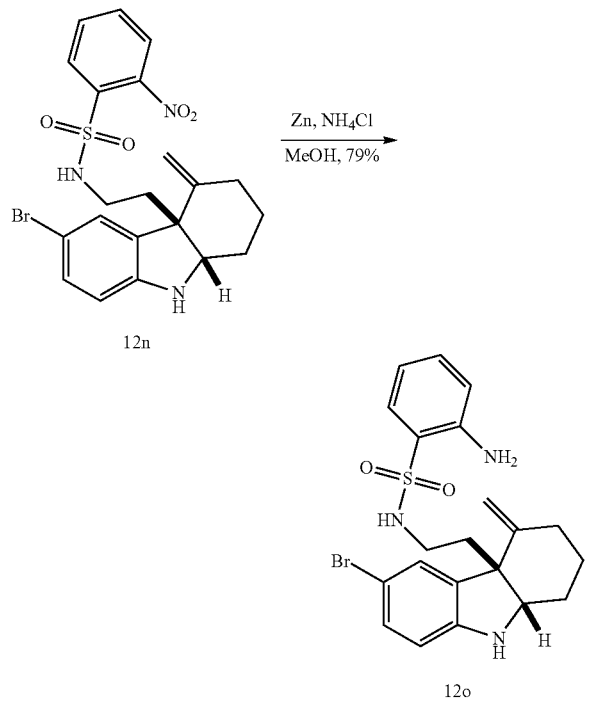

Protocol for the Reduction of 12o.

To a solution of substrate 12n (4.0 mg, 0.008 mmol) in methanol was added a solution of ammonium chloride (8.7 mg, 0.162 mmol) in water and zinc dust (5.3 mg, 0.08 mmol) at room temperature. The resulting mixture was stirred for 6 h then filtered. The filtrate was removed under reduce pressure and the residue was diluted with 2N sodium hydroxide and extracted with ethyl acetate for 3 times. The combined extracts were washed with water then brine, and dried over anhydrous Na$_2$SO$_4$, filtered and concentrated in vacuo to give a crude product, which was purified by column chromatography on silica gel to afford the products 12o.

Compound Characterization Data:

Using the methods described herein, the following compounds were also prepared: 4-Chloro-N-{2-[5-chloro-2-(pent-4-yn-1-yl)-1H-indol-3-yl]ethyl}benzene-1-sulfonamide (4a): $^1$H NMR: δ 7.99 (s, 1H), 7.66 (d, J=8.6 Hz, 2H), 7.41 (d, J=8.6 Hz, 2H), 7.24 (d, J=2.0 Hz, 1H), 7.21 (d, J=8.5 Hz, 1H), 7.10 (dd, J=8.6, 2.0 Hz, 1H), 4.40 (t, J=6.2 Hz, 1H), 3.25 (q, J=6.5 Hz, 2H), 2.89 (dt, J=16.4, 7.1 Hz, 4H), 2.23 (td, J=6.8, 2.7 Hz, 2H), 2.09 (t, J=2.6 Hz, 1H), 1.85 (p, J=7.1 Hz, 2H); $^{13}$C NMR: δ 139.1, 138.1, 137.4, 133.7, 129.3, 129.0, 128.3, 125.3, 121.8, 117.3, 111.6, 107.1, 83.5, 69.9, 43.0, 28.2, 24.5, 24.5, 17.7; m/z: Calcd for C$_{21}$H$_{21}$Cl$_2$N$_2$O$_2$S [M+H]$^+$ 435.0695. Found 435.0694; IR: 3377, 3297, 2924, 2854, 2359, 1575, 1475, 1325, 1160, 1094, 828 cm$^{-1}$. 4-Chloro-N-{2-[5-methyl-2-(pent-4-yn-1-yl)-1H-indol-3-yl]ethyl}benzene-1-sulfonamide (4b): $^1$H NMR: δ 7.88 (s, 1H), 7.63 (d, J=8.8 Hz, 2H), 7.37 (d, J=8.7 Hz, 2H), 7.18 (d, J=8.2 Hz, 1H), 7.09 (s, 1H), 6.98 (dd, J=8.3, 1.7 Hz, 1H), 4.50 (t, J=6.1 Hz, 1H), 3.25 (q, J=6.5 Hz, 2H), 2.92 (t, J=6.7 Hz, 2H), 2.83 (t, J=7.4 Hz, 2H), 2.42 (s, 3H), 2.20 (td, J=6.8, 2.7 Hz, 2H), 2.08 (t, J=2.5 Hz, 1H), 1.85-1.80 (m, 2H); $^{13}$C NMR: δ 138.9, 138.2, 135.9, 133.7, 129.2, 128.9, 128.4, 128.1, 123.2, 117.5, 110.3, 106.7, 83.7, 69.7, 43.2, 28.3, 24.5, 24.5, 21.5, 17.7; m/z: Calcd for C$_{22}$H$_{24}$ClN$_2$O$_2$S [M+H]$^+$ 415.1242. Found 415.1249; IR: 3394, 3298, 2937, 2860, 1587, 1477, 1456, 1326, 1161, 1093, 828, 754, 619 cm$^{-1}$. 4-Chloro-N-{2-[5-methoxy-2-(pent-4-yn-1-yl)-1H-indol-3-yl]ethyl}benzene-1-sulfonamide (4c): $^1$H NMR: δ 7.97-7.90 (brm, 1H), 7.64 (d, J=8.7 Hz, 2H), 7.37 (d, J=8.4 Hz, 2H), 7.17 (d, J=8.5 Hz, 1H), 6.86-6.76 (m, 2H), 4.71-4.59 (brm, 1H), 3.82 (s, 3H), 3.22 (q, J=6.6 Hz, 2H), 2.92 (t, J=6.8 Hz, 2H), 2.81 (t, J=7.5 Hz, 2H), 2.19 (td, J=6.9, 2.8 Hz, 2H), 2.07 (s, 1H), 1.81 (p, J=7.2 Hz, 2H); $^{13}$C NMR: δ 154.1, 138.9, 138.2, 136.6, 130.5, 129.2, 128.4, 128.4, 111.3, 111.2, 107.1, 100.3, 83.7, 69.7, 55.9, 43.2, 28.3, 24.6, 24.6, 17.7; m/z: Calcd for C$_{22}$H$_{24}$ClN$_2$O$_2$S [M+H]$^+$ 431.1191. Found 431.1194; IR: 3395, 3296, 2940, 2833, 1683, 1500, 1455, 1434, 1396, 1327, 1217, 1159, 1095, 1030, 1014, 829, 737 cm$^{-1}$. 4-Chloro-N-{2-[5-fluoro-2-(pent-4-yn-1-yl)-1H-indol-3-yl]ethyl}benzene-1-sulfonamide (4d): $^1$H NMR: δ 8.01 (s, 1H), 7.66 (d, J=8.2 Hz, 2H), 7.39 (d, J=8.2 Hz, 2H), 7.19 (dd, J=8.7, 4.3 Hz, 1H), 6.94 (dd, J=9.5, 2.5 Hz, 1H), 6.88 (td, J=9.0, 2.5 Hz, 1H), 4.56 (t, J=6.3 Hz, 1H), 3.23 (q, J=6.6 Hz, 2H), 2.91-2.83 (m, 4H), 2.21 (dt, J=6.9, 3.8 Hz, 2H), 2.08 (d, J=2.6 Hz, 1H), 1.84 (t, J=7.2 Hz, 2H); $^{13}$C NMR: δ 159.3, 156.2, 139.1, 138.2, 137.7, 131.8, 129.3, 128.3, 113.1, 111.3, 111.1, 109.9, 109.6, 107.5, 107.5, 103.0, 102.7, 83.5, 69.8, 43.1, 28.2, 24.6, 24.6, 17.7; m/z: Calcd for C$_{21}$H$_{21}$ClFN$_2$O$_2$S [M+H]$^+$ 419.0991. Found 419.0995; IR: 3381, 3300, 2922, 2851, 1631, 1586, 1511, 1486, 1455, 1326, 1160, 1094, 827, 616 cm$^{-1}$. 4-Chloro-N-{2-[2-(pent-4-yn-1-yl)-1H-indol-3-yl]ethyl}benzene-1-sulfonamide (4e): $^1$H NMR: δ 7.98 (brs, 1H), 7.64 (d, J=8.5 Hz, 2H), 7.38 (d, J=8.5 Hz, 2H), 7.34 (d, J=7.9 Hz, 1H), 7.30 (d, J=8.1 Hz, 1H), 7.16 (t, J=7.6 Hz, 1H), 7.06 (t, J=7.5 Hz, 1H), 4.50 (t, J=6.2 Hz, 1H), 3.26 (q, J=6.6 Hz, 2H), 2.95 (t, J=6.8 Hz, 2H), 2.86 (t, J=7.4 Hz, 2H), 2.22 (td, J=6.9, 2.8 Hz, 2H), 2.08 (s, 1H), 1.84 (p, J=7.1 Hz, 2H).; $^{13}$C NMR: δ 138.9, 138.2, 135.7, 135.4, 129.2, 128.4, 127.9, 121.7, 119.6, 117.8, 110.6, 107.2, 83.6, 69.7, 43.3, 28.3, 24.6, 24.5, 17.7; m/z: Calcd for C$_{21}$H$_{22}$ClN$_2$O$_2$S [M+H]$^+$ 401.1085. Found 401.1068; IR: 3395, 3299, 2924, 2853, 1678, 1586, 1477, 1396, 1327, 1160, 1094, 893, 828 cm$^{-1}$. 4-Chloro-N-{2-[2-(pent-4-yn-1-yl)-1H-benzo[g]indol-3-yl]ethyl}benzene-1-sulfonamide (4o): $^1$H NMR: δ 8.71 (br.s, 1H), 7.97 (d, J=8.2 Hz, 1H), 7.93 (d, J=8.1 Hz, 1H), 7.65-7.59 (m, 2H), 7.54 (ddd, J=8.2, 6.8, 1.3 Hz, 1H), 7.48-7.41 (m, 3H), 7.31 (d, J=8.6 Hz, 2H), 4.44 (t, J=6.1 Hz, 1H), 3.29 (q, J=6.5 Hz, 2H), 3.02 (t, J=6.7 Hz, 2H), 2.95 (t, J=7.4 Hz, 2H), 2.26 (td, J=6.8, 2.7 Hz, 2H), 2.14 (t, J=2.6 Hz, 1H), 1.90 (p, J=7.0 Hz, 2H); $^{13}$C NMR: δ 138.2, 133.7, 130.1, 129.7, 129.2, 129.0, 128.3, 125.6, 123.8, 123.5, 121.2, 120.5, 119.1, 117.9, 109.1, 83.7, 69.9, 43.6, 31.9, 31.6, 28.6, 24.6, 24.5, 22.7, 17.7; m/z: Calcd for C$_{25}$H$_{24}$ClN$_2$O$_2$S [M+H]$^+$ 451.1242. Found 451.1246; IR: 3424, 2952, 2843, 1646, 1454, 1405, 1111, 1032, 1016, 623 cm$^{-1}$. N-{2-[7-bromo-2-(pent-4-yn-1-yl)-1H-indol-3-yl] ethyl}-4-chlorobenzene-1-sulfonamide (4g): $^1$H NMR: δ 8.56 (brs, 1H), 7.83 (d, J=8.3 Hz, 2H), 7.55-7.43 (m, 3H), 7.30 (d, J=7.6 Hz, 1H), 6.98 (t, J=7.7 Hz, 1H), 4.99 (t, J=6.5 Hz, 1H), 3.01 (q, J=6.3 Hz, 2H), 2.90 (t, J=7.1 Hz, 4H), 2.47 (td, J=7.5, 2.6 Hz, 2H), 1.96 (s, 1H), 1.88 (p, J=6.8 Hz, 2H); $^{13}$C NMR: δ 139.4, 138.1, 135.4, 134.1, 129.6, 129.3, 129.2, 128.5, 123.7, 120.5, 117.3, 111.8, 104.3, 84.3, 69.0, 42.2, 30.3, 23.8, 22.4, 20.0; m/z: Calcd for C$_{21}$H$_{20}$BrClN$_2$O$_2$S [M+H]$^+$ 479.0190. Found 479.0186; IR: 3299, 2917, 2849, 1710, 1585, 1451, 1326, 1160, 1095, 1014, 828 cm$^{-1}$. N-{2-[6-bromo-2-(pent-4-yn-1-yl)-1H-indol-3-yl]ethyl}-4-chlorobenzene-1-sulfonamide (4h): $^1$H NMR: δ 7.99 (brs, 1H), 7.65 (d, J=8.4 Hz, 2H), 7.44 (s, 1H), 7.39 (d, J=8.3 Hz, 2H), 7.19 (d, J=8.4 Hz, 1H), 7.17-7.08 (m, 1H), 4.47 (t, J=6.3 Hz, 1H), 3.23 (q, J=6.6 Hz, 2H), 2.92 (t, J=6.8 Hz, 2H), 2.84 (t, J=7.4 Hz, 2H), 2.21 (dt, J=6.9, 3.3 Hz, 2H), 2.08 (s, 1H), 1.83 (p, J=7.1 Hz, 2H); $^{13}$C NMR: δ 139.1, 138.2, 136.4, 136.1, 129.2, 128.3, 126.8, 122.8, 119.0, 115.1, 113.6, 107.6, 83.5, 69.9, 43.2, 28.1, 24.6, 24.4, 17.7; m/z: Calcd for C$_2$H$_{20}$BrClN$_2$O$_2$S [M+H]$^+$ 479.0190. Found 479.0180; IR: 3356, 3299, 2924, 2851, 2359, 2342, 1716, 1587, 1506, 1463, 1326, 1159, 1094, 1014, 828 cm$^{-1}$. N-{2-[4-bromo-2-(pent-4-yn-1-yl)-1H-indol-3-yl]ethyl}-4-chlorobenzene-1-sulfonamide (4i): $^1$H NMR: δ 8.07 (brs, 1H), 7.67 (d, J=8.6 Hz, 2H), 7.37 (d, J=8.6 Hz, 2H), 7.24 (d, J=8.0 Hz, 1H), 7.21 (d, J=7.5 Hz, 1H), 6.97 (t, J=8.0 Hz, 1H), 4.53 (t, J=6.1 Hz, 1H), 3.32 (q, J=6.7 Hz, 2H), 3.15 (t, J=7.0 Hz, 2H), 2.94-2.87 (m, 2H), 2.32-2.20 (m, 2H), 2.12 (t, J=2.6 Hz, 1H), 1.90-1.83 (m, 2H); $^{13}$C NMR: δ 138.8, 138.5, 137.4, 136.6, 129.6, 128.7, 125.8, 124.5, 124.2, 122.7, 122.4, 113.0, 110.0, 108.4, 83.2, 69.9, 45.1, 28.0, 24.6, 17.8; m/z: Calcd for C$_2$H$_{20}$BrClN$_2$O$_2$S [M+H]$^+$ 479.0190. Found 479.0197; IR: 3304, 2919, 2850, 1718, 1654, 1458, 1276, 1106, 913, 750 cm$^{-1}$.

4-Chloro-N-{2-[5-chloro-7-fluoro-2-(pent-4-yn-1-yl)-1H-indol-3-yl]ethyl}benzene-1-sulfonamide (4j): $^1$H NMR: δ 8.23 (brs, 1H), 7.68 (d, J=8.7 Hz, 2H), 7.42 (d, J=8.7 Hz, 2H), 7.05 (d, J=1.8 Hz, 1H), 6.88 (dd, J=10.4, 1.7 Hz, 1H), 4.54 (t, J=6.2 Hz, 1H), 3.23 (q, J=6.6 Hz, 2H), 2.90-2.87 (m, 4H), 2.26-2.20 (m, 2H), 2.09 (s, 1H), 1.91-1.82 (m, 2H); $^{13}$C NMR: δ 139.1, 138.2, 138.0, 129.3, 128.3, 124.8, 124.7, 113.4, 113.3, 108.2, 108.0, 107.8, 83.3, 70.0, 43.0, 28.0, 24.7, 24.5, 17.8; m/z: Calcd for C$_{21}$H$_{20}$Cl$_2$FN$_2$O$_2$S [M+H]$^+$ 453.0601. Found 453.0616; IR: 3445, 2962, 2081, 1652, 1456, 1261, 1096, 1033, 800 cm$^{-1}$. 4-Chloro-N-{2-[5,7-dichloro-2-(pent-4-yn-1-yl)-1H-indol-3-yl]ethyl}benzene-1-sulfonamide (4k): $^1$H NMR: δ 8.16 (brs, 1H), 7.66 (d, J=8.6 Hz, 2H), 7.41 (d, J=8.6 Hz, 2H), 7.21-7.11 (m, 2H), 4.44 (t, J=6.3 Hz, 1H), 3.23 (q, J=6.6 Hz, 2H), 3.03-2.79 (m, 4H), 2.26 (td, J=6.7, 2.7 Hz, 2H), 2.11 (s, 1H), 1.88 (p, J=7.1 Hz, 2H); $^{13}$C NMR: δ 139.2, 138.2, 138.1, 131.2, 129.9, 129.3, 128.3, 125.3, 121.1, 116.5, 116.1, 108.5, 83.3, 70.0, 43.0, 28.0, 24.8, 24.5, 17.8; m/z: Calcd for C$_{21}$H$_{20}$Cl3N$_2$O$_2$S [M+H]$^+$ 469.0306. Found 469.0319; IR: 3353, 3301, 3088, 2928, 2854, 1713, 1574, 1476, 1328, 1161, 1095, 1014, 964, 912, 828, 753 cm$^{-1}$. Benzyl {2-[5-bromo-2-(pent-4-yn-1-yl)-1H-indol-3-yl]ethyl}carbamate (8a): $^1$H NMR: δ 8.05 (brs, 1H), 7.65 (s, 1H), 7.40-7.31 (m, 5H), 7.23 (dd, J=8.5, 1.9 Hz, 1H), 7.16 (d, J=8.6 Hz, 1H), 5.12 (s, 2H), 4.82 (t, J=6.1 Hz, 1H), 3.45 (q, J=6.7 Hz, 2H), 2.90 (t, J=6.9 Hz, 2H), 2.85 (t, J=7.4 Hz, 2H), 2.21 (td, J=6.9, 2.7 Hz, 2H), 2.07 (t, J=2.5 Hz, 1H), 1.84 (h, J=6.1, 5.0 Hz, 2H); $^{13}$C NMR: δ 156.3, 136.8, 136.5, 134.0, 130.2, 128.6, 128.5, 128.3, 128.1, 128.1, 124.2, 120.7, 112.7, 111.9, 108.5, 83.6, 69.7, 66.7, 41.5, 28.2, 24.6, 24.5, 17.7; m/z: Calcd for C$_{23}$H$_{24}$BrN$_2$O$_2$ [M+H]$^+$ 439.1016. Found 4; IR: 3295, 2920, 2850, 1698, 1518, 1454, 1251, 1135, 1075, 797, 748 cm$^{-1}$. Benzyl {2-[5-bromo-7-fluoro-2-(pent-4-yn-1-yl)-1H-indol-3-yl]ethyl}carbamate (8b): $^1$H NMR: δ 9.82 (brs, 1H), 7.49-7.32 (m, 6H), 7.01 (dd, J=10.1, 1.6 Hz, 1H), 5.19 (s, 2H), 4.96 (brs, 1H), 3.33 (q, J=6.3 Hz, 2H), 2.90 (t, J=7.5 Hz, 2H), 2.81 (t, J=6.7 Hz, 2H), 2.47 (td, J=7.5, 2.7 Hz, 2H), 1.98 (s, 1H), 1.83 (p, J=6.6 Hz, 2H); $^{13}$C NMR: δ 157.7, 137.5, 136.2, 132.7, 132.7, 128.6, 128.3, 128.2, 122.3, 116.5, 110.5, 109.8, 109.6, 84.2, 69.0, 67.2, 39.5, 31.0, 23.6, 21.9, 20.1; m/z: Calcd for C$_{23}$H$_{23}$BrFN$_2$O$_2$ [M+H]$^+$ 457.0921. Found 457.0924; IR: 3298, 2923, 2851, 1701, 1638, 1523, 1477, 1454, 1308, 1255, 1217, 1131, 1005, 882, 826, 697 cm$^{-1}$. N-{2-[5-bromo-2-(hex-5-yn-1-yl)-1H-indol-3-yl]ethyl}-4-chlorobenzene-1-sulfonamide (4m'): $^1$H NMR: δ 8.00 (brs, 1H), 7.66 (d, J=8.6 Hz, 1H), 7.41 (d, J=8.7 Hz, 2H), 7.21 (dd, J=8.5, 1.8 Hz, 1H), 7.15 (d, J=8.6 Hz, 1H), 4.47 (t, J=6.2 Hz, 1H), 3.22 (q, J=6.5 Hz, 2H), 2.87 (t, J=6.7 Hz, 2H), 2.73 (t, J=7.7 Hz, 2H), 2.24 (td, J=6.9, 2.7 Hz, 2H), 2.00 (t, J=2.6 Hz, 1H), 1.77 (dq, J=12.6, 7.7 Hz, 2H), 1.57 (p, J=7.0 Hz, 2H); $^{13}$C NMR: δ 139.1, 138.2, 138.0, 133.9, 129.7, 129.5, 129.3, 128.3, 124.3, 120.3, 112.8, 112.0, 106.6, 84.0, 69.0, 43.0, 28.6, 27.8, 25.5, 24.6, 18.1. Benzyl N-{2-[5-bromo-7-fluoro-2-(hex-5-yn-1-yl)-1H-indol-3-yl]ethyl}carbamate (4m): $^1$H NMR: δ 7.40-7.32 (m, 6H), 7.04-6.99 (m, 1H), 5.18 (s, 2H), 4.98 (brs, 1H), 3.33 (q, J=6.4 Hz, 2H), 2.78 (dt, J=10.6, 7.1 Hz, 4H), 2.20 (td, J=6.9, 2.7 Hz, 2H), 2.04 (d, J=2.6 Hz, 1H), 1.83 (td, J=7.2, 3.4 Hz, 4H). N-{3-[5-bromo-2-(pent-4-yn-1-yl)-1H-indol-3-yl]propyl}-4-chlorobenzene-1-sulfonamide (4n): $^1$H NMR: δ 7.73 (d, J=8.6 Hz, 2H), 7.48 (d, J=8.6 Hz, 3H), 7.22 (dd, J=8.5, 1.8 Hz, 1H), 7.17 (d, J=8.5 Hz, 1H), 4.44 (t, J=6.1 Hz, 1H), 3.01 (q, J=6.8 Hz, 2H), 2.85 (t, J=7.4 Hz, 2H), 2.68 (q, J=6.1, 4.8 Hz, 2H), 2.23 (td, J=6.7, 2.7 Hz, 2H), 2.12 (t, J=2.6 Hz, 1H), 1.82 (dp, J=24.4, 7.1 Hz, 4H); $^{13}$C NMR: δ 139.1, 138.3, 135.9, 134.0, 132.3, 130.0, 129.4, 129.4, 129.1, 128.5, 128.5, 128.4, 127.0, 126.2, 124.1, 120.6, 112.6, 112.0, 110.5, 83.6, 69.8, 43.2, 30.3, 29.7, 28.2, 24.4, 21.1, 17.7. 4-Chloro-16-(4-chlorobenzenesulfonyl)-13-methylidene-8,16-diazatetracyclo[7.4.3.0$^{1,9}$.0$^{2,7}$]hexadeca-2,4,6-triene (5a): $^1$H NMR: δ 7.61 (d, J=8.8 Hz, 2H), 7.38 (d, J=8.8 Hz, 2H), 7.05-7.03 (m, 2H), 6.51 (d, J=8.1 Hz, 1H), 5.19 (br.s, 1H), 4.92 (s, 1H), 4.77 (s, 1H), 3.48 (td, J=8.7, 1.7 Hz, 1H), 3.03-2.98 (m, 1H), 2.72 (dt, J=14.2, 3.8 Hz, 1H), 2.37 (ddd, J=12.7, 10.5, 8.4 Hz, 1H), 2.24-2.12 (m, 3H), 1.93-1.86 (m, 1H), 1.75 (dt, J=13.7, 4.5 Hz, 1H), 1.63-1.55 (m, 1H); $^{13}$C NMR: δ 147.2, 146.4, 138.9, 138.4, 133.0, 129.2, 128.4, 128.3, 124.6, 123.8, 112.8, 111.0, 93.5, 61.1, 47.4, 33.8, 32.0, 30.3, 22.8; m/z: Calcd for C$_{21}$H$_{20}$Cl$_2$N$_2$O$_2$S [M+H]$^+$ 435.0695. Found 435.0691; IR: 3054, 2986, 2926, 2850, 1718, 1423, 1335, 1265, 1156, 1090, 1001, 740 cm$^{-1}$. 16-(4-Chlorobenzenesulfonyl)-4-methyl-13-methylidene-8,16-diazatetracyclo[7.4.3.0$^{1,9}$.0$^{2,7}$]hexadeca-2,4,6-triene (5b): $^1$H NMR: δ 7.59 (d, J=8.7 Hz, 2H), 7.34 (d, J=8.7 Hz, 2H), 6.92-6.84 (m, 2H), 6.48 (d, J=7.8 Hz, 1H), 5.06 (br.s, 1H), 4.89 (s, 1H), 4.78 (s, 1H), 3.48 (td, J=8.6, 1.7 Hz, 1H), 2.95 (ddd, J=10.3, 8.7, 6.8 Hz, 1H), 2.73 (dt, J=14.1, 3.8 Hz, 1H), 2.37 (ddd, J=12.5, 10.4, 8.3 Hz, 1H), 2.27 (s, 3H), 2.26-2.19 (m, 1H), 2.15 (ddd, J=14.2, 10.2, 5.2 Hz, 1H), 1.93 (ddd, J=13.9, 12.5, 4.6 Hz, 1H), 1.77-1.71 (m, 1H), 1.60 (tdd, J=18.0, 9.9, 4.8 Hz, 1H); $^{13}$C NMR: δ 148.0, 145.4, 138.6, 138.5, 131.2, 129.0, 128.8, 128.5, 128.4, 125.0, 112.4, 110.1, 93.7, 61.0, 47.4, 34.2, 32.1, 30.5, 23.1, 21.0; m/z: Calcd for $C_{22}H_{24}ClN_2O_2S$ [M+H]$^+$ 415.1242. Found 415.1245; IR: 3391, 3088, 2941, 2865, 1639, 1585, 1493, 1332, 1155, 1089, 1002, 904, 813, 623 cm$^{-1}$. 16-(4-Chlorobenzenesulfonyl)-4-methoxy-13-methylidene-8,16-diazatetracyclo[7.4.3.0$^{1,9}$.0$^{2,7}$]hexadeca-2,4,6-triene (5c): $^1$H NMR: δ 7.58 (d, J=8.6 Hz, 2H), 7.34 (d, J=8.6 Hz, 2H), 6.70 (d, J=2.5 Hz, 1H), 6.62 (dd, J=8.4, 2.5 Hz, 1H), 6.48 (d, J=8.4 Hz, 1H), 4.95 (brs, 1H), 4.90 (s, 1H), 4.77 (s, 1H), 3.76 (s, 3H), 3.50 (td, J=8.6, 1.5 Hz, 1H), 2.94 (ddt, J=11.2, 6.8, 5.6 Hz, 1H), 2.73 (dtd, J=14.1, 3.8, 1.2 Hz, 1H), 2.41-2.35 (m, 1H), 2.28-2.11 (m, 3H), 1.96-1.89 (m, 1H), 1.81-1.72 (m, 1H), 1.64-1.57 (m, 1H); $^{13}$C NMR: $^{13}$C NMR: δ 153.5, 147.6, 141.5, 138.6, 138.4, 132.7, 129.4, 129.3, 129.0, 128.5, 128.4, 128.4, 112.7, 112.7, 111.7, 110.7, 94.1, 69.6, 61.2, 56.0, 47.4, 34.3, 31.9, 30.6, 23.2; m/z: Calcd for $C_{22}H_{24}ClN_2O_2S$ [M+H]$^+$ 431.1191. Found 431.1195; IR: 3386, 3300, 2942, 2866, 1708, 1586, 1491, 1333, 1158, 1003, 829 cm$^{-1}$. 16-(4-Chlorobenzenesulfonyl)-4-fluoro-13-methylidene-8,16-diazatetracyclo[7.4.3.0$^{1,9}$.0$^{2,7}$]hexadeca-2,4,6-triene (5d): $^1$H NMR: δ 7.60 (d, J=8.6 Hz, 2H), 7.37 (d, J=8.6 Hz, 2H), 6.83 (dd, J=8.2, 2.6 Hz, 1H), 6.78 (td, J=8.8, 2.6 Hz, 1H), 6.49 (dd, J=8.5, 4.2 Hz, 1H), 5.08 (brs, 1H), 4.92 (s, 1H), 4.75 (s, 1H), 3.51 (td, J=8.7, 1.6 Hz, 1H), 2.98 (ddd, J=10.4, 8.8, 6.9 Hz, 1H), 2.73 (dd, J=14.1 Hz, 1H), 2.39 (ddd, J=12.7, 10.4, 8.5 Hz, 1H), 2.28-2.11 (m, 3H), 1.91 (td, J=13.5, 4.6 Hz, 1H), 1.76 (dt, J=13.4, 4.3 Hz, 1H), 1.60 (tdd, J=13.3, 9.9, 6.4 Hz, 1H); $^{13}$C NMR: δ 158.6, 155.4, 147.2, 143.7, 143.7, 138.8, 138.4, 134.2, 134.1, 132.9, 132.8, 132.0, 132.0, 129.3, 129.3, 129.2, 129.1, 128.4, 114.7, 114.4, 112.9, 112.1, 111.8, 110.7, 110.6, 94.1, 61.1, 61.1, 47.3, 34.1, 31.9, 30.5, 23.1; m/z: Calcd for $C_{21}H_{20}ClFN_2O_2S$ [M+H]$^+$ 419.0991. Found 419.0995; IR: 3389, 3090, 2944, 2869, 1693, 1640, 1585, 1486, 1278, 1225, 1002, 884 cm$^{-1}$. 16-(4-Chlorobenzenesulfonyl)-13-methylidene-8,16-diazatetracyclo[7.4.3.0$^{1,9}$.0$^{2,7}$]hexadeca-2,4,6-triene (5e): $^1$H NMR: δ 7.57 (d, J=8.6 Hz, 2H), 7.34 (d, J=8.6 Hz, 2H), 7.14-7.03 (m, 2H), 6.78 (t, J=7.5 Hz, 1H), 6.57 (d, J=7.8 Hz, 1H), 5.17 (brs, 1H), 4.90 (s, 1H), 4.76 (s, 1H), 3.50 (dd, J=9.6, 8.0 Hz, 1H), 2.95 (ddd, J=10.3, 8.7, 6.9 Hz, 1H), 2.79-2.70 (m, 1H), 2.43-2.37 (m, 1H), 2.30-2.21 (m, 2H), 2.17 (td, J=14.1, 12.4, 5.0 Hz, 1H), 1.98-1.91 (m, 1H), 1.81-1.72 (m, 1H), 1.65-1.55 (m, 1H); $^{13}$C NMR: δ 147.8, 147.6, 138.7, 138.5, 131.0, 129.1, 128.4, 124.3, 119.2, 112.6, 110.3, 93.4, 60.9, 47.5, 34.2, 32.0, 30.5, 23.1; m/z: Calcd for $C_{21}H_{21}ClN_2O_2S$ [M+H]$^+$ 401.1085. Found 401.1100; IR: 3393, 3087, 2943, 2869, 1640, 1589, 1474, 1466, 1191, 893, 830 cm$^{-1}$. 20-(4-Chlorobenzenesulfonyl)-17-methylidene-12,20-diazapentacyclo[11.4.3.0$^{1,13}$.0$^{2,11}$.0$^{5,10}$]icosa-2,4,6,8,10-pentaene (5f): $^1$H NMR: δ 7.80 (dd, J=6.2, 3.3 Hz, 1H), 7.61 (dd, J=6.2, 3.3 Hz, 1H), 7.50-7.40 (m, 4H), 7.32 (d, J=8.2 Hz, 1H), 7.26 (d, J=6.0 Hz, 1H), 6.99 (d, J=8.6 Hz, 2H), 5.63 (br.s, 1H), 4.90 (s, 1H), 4.79 (s, 1H), 3.57 (td, J=8.5, 1.5 Hz, 1H), 2.95-2.80 (m, 2H), 2.48 (ddd, J=12.8, 10.7, 8.2 Hz, 1H), 2.37 (ddd, J=12.9, 6.8, 1.5 Hz, 1H), 2.21 (t, J=6.4 Hz, 2H), 2.10-1.98 (m, 1H), 1.88-1.77 (m, 1H), 1.73-1.63 (m, 1H); $^{13}$C NMR: δ 148.6, 143.8, 138.4, 138.0, 134.0, 128.8, 128.5, 128.2, 128.2, 125.7, 125.1, 124.6, 122.1, 121.6, 120.6, 119.3, 112.4, 93.6, 61.9, 47.8, 34.4, 32.3, 30.3, 22.9; m/z: Calcd for $C_{25}H_{24}ClN_2O_2S$ [M+H]$^+$ 451.1242. Found 451.1252; IR: 3370, 3302, 3054, 2924, 2853, 1713, 1633, 1587, 1476, 1391, 1327, 1265, 1160, 1093, 1014, 807 cm$^{-1}$. 6-Bromo-16-(4-chlorobenzenesulfonyl)-13-methylidene-8,16-diazatetracyclo[7.4.3.0$^{1,9}$.0$^{2,7}$]hexadeca-2,4,6-triene (5g): $^1$H NMR: δ 7.62 (d, J=8.6 Hz, 2H), 7.36 (d, J=8.7 Hz, 2H), 7.23 (d, J=8.0 Hz, 1H), 7.00 (d, J=7.3 Hz, 1H), 6.65 (t, J=7.7 Hz, 1H), 5.45 (s, 1H), 4.91 (s, 1H), 4.73 (s, 1H), 3.54 (td, J=8.6, 1.6 Hz, 1H), 2.90-2.75 (m, 2H), 2.44 (ddd, J=12.7, 10.6, 8.4 Hz, 1H), 2.20 (dtd, J=19.1, 14.2, 7.6 Hz, 3H), 2.01 (td, J=14.1, 13.6, 4.7 Hz, 1H), 1.78 (tt, J=9.1, 4.6 Hz, 1H), 1.68-1.62 (m, 1H); $^{13}$C NMR: δ 147.2, 146.5, 138.8, 137.7, 132.5, 131.0, 129.1, 128.5, 123.3, 120.3, 112.8, 103.9, 92.6, 62.3, 47.2, 34.5, 32.2, 30.4, 29.7, 22.8; m/z: Calcd for $C_{21}H_{20}BrClN_2O_2S$ [M+H]$^+$ 479.0190. Found 479.0209; IR: 3054, 2926, 2853, 1607, 1585, 1465, 1421, 1265, 1158, 1061, 1101, 896, 740 cm$^{-1}$. 5-Bromo-16-(4-chlorobenzenesulfonyl)-13-methylidene-8,16-diazatetracyclo[7.4.3.0$^{1,9}$.0$^{2,7}$]hexadeca-2,4,6-triene (5h): $^1$H NMR: δ 7.60 (d, J=8.6 Hz, 2H), 7.40 (d, J=8.6 Hz, 2H), 6.92 (d, J=7.8 Hz, 1H), 6.88 (dd, J=7.8, 1.7 Hz, 1H), 6.66 (d, J=1.6 Hz, 1H), 5.17 (brs, 1H), 4.90 (s, 1H), 4.72 (s, 1H), 3.50 (td, J=8.6, 1.4 Hz, 1H), 3.04-2.96 (m, 1H), 2.76-2.67 (m, 1H), 2.40-2.34 (m, 1H), 2.27-2.19 (m, 2H), 2.18-2.10 (m, 1H), 1.92-1.86 (m, 1H), 1.78-1.71 (m, 1H); $^{13}$C NMR: δ 149.0, 147.3, 139.0, 138.3, 134.3, 134.1, 132.0, 130.2, 129.3, 129.2, 129.2, 128.3, 125.5, 121.9, 121.9, 113.4, 112.8, 93.2, 60.6, 47.6, 34.1, 31.9, 29.7, 22.9; m/z: Calcd for $C_{21}H_{20}BrClN_2O_2S$ [M+H]$^+$ 479.0190. Found 479.0185; IR: 3391, 2917, 2849, 1602, 1585, 1478, 1436, 1392, 1333, 1154, 1104, 997, 752 cm$^{-1}$. 3-Bromo-16-(4-chlorobenzenesulfonyl)-13-methylidene-8,16-diazatetracyclo[7.4.3.0$^{1,9}$.0$^{2,7}$]hexadeca-2,4,6-triene (5i): $^1$H NMR: δ 7.62 (d, J=8.6 Hz, 2H), 7.38 (d, J=8.6 Hz, 2H), 6.99-6.84 (m, 2H), 6.51 (dd, J=7.6, 1.2 Hz, 1H), 5.24 (brs, 1H), 5.01 (s, 1H), 4.91 (s, 1H), 3.50 (t, J=8.2 Hz, 1H), 3.16 (dd, J=13.2, 6.3 Hz, 1H), 3.05-3.00 (m, 1H), 2.69 (ddd, J=14.1, 4.7, 3.0 Hz, 1H), 2.32-2.26 (m, 1H), 2.16 (t, J=6.6 Hz, 2H), 1.88 (td, J=13.2, 5.2 Hz, 1H), 1.76-1.73 (m, 1H), 1.66-1.61 (m, 1H); $^{13}$C NMR: δ 150.2, 146.5, 138.6, 130.8, 130.2, 129.1, 128.4, 124.0, 120.5, 114.4, 109.1, 93.4, 63.9, 47.6, 33.6, 32.8, 30.8, 29.4, 22.9; m/z: Calcd for $C_{21}H_{20}BrClN_2O_2S$ [M+H]$^+$ 479.0190. Found 479.0188; IR: 3393, 2954, 2916, 2848, 1261, 1159, 1090, 912, 764 cm$^{-1}$. 4-Chloro-16-(4-chlorobenzenesulfonyl)-6-fluoro-13-methylidene-8,16-diazatetracyclo[7.4.3.0$^{1,9}$.0$^{2,7}$]hexadeca-2,4,6-triene (5j): $^1$H NMR: δ 7.63 (d, J=8.7 Hz, 2H), 7.40 (d, J=8.7 Hz, 2H), 6.97-6.83 (m, 2H), 5.28 (brs, 1H), 4.94 (s, 1H), 4.73 (s, 1H), 3.55 (t, J=8.6 Hz, 1H), 2.96-2.91 (m, 1H), 2.77 (dt, J=14.4, 3.8 Hz, 1H), 2.44-2.38 (m, 1H), 2.27-2.09 (m, 3H), 1.94 (td, J=13.5, 4.6 Hz, 1H), 1.79-1.75 (m, 1H); $^{13}$C NMR: δ 146.6, 139.0, 137.7, 129.2, 128.2, 123.5, 120.4, 120.4, 115.9, 115.6, 113.1, 93.5, 61.7, 47.4, 34.2, 31.9, 29.7, 22.8; m/z: Calcd for $C_{21}H_{20}Cl_2FN_2O_2S$ [M+H]$^+$ 453.0601. Found 453.0614; IR: 3054, 2986, 2926, 2853, 1584, 1422, 1265, 1159, 1013, 975, 896, 740, 705 cm$^{-1}$. (4,6-Dichloro-16-(4-chlorobenzenesulfonyl)-13-methylidene-8,16-diazatetracyclo[7.4.3.0$^{1,9}$.0$^{2,7}$]hexadeca-2,4,6-triene (5k): $^1$H NMR: δ 7.63 (d, J=8.6 Hz, 2H), 7.39 (d, J=8.7 Hz, 2H), 7.10 (d, J=1.9 Hz, 1H), 6.93 (d, J=1.9 Hz, 1H), 5.44 (brs, 1H), 4.94 (s, 1H), 4.74 (s, 1H), 3.53 (td, J=8.6, 1.6 Hz, 1H), 2.90-2.85 (m, 1H), 2.79 (dt, J=14.3, 3.9 Hz, 1H), 2.45-2.38 (m, 1H), 2.24-2.16 (m, 3H), 1.96 (ddd, J=14.1, 12.5, 4.7 Hz, 1H), 1.78-1.75 (m, 1H), 1.65-1.60 (m, 1H); $^{13}$C NMR: δ 146.6, 143.9, 139.0, 137.7, 133.9, 129.2, 128.4, 127.8, 123.9, 123.2, 115.7, 113.1, 92.9, 62.2, 47.1, 34.1, 32.2, 30.2, 22.6; m/z: Calcd for $C_{21}H_{20}Cl_3N_2O_2S$ [M+H]$^+$ 469.0306. Found 469.0305; IR:

3380, 2928, 2856, 2360, 1700, 1636, 1583, 1464, 1336, 1156, 1092, 1010, 904, 631 cm$^{-1}$. 4-Bromo-16-(4-chlorobenzenesulfonyl)-8,16-diazatetracyclo[7.4.3.0$^{1,9}$.0$^{2,7}$]hexadeca-2,4,6,12-tetraene (5l): $^1$H NMR: δ 7.72 (d, J=8.6 Hz, 2H), 7.42 (d, J=8.6 Hz, 2H), 7.18-7.13 (m, 2H), 6.43 (d, J=8.0 Hz, 1H), 5.74 (ddd, J=9.9, 5.5, 2.3 Hz, 1H), 5.66-5.60 (m, 1H), 5.13 (s, 1H), 3.43 (ddd, J=9.2, 8.0, 2.0 Hz, 1H), 3.04 (ddd, J=10.3, 8.9, 6.3 Hz, 1H), 2.77 (ddd, J=13.4, 5.0, 2.8 Hz, 1H), 2.35 (ddd, J=12.6, 6.3, 1.9 Hz, 1H), 2.26 (dddd, J=16.9, 9.0, 5.1, 2.6 Hz, 1H), 2.14-2.00 (m, 2H), 1.91 (ddd, J=13.5, 11.6, 5.2 Hz, 1H); $^{13}$C NMR: δ 146.6, 138.9, 138.4, 133.8, 131.2, 129.2, 129.1, 129.1, 128.6, 128.5, 128.5, 128.5, 126.3, 125.9, 125.7, 122.7, 119.5, 111.1, 110.9, 109.8, 90.6, 56.7, 47.0, 34.5, 30.8, 22.8, 22.7, 14.1. 4-Bromo-17-(4-chlorobenzenesulfonyl)-14-methylidene-8,17-diazatetracyclo[7.5.3.0$^{1,9}$.0$^{2,7}$]heptadeca-2,4,6-triene (5k): $^1$H NMR: δ 7.70 (d, J=8.6 Hz, 2H), 7.43 (d, J=8.6 Hz, 2H), 7.14 (dd, J=8.3, 2.0 Hz, 1H), 6.95 (d, J=2.1 Hz, 1H), 6.45 (d, J=8.3 Hz, 1H), 5.29 (s, 1H), 4.98 (s, 1H), 4.89 (s, 1H), 3.38-3.29 (m, 1H), 2.95 (ddd, J=11.9, 8.7, 5.5 Hz, 1H), 2.81 (dd, J=12.9, 6.2 Hz, 1H), 2.73 (s, 1H), 2.44-2.35 (m, 1H), 2.28 (dd, J=12.4, 5.5 Hz, 1H), 1.86-1.77 (m, 4H), 1.73-1.64 (m, 1H); $^{13}$C NMR: δ 151.9, 147.3, 139.0, 138.5, 132.8, 131.4, 129.8, 129.4, 129.2, 129.1, 128.6, 128.5, 128.5, 127.6, 126.4, 112.3, 110.3, 94.7, 65.8, 47.5, 36.0, 33.2, 33.1, 31.6, 29.7, 24.6. 4-Bromo-10-(4-chlorobenzenesulfonyl)-14-methylidene-8,10-diazatetracyclo[7.4.4.0$^{1,9}$.0$^{2,7}$]heptadeca-2,4,6-triene (5n): TLC (hexanes:ethyl acetate, 3:1 v/v): R$_f$=0.60; colorless oil, 82%; $^1$H NMR: δ 7.74 (d, J=8.6 Hz, 2H), 7.56-7.39 (m, 5H), 4.82 (d, J=4.9 Hz, 2H), 4.38 (t, J=6.2 Hz, 1H), 2.96-2.88 (m, 1H), 2.84 (q, J=6.6 Hz, 2H), 2.61-2.46 (m, 2H), 2.39-2.33 (m, 1H), 2.27-2.19 (m, 1H), 1.98-1.88 (m, 2H), 1.52 (dt, J=13.4, 4.3 Hz, 1H); $^{13}$C NMR: δ 153.6, 147.4, 142.6, 139.3, 138.3, 131.2, 129.5, 128.4, 127.4, 122.2, 118.7, 110.9, 65.8, 43.0, 32.6, 31.3, 29.7, 29.5, 29.1, 24.2. N-(2-(6-Bromo-4-methylene-2,3,4,4a,9,9a-hexahydro-1H-carbazol-4a-yl)ethyl)-4-chlorobenzenesulfonamide (Of1): TLC (hexanes:ethyl acetate, 5:1 v/v): R$_f$=0.20; colorless oil, 92%; $^1$H NMR (500 MHz, CDCl$_3$) δ 7.78-7.73 (m, 2H), 7.52-7.45 (m, 2H), 7.14 (dd, J=8.2, 2.0 Hz, 1H), 6.98 (d, J=2.0 Hz, 1H), 6.51 (d, J=8.2 Hz, 1H), 4.93 (d, J=0.8 Hz, 1H), 4.66 (s, 1H), 3.71 (s, 1H), 3.61 (t, J=4.9 Hz, 1H), 3.06-2.83 (m, 2H), 2.27-2.07 (m, 2H), 2.06-1.90 (m, 2H), 1.83-1.72 (m, 1H), 1.72-1.52 (m, 2H), 1.52-1.40 (m, 1H); $^{13}$C NMR (101 MHz, CDCl$_3$) δ 149.00, 148.78, 139.37, 138.53, 135.62, 130.91, 129.66, 128.68, 127.17, 112.36, 112.06, 110.89, 65.57, 52.51, 40.42, 36.39, 32.63, 28.89, 21.85; m/z: Calcd for C$_{21}$H$_{22}$BrClN$_2$O$_2$S [M+H]$^+$ 481.0347. Found 481.0349; IR: 3381, 2955, 2924, 2855, 1636, 1603, 1505, 1463, 1378, 1167, 1086, 970 cm$^{-1}$. 4-Chloro-N-[2-(6-chloro-4-methylidene-2,3,4,4a,9,9a-hexahydro-1H-carbazol-4a-yl)ethyl]benzene-1-sulfonamide (6a): TLC (hexanes:ethyl acetate, 3:1 v/v): R$_f$=0.20; colorless oil, 92%; $^1$H NMR: δ 7.77 (d, J=8.6 Hz, 2H), 7.49 (d, J=8.6 Hz, 2H), 7.01 (dd, J=8.3, 2.2 Hz, 1H), 6.87 (s, 1H), 6.58 (d, J=8.3 Hz, 1H), 5.13 (d, J=5.9 Hz, 1H), 4.94 (s, 1H), 4.67 (s, 1H), 3.63 (t, J=4.9 Hz, 1H), 3.00-2.89 (m, 1H), 2.20-2.11 (m, 2H), 2.07-2.01 (m, 1H), 1.98-1.93 (m, 1H), 1.81-1.76 (m, 1H), 1.70-1.57 (m, 1H), 1.52-1.46 (m, 1H); $^{13}$C NMR: δ 148.6, 148.2, 139.2, 138.4, 135.1, 129.4, 128.5, 127.8, 124.2, 123.8, 112.1, 111.4, 77.5, 77.0, 76.6, 65.4, 52.3, 40.2, 36.1, 32.4, 28.6, 21.7; m/z: Calcd for C$_{21}$H$_{22}$Cl$_2$N$_2$O$_2$S [M+H]$^+$ 437.0852. Found 437.0857; IR: 2264, 3285, 2934, 2858, 1637, 1604, 1587, 1477, 1428, 1328, 1160, 1093, 1014,905, 827, 617 cm$^{-1}$. 4-Chloro-N-[2-(6-methyl-4-methylidene-2,3,4,4a,9,9a-hexahydro-1H-carbazol-4a-yl)ethyl]benzene-1-sulfonamide (6b): TLC (hexanes:ethyl acetate, 3:1 v/v): R$_f$=0.30; colorless oil, 95%; $^1$H NMR: δ 7.74 (d, J=8.6 Hz, 2H), 7.46 (d, J=8.6 Hz, 2H), 6.90-6.84 (m, 1H), 6.75-6.69 (m, 1H), 6.58 (d, J=7.8 Hz, 1H), 5.29 (s, 1H), 4.93 (s, 1H), 4.70 (d, J=1.4 Hz, 1H), 3.57 (t, J=5.2 Hz, 1H), 3.03-2.98 (m, 1H), 2.90-2.78 (m, 1H), 2.24 (s, 3H), 2.17-2.10 (m, 2H), 2.07-1.92 (m, 2H), 1.82-1.76 (m, 1H), 1.68-1.55 (m, 3H), 1.48-1.43 (m, 1H); $^{13}$C NMR: δ 149.3, 147.0, 138.9, 138.54, 133.3, 129.3, 128.9, 128.5, 128.4, 124.6, 111.7, 110.7, 65.3, 52.3, 40.4, 36.6, 32.7, 29.1, 21.90, 21.0; m/z: Calcd for C$_{22}$H$_{25}$ClN$_2$O$_2$S [M+H]$^+$ 417.1398. Found 417.1404; IR: 2927, 2856, 1491, 1476, 1395, 1329, 1276, 1161, 1014, 827, 752 cm$^{-1}$. 4-Chloro-N-[2-(6-methoxy-4-methylidene-2,3,4,4a,9,9a-hexahydro-1H-carbazol-4a-yl)ethyl]benzene-1-sulfonamide (6c): TLC (hexanes:ethyl acetate, 3:1 v/v): R$_f$=0.40; colorless oil, 97%; $^1$H NMR: δ 7.75 (d, J=8.8 Hz, 2H), 7.47 (d, J=8.8 Hz, 1H), 6.81-6.75 (brm, 1H), 6.67 (dd, J=8.5, 2.5 Hz, 1H), 6.56 (s, 1H), 5.56 (brs, 1H), 5.01 (s, 1H), 4.77 (s, 1H), 3.79 (s, 1H), 3.76 (s, 3H), 3.0-3.02 (m, 1H), 2.84-2.81 (m, 1H), 2.24-2.19 (m, 1H), 2.12-2.04 (m, 2H), 2.02-1.97 (m, 1H), 1.96-1.88 (m, 1H), 1.71-1.65 (m, 1H), 1.64-1.56 (m, 1H), 1.50-1.44 (m, 1H); $^{13}$C NMR: δ 138.9, 138.4, 129.5, 129.4, 129.3, 128.5, 112.9, 112.5, 110.7, 65.4, 55.9, 53.0, 40.3, 36.4, 32.7, 28.6, 22.0; m/z: Calcd for C$_{22}$H$_{25}$ClN$_2$O$_3$S [M+H]$^+$ 433.1347. Found 433.1336; IR: 3286, 3087, 2927, 2854, 1930, 1637, 1587, 1488, 1435, 1329, 1278, 1263, 1219, 1161, 1094, 828 cm$^{-1}$. 4-Chloro-N-[2-(6-fluoro-4-methylidene-2,3,4,4a,9,9a-hexahydro-1H-carbazol-4a-yl)ethyl]benzene-1-sulfonamide (6d): TLC (hexanes:ethyl acetate, 3:1 v/v): R$_f$=0.20; colorless oil, 84%; $^1$H NMR: δ 7.75 (d, J=8.6 Hz, 2H), 7.48 (d, J=8.6 Hz, 2H), 6.76 (td, J=8.8, 2.6 Hz, 1H), 6.64 (dd, J=8.3, 2.6 Hz, 1H), 6.58 (dd, J=8.4, 4.3 Hz, 1H), 5.16 (t, J=6.1 Hz, 1H), 4.94 (s, 1H), 4.67 (s, 1H), 3.63 (t, J=5.0 Hz, 1H), 3.04-2.96 (m, 1H), 2.91-2.83 (m, 1H), 2.23-2.09 (m, 2H), 2.09-2.01 (m, 1H), 1.96 (ddd, J=14.1, 8.4, 5.6 Hz, 1H), 1.80 (tt, J=9.5, 4.9 Hz, 1H), 1.70-1.57 (m, 1H), 1.52-1.45 (m, 1H); $^{13}$C NMR: δ 148.8, 139.1, 138.4, 129.4, 128.5, 114.3, 114.0, 112.1, 111.6, 111.3, 111.1, 111.0, 65.7, 52.5, 40.2, 36.2, 32.5, 28.7, 21.8; m/z: Calcd for C$_{21}$H$_{22}$ClFN$_2$O$_2$S [M+H]$^+$ 421.1147. Found 421.1147; IR: 3734, 2929, 1507, 1485, 1276, 1260, 1160, 1260, 1160, 1093, 1014, 828, 751 cm$^{-1}$. 4-Chloro-N-[2-(4-methylidene-2,3,4,4a,9,9a-hexahydro-1H-carbazol-4a-yl)ethyl]benzene-1-sulfonamide (6e): TLC (hexanes:ethyl acetate, 3:1 v/v): R$_f$=0.20; colorless oil, 95%; $^1$H NMR: δ 7.73 (d, J=8.6 Hz, 2H), 7.46 (d, J=8.6 Hz, 2H), 7.06 (td, J=7.6, 1.3 Hz, 1H), 6.91 (dd, J=7.3, 1.3 Hz, 1H), 6.75 (td, J=7.4, 1.0 Hz, 1H), 6.66 (d, J=7.8 Hz, 1H), 5.08 (t, J=6.0 Hz, 1H), 4.92 (d, J=1.6 Hz, 1H), 4.67 (d, J=1.3 Hz, 1H), 3.60 (t, J=4.9 Hz, 1H), 3.06-2.96 (m, 1H), 2.93-2.87 (m, 1H), 2.15 (q, J=5.5 Hz, 2H), 2.09-1.93 (m, 2H), 1.85-1.74 (m, 1H), 1.71-1.57 (m, 2H), 1.52-1.47 (m, 1H); $^{13}$C NMR: δ 149.5, 149.3, 139.0, 138.5, 133.0, 129.3, 128.5, 128.0, 124.1, 119.3, 111.8, 110.7, 65.2, 52.2, 40.4, 36.4, 32.5, 28.8, 21.8; m/z: Calcd for C$_{21}$H$_{23}$ClN$_2$O$_2$S [M+H]$^+$ 403.1242. Found 403.1241; IR: 3287, 2930, 2856, 1606, 1478, 1464, 1396, 1328, 1276, 1261, 1160, 1094, 1014, 902, 828, 751 cm$^{-1}$. 4-Chloro-N-(2-{7-methylidene-6bH,7H,8H,9H,10H,10aH,11H-benzo[a]carbazol-6b-yl}ethyl)benzene-1-sulfonamide (6f): TLC (hexanes:ethyl acetate, 3:1 v/v): R$_f$=0.40; colorless oil, 90%; $^1$H NMR: δ 7.81 (dt, J=6.9, 3.5 Hz, 1H), 7.63 (dd, J=6.2, 3.3 Hz, 1H), 7.56 (d, J=8.6 Hz, 1H), 7.46 (dp, J=6.7, 3.5 Hz, 2H), 7.30 (d, J=8.2 Hz, 1H), 7.25 (d, J=8.5 Hz, 2H), 7.08 (d, J=8.2 Hz, 1H), 5.39 (t, J=6.3 Hz, 1H), 4.97 (s, 1H), 4.79 (s, 1H), 3.80 (t, J=5.0 Hz, 1H), 2.97 (dtd, J=13.0, 7.3, 5.6 Hz, 1H), 2.71 (dtd, J=12.9, 7.5, 5.1 Hz, 1H), 2.22 (ddd, J=13.7, 8.2, 5.3 Hz, 1H), 2.16-2.00 (m, 3H), 1.86 (tt, J=10.1, 5.3 Hz, 1H), 1.65 (dtt, J=14.9, 9.7, 4.6 Hz, 2H), 1.50 (dtd, J=11.3, 6.4, 3.3 Hz, 1H).; $^{13}$C NMR: δ 149.5, 145.4, 138.8, 138.1, 133.8, 129.2, 128.6, 128.3, 126.3, 125.6, 125.1, 122.2, 121.4, 121.0, 119.6, 111.6, 65.7, 53.1, 40.5, 37.1, 32.5, 29.7, 29.5, 21.1; m/z: Calcd for C$_{25}$H$_{25}$ClN$_2$O$_2$S [M+H]$^+$ 453.1398. Found 453.1404; IR: 3355, 3289, 3056, 2929, 2856, 1718, 1638, 1586, 1519, 1445, 1265, 1161, 1094, 1014, 901, 803, 752 cm$^{-1}$. N-[2-(8-bromo-4-methylidene-2,3,4,4a,9,9a-hexahydro-1H-carbazol-4a-yl)ethyl]-4-chlorobenzene-1-sulfonamide (6g): TLC (hexanes:ethyl acetate, 3:1 v/v): R$_f$=0.40; colorless oil, 83%; $^1$H NMR: δ 7.85-7.64 (m, 2H), 7.48 (d, J=8.8 Hz, 2H), 7.22 (d, J=8.0 Hz, 1H), 6.86 (d, J=7.2 Hz, 1H), 6.63 (t, J=7.6 Hz, 1H), 4.94 (s, 1H), 4.88 (br. t, J=6.2 Hz, 1H), 4.68 (s, 1H), 3.71-3.63 (m, 1H), 3.06-2.85 (m, 2H), 2.16 (q, J=5.6 Hz, 2H), 2.07 (q, J=9.1, 8.3 Hz, 1H), 1.99 (ddd, J=14.2, 8.5, 5.6 Hz, 1H), 1.82 (ddt, J=12.3, 8.3, 5.0 Hz, 1H), 1.67 (dtt, J=16.8, 9.8, 5.0 Hz, 2H), 1.50 (ddt, J=13.8, 10.2, 6.1 Hz, 1H); $^{13}$C NMR: δ 148.6, 139.1, 138.4, 130.6, 129.4, 128.5, 122.9, 120.2, 112.1, 64.7, 53.4, 40.3, 36.4, 32.4, 28.7, 21.5; m/z: Calcd for C$_{21}$H$_{22}$BrClN$_2$O$_2$S [M+H]$^+$ 481.0347. Found 491.0355; IR: 3373, 3054, 2927, 2853, 1588, 1454, 1422, 1265, 1164, 1098, 897, 829 cm$^{-1}$. N-[2-(7-bromo-4-methylidene-2,3,4,4a,9,9a-hexahydro-1H-carbazol-4a-yl)ethyl]-4-chlorobenzene-1-sulfonamide (6h): TLC (hexanes:ethyl acetate, 3:1 v/v): R$_f$=0.30; colorless oil, 86%; $^1$H NMR: δ 7.73 (d, J=8.5 Hz, 2H), 7.49 (d, J=8.5 Hz, 2H), 6.89-6.82 (m, 1H), 6.78-6.64 (m, 2H), 4.93 (s, 1H), 4.76 (t, J=6.3 Hz, 1H), 4.67 (s, 1H), 3.70 (brs, 1H), 3.62 (t, J=4.8 Hz, 1H), 3.03-2.84 (m, 2H), 2.24-2.10 (m, 2H), 2.07-2.01 (m, 1H), 1.99-1.93 (m, 1H), 1.84-1.72 (m, 1H), 1.69-1.60 (m, 2H), 1.53-1.46 (m, 1H); $^{13}$C NMR: δ 151.2, 148.8, 139.1, 138.4, 132.0, 129.4, 128.5, 125.3, 121.7, 121.6, 113.4, 112.0, 65.3, 51.8, 40.2, 36.3, 32.3, 28.7, 21.5; m/z: Calcd for C$_{21}$H$_{22}$BrClN$_2$O$_2$S [M+H]$^+$ 481.0347. Found 481.0350; IR: 3367, 3285, 2925, 2854, 1713, 1600, 1478, 1434, 1328, 1161, 1094, 1014, 901, 828, 738 cm$^{-1}$. N-(2-((4aS,9aS)-5-bromo-4-methylene-2,3,4,4a,9,9a-hexahydro-1H-carbazol-4a-yl)ethyl)-4-chlorobenzenesulfonamide (6i): TLC (hexanes:ethyl acetate, 3:1 v/v): R$_f$=0.30; colorless oil, 73%; $^1$H NMR: δ 7.73 (d, J=8.5 Hz, 2H), 7.49 (d, J=8.5 Hz, 2H), 6.89-6.82 (m, 1H), 6.78-6.64 (m, 2H), 4.93 (s, 1H), 4.76 (t, J=6.3 Hz, 1H), 4.67 (s, 1H), 3.70 (brs, 1H), 3.62 (t, J=4.8 Hz, 1H), 3.03-2.84 (m, 2H), 2.24-2.10 (m, 2H), 2.07-2.01 (m, 1H), 1.99-1.93 (m, 1H), 1.84-1.72 (m, 1H), 1.69-1.60 (m, 2H), 1.53-1.46 (m, 1H); $^{13}$C NMR: δ 153.1, 150.6, 149.0, 136.1, 135.4, 131.4, 130.4, 129.5, 128.5, 123.2, 111.9, 111.3, 64.8, 50.6, 41.2, 39.9, 32.8, 29.3, 22.4; m/z: Calcd for C$_{21}$H$_{21}$BrClN$_2$O$_2$SNa [M+Na]$^+$ 503.0166. Found 503.0175; IR: 2954, 2923, 2853, 1713, 1662, 1571, 1462, 1377, 1331, 1278, 1162, 1096, 1014, 906, 827 cm$^{-1}$. 4-Chloro-N-[2-(6-chloro-8-fluoro-4-methylidene-2,3,4,4a,9,9a-hexahydro-1H-carbazol-4a-yl)ethyl]benzene-1-sulfonamide (6j): TLC (hexanes:ethyl acetate, 3:1 v/v): R$_f$=0.50; colorless oil, 89%; $^1$H NMR: δ 7.77 (d, J=8.6 Hz, 2H), 7.50 (d, J=8.5 Hz, 2H), 6.89 (dd, J=9.9, 1.9 Hz, 1H), 6.72 (d, J=1.9 Hz, 1H), 4.96 (s, 1H), 4.83 (t, J=6.2 Hz, 1H), 4.67 (s, 1H), 3.70 (s, 1H), 3.01-2.89 (m, 2H), 2.21-2.12 (m, 2H), 2.10-2.04 (m, 1H), 2.01-1.95 (m, 1H), 1.86-1.80 (m, 1H), 1.71-1.65 (m, 3H), 1.56-1.48 (m, 1H); $^{13}$C NMR: δ 148.1, 147.3, 139.2, 138.3, 137.7, 137.6, 135.8, 135.6, 129.5, 128.5, 120.0, 120.0, 115.5, 115.2, 112.4, 66.0, 52.9, 40.1, 36.0, 32.4, 31.9, 28.6, 21.6; m/z: Calcd for C$_{21}$H$_{21}$Cl$_2$FN$_2$O$_2$S [M+H]$^+$ 455.0758. Found 455.0760; IR: 3054, 2986, 2926, 2853, 1584, 1422, 1265, 1159, 1013, 975, 896, 740 cm$^{-1}$. 4-Chloro-N-[2-(6,8-dichloro-4-methylidene-2,3,4,4a,9,9a-hexahydro-1H-carbazol-4a-yl)ethyl]benzene-1-sulfonamide (6k): TLC (hexanes:ethyl acetate, 3:1 v/v): R$_f$=0.60; colorless oil, 88%; $^1$H NMR: δ 7.76 (d, J=8.6 Hz, 2H), 7.50 (d, J=8.6 Hz, 2H), 7.08 (d, J=1.9 Hz, 1H), 6.79 (d, J=1.9 Hz, 1H), 4.95 (d, J=1.4 Hz, 1H), 4.81 (t, J=6.3 Hz, 1H), 4.67 (s, 1H), 3.89 (brs, 1H), 3.69 (t, J=4.8 Hz, 1H), 3.02-2.88 (m, 2H), 2.19-2.14 (m, 2H), 2.11-2.01 (m, 1H), 1.99-1.93 (m, 1H), 1.87-1.77 (m, 1H), 1.73-1.64 (m, 2H), 1.53-1.50 (m, 1H); $^{13}$C NMR: δ 147.9, 145.7, 139.3, 138.3, 135.8, 129.5, 128.5, 127.4, 123.5, 122.7, 116.0, 112.4, 65.2, 53.3, 40.1, 36.1, 32.3, 28.5, 21.4; m/z: Calcd for C$_{21}$H$_{21}$Cl$_3$N$_2$NaO$_2$S [M+Na]$^+$ 493.0282. Found 493.0292; IR: 3360, 3291, 2926, 2855, 1714, 1638, 1580, 1464, 1329, 1161, 1094, 904, 754 cm$^{-1}$. N-[2-(6-bromo-8-fluoro-4-methylidene-2,3,4,4a,9,9a-hexahydro-1H-carbazol-4a-yl)ethyl]-4-chlorobenzene-1-sulfonamide (6l): TLC (hexanes:ethyl acetate, 3:1 v/v): R$_f$=0.20; colorless oil, 77%; $^1$H NMR: δ 7.76 (d, J=8.6 Hz, 2H), 7.50 (d, J=8.6 Hz, 2H), 7.02 (dd, J=9.5, 1.7 Hz, 1H), 6.84 (d, J=1.7 Hz, 1H), 4.96 (d, J=1.4 Hz, 1H), 4.76 (t, J=6.3 Hz, 1H), 4.67 (s, 1H), 3.74 (brs, 1H), 3.69 (t, J=4.9 Hz, 1H), 3.04-2.85 (m, 2H), 2.21-2.12 (m, 2H), 2.10-2.03 (m, 1H), 2.02-1.94 (m, 1H), 1.86-1.78 (m, 1H), 1.72-1.63 (m, 2H), 1.55-1.49 (m, 1H); $^{13}$C NMR: δ 150.8, 148.1, 147.5, 139.2, 138.3, 138.2, 138.2, 136.3, 136.1, 129.5, 128.5, 128.5, 128.1, 122.8, 122.8, 118.2, 117.9, 112.4, 109.7, 109.6, 66.0, 52.9, 52.9, 40.1, 36.0, 32.4, 28.5, 21.6; m/z: Calcd for C21H22BrClFN2O2S [M+H]$^+$ 499.0252. Found 499.0258; IR: 3359, 3303, 2927, 2854, 1705, 1623, 1588, 1520, 1472, 1396, 1330, 1261, 1161, 1094, 1014, 903, 828, 753 cm$^{-1}$. 4-chloro-N-[2-(5,8-dibromo-4-methylidene-2,3,4,4a,9,9a-hexahydro-1H-carbazol-4a-yl)ethyl]benzene-1-sulfonamide (6n): TLC (hexanes:ethyl acetate, 3:1 v/v): R$_f$=0.40; colorless oil, 75%; $^1$H NMR: δ 7.73 (d, J=8.6 Hz, 2H), 7.46 (d, J=8.6 Hz, 2H), 7.05 (d, J=8.5 Hz, 1H), 6.67 (d, J=8.5 Hz, 1H), 4.94 (s, 1H), 4.81 (t, J=6.3 Hz, 1H), 4.76 (s, 1H), 3.97 (s, 1H), 3.77 (s, 1H), 3.01-2.81 (m, 2H), 2.45 (ddd, J=14.1, 9.1, 5.0 Hz, 1H), 2.24-2.15 (m, 2H), 2.09 (ddd, J=13.9, 9.2, 6.9 Hz, 1H), 1.83-1.67 (m, 2H), 1.61 (dt, J=8.4, 3.4 Hz, 2H). N-[2-(5-bromo-8-fluoro-4-methylidene-2,3,4,4a,9,9a-hexahydro-1H-carbazol-4a-yl)ethyl]-4-chlorobenzene-1-sulfonamide (6m): TLC (hexanes:ethyl acetate, 3:1 v/v): R$_f$=0.40; colorless oil, 75%; $^1$H NMR: δ 7.73 (d, J=8.5 Hz, 2H), 7.46 (d, J=8.5 Hz, 2H), 6.73 (d, J=6.9 Hz, 2H), 4.94 (s, 1H), 4.89 (t, J=6.3 Hz, 1H), 4.74 (s, 1H), 3.81 (brs, 1H), 3.77 (t, J=3.7 Hz, 1H), 3.02-2.93 (m, 1H), 2.86 (ddt, J=13.0, 8.9, 6.6 Hz, 1H), 2.45 (ddd, J=14.0, 9.0, 4.9 Hz, 1H), 2.24-2.15 (m, 2H), 2.10 (ddd, J=13.5, 9.2, 7.0 Hz, 1H), 1.81-1.74 (m, 1H), 1.70 (dt, J=14.6, 3.7 Hz, 2H), 1.66-1.62 (m, 2H). Benzyl N-[2-(6-bromo-4-methylidene-2,3,4,4a,9,9a-hexahydro-1H-carbazol-4a-yl)ethyl]carbamate (10a): TLC (hexanes:ethyl acetate, 2:1 v/v): R$_f$=0.30; colorless oil, 95%; $^1$H NMR: δ 7.41-7.31 (m, 5H), 7.15 (d, J=7.1 Hz, 2H), 6.55 (d, J=8.6 Hz, 1H), 5.09 (s, 2H), 4.94 (s, 1H), 4.83 (brs, 1H), 4.71 (s, 1H), 3.74 (t, J=4.4 Hz, 1H), 3.39-3.26 (m, 1H), 3.22-3.15 (m, 1H), 2.21-2.19 (m, 2H), 2.10-2.04 (m, 1H), 2.00-1.94 (m, 1H), 1.87-1.80 (m, 1H), 1.71-1.66 (m, 3H), 1.57-1.52 (m, 1H); $^{13}$C NMR: δ 156.3, 149.0, 148.9, 136.3, 130.5, 128.5, 128.1, 127.2, 112.0, 111.7, 110.4, 66.7, 65.3, 52.3, 38.0, 35.7, 32.3, 28.2, 21.8; m/z: Calcd for C23H25BrN2O2Na [M+Na]$^+$ 464.1075. Found 464.1083; IR: 3344, 3032, 2924, 2853, 1711, 1601, 1519, 1473, 1375, 1259, 1102, 902, 807 cm$^{-1}$. 2-(6-Bromo-4-methylidene-2,3,4,4a,9,9a-hexahydro-1H-carbazol-4a-yl)ethan-1-amine (11a): TLC (chloroform:methanol, 10:1 v/v): R$_f$=0.10; colorless oil, 72%; $^1$H NMR: δ 7.20 (d, J=2.0 Hz, 1H), 7.15 (dd, J=8.3, 2.1 Hz, 1H), 6.55 (d, J=8.2 Hz, 1H), 4.88 (s, 1H), 4.60 (d, J=1.5 Hz, 1H), 3.72 (d, J=3.2 Hz, 1H), 3.64 (s, 1H), 2.86-2.80 (m, 1H), 2.73-2.67 (m, 1H), 2.25-2.16 (m, 3H), 2.01-1.98 (m, 1H), 1.94-1.88 (m, 1H), 1.85-1.79 (m, 1H), 1.77-1.67 (m, 2H), 1.63-1.58

(m, 1H); ¹³C NMR: δ 149.8, 149.0, 137.1, 130.2, 127.4, 111.6, 111.6, 110.2, 65.6, 52.5, 39.3, 39.0, 32.3, 29.7, 27.6, 22.0; m/z: Calcd for C₁₅H₂₀BrN₂ [M+H]⁺ 307.0804. Found 307.0816; IR: 3367, 2960, 2924, 2853, 1729, 1661, 1600, 1464, 1261, 1092, 870, 802 cm⁻¹. N-[2-(6-bromo-4-methylidene-2,3,4,4a,9,9a-hexahydro-1H-carbazol-4a-yl)ethyl]-2,2,2-trifluoroacetamide (12a): TLC (hexanes:ethyl acetate, 3:1 v/v): R$_f$=0.40; colorless oil, 82%; ¹H NMR: δ 7.20 (dd, J=8.2, 2.0 Hz, 1H), 7.14 (d, J=2.0 Hz, 1H), 6.72 (brs, 1H), 6.60 (d, J=8.2 Hz, 1H), 5.03 (s, 1H), 4.83 (s, 1H), 3.69 (t, J=5.2 Hz, 1H), 3.46-3.34 (m, 2H), 2.27-2.21 (m, 1H), 2.19-2.14 (m, 1H), 2.13-2.00 (m, 2H), 1.90-1.84 (m, 1H), 1.72-1.60 (m, 2H), 1.53-1.47 (m, 1H); ¹³C NMR: δ 156.8, 148.3, 135.5, 130.9, 127.0, 112.4, 112.1, 65.4, 52.3, 36.9, 35.4, 32.5, 29.0, 21.6; m/z: Calcd for C₁₇H₁₉BrF₃N₂O [M+H]⁺ 403.0627. Found 403.0622; IR: 3322, 2957, 2928, 2861, 1663, 1599, 1530, 1463, 1378, 1008, 823 cm⁻¹. N-[2-(6-bromo-4-methylidene-2,3,4,4a,9,9a-hexahydro-1H-carbazol-4a-yl)ethyl]pentanamide (12b): TLC (chloroform:methanol, 10:1 v/v): R$_f$=0.75; colorless oil, 82%; ¹H NMR: δ 7.16 (d, J=6.7 Hz, 2H), 6.55 (d, J=8.9 Hz, 1H), 5.45 (brs, 1H), 4.94 (d, J=1.4 Hz, 1H), 4.72 (s, 1H), 3.99 (brs, 1H), 3.76 (t, J=4.4 Hz, 1H), 3.44-3.38 (m, 1H), 3.28-3.16 (m, 1H), 2.36 (t, J=7.5 Hz, 1H), 2.23-2.20 (m, 1H), 2.14-2.08 (m, 2H), 2.08-2.00 (m, 1H), 1.99-1.92 (m, 1H), 1.87-1.79 (m, 1H), 1.75-1.66 (m, 2H), 1.65-1.57 (m, 2H), 1.33 (dq, J=14.6, 7.3 Hz, 2H), 0.91 (t, J=7.3 Hz, 3H); ¹³C NMR: δ 173.1, 140.4, 131.5, 131.0, 114.3, 104.5, 66.4, 52.0, 38.3, 36.6, 36.2, 34.9, 32.7, 29.8, 27.7, 27.2, 22.6, 14.1; m/z: Calcd for C₂₀H₂₇BrN₂O [M+H]⁺ 391.1380. Found 391.1363; IR: 3312, 3084, 2955, 2930, 2860, 1727, 1661, 1587, 1542, 1467, 1392, 1325, 1254, 1202, 909, 821 cm⁻¹. N-[2-(6-bromo-4-methylidene-2,3,4,4a,9,9a-hexahydro-1H-carbazol-4a-yl)ethyl]-4-chlorobenzamide (12c): TLC (hexanes:ethyl acetate, 1:1 v/v): R$_f$=0.70; colorless oil, 97%; ¹H NMR: δ 7.59 (d, J=8.5 Hz, 2H), 7.39 (d, J=8.5 Hz, 2H), 7.20 (d, J=2.0 Hz, 1H), 7.17 (dd, J=8.2, 2.0 Hz, 1H), 6.57 (d, J=8.2 Hz, 1H), 6.24 (brs, 1H), 4.98 (d, J=1.5 Hz, 1H), 4.77 (s, 1H), 3.80 (t, J=4.5 Hz, 1H), 3.60-3.57 (m, 1H), 3.52-3.42 (m, 1H), 2.32-2.20 (m, 2H), 2.19-2.15 (m, 1H), 2.12-2.06 (m, 1H), 1.88-1.81 (m, 1H), 1.74-1.67 (m, 2H), 1.58-1.53 (tm, 1H); ¹³C NMR: δ 166.2, 149.2, 149.1, 137.6, 136.2, 132.8, 130.6, 128.8, 128.8, 128.2, 127.1, 112.1, 111.8, 110.5, 65.2, 52.3, 37.1, 35.3, 32.3, 28.4, 21.6; m/z: Calcd for C₂₂H₂₂BrClN₂NaO [M+Na]⁺ 467.0496. Found 467.0498; IR: 3309, 2927, 2855, 1636, 1597, 1567, 1544, 1485, 1316, 1262, 1094, 1013, 976 cm⁻¹. N-[2-(6-bromo-4-methylidene-2,3,4,4a,9,9a-hexahydro-1H-carbazol-4a-yl)ethyl]benzenesulfonamide (12d): TLC (hexanes:ethyl acetate, 1:1 v/v): R$_f$=0.50; colorless oil, 77%; ¹H NMR: δ 7.87-7.79 (m, 2H), 7.62-7.57 (m, 1H), 7.53 (t, J=7.6 Hz, 2H), 7.13 (dd, J=8.2, 2.0 Hz, 1H), 6.98 (d, J=2.0 Hz, 1H), 6.52 (d, J=8.2 Hz, 1H), 4.91 (s, 1H), 4.89 (brs, 1H), 4.63 (s, 1H), 3.62 (t, J=4.8 Hz, 1H), 3.04-2.91 (m, 2H), 2.15-2.13 (m, 2H), 2.05-1.97 (m, 1H), 1.97-1.90 (m, 1H), 1.79-1.74 (m, 1H), 1.66-1.61 (m, 2H), 1.53-1.45 (m, 1H); ¹³C NMR: δ 148.8, 148.7, 139.8, 135.6, 132.7, 130.6, 129.2, 128.8, 128.2, 127.0, 112.1, 111.8, 110.6, 65.3, 52.3, 40.2, 36.1, 32.4, 28.5, 21.7; m/z: Calcd for C₂₁H₂₃BrN₂O₂S [M+H]⁺ 447.0736. Found 448.0747; IR: 3361.8, 2926, 2855, 1638, 1598, 1475, 1324, 1159, 1092, 902, 689 cm⁻¹. N-[2-(6-bromo-4-methylidene-2,3,4,4a,9,9a-hexahydro-1H-carbazol-4a-yl)ethyl]-4-methylbenzene-1-sulfonamide (12e): TLC (hexanes:ethyl acetate, 3:1 v/v): R$_f$=0.20; colorless oil, 80%; ¹H NMR: δ 7.71 (d, J=8.3 Hz, 2H), 7.33 (d, J=8.3 Hz, 2H), 7.30 (dd, J=8.2, 2.1 Hz, 1H), 6.94 (d, J=2.1 Hz, 1H), 5.09 (d, J=1.5 Hz, 1H), 4.80 (d, J=2.0 Hz, 1H), 3.97 (dd, J=8.1, 5.8 Hz, 1H), 3.55 (t, J=6.2 Hz, 1H), 2.79-2.72 (m, 1H), 2.55-2.49 (m, 1H), 2.46 (s, 3H), 2.23 (dt, J=15.2, 5.0 Hz, 1H), 2.05-2.01 (m, 1H), 1.96-1.86 (m, 1H), 1.71-1.55 (m, 4H), 1.52-1.46 (1, 1H); ¹³C NMR: δ 144.7, 136.7, 135.9, 131.8, 130.1, 127.0, 126.8, 126.7, 117.1, 113.6, 67.8, 52.1, 38.7, 38.4, 31.8, 29.7, 21.6; m/z: Calcd for C₂₂H₂₄BrN₂O₂SK [M+K]⁺ 499.0452. Found 499.0455; IR: 3292, 3064, 2924, 2854, 1724, 1683, 1597, 1465, 1356, 1334, 1184, 1162, 1094, 908, 815, 665 cm⁻¹. N-[2-(6-bromo-4-methylidene-2,3,4,4a,9,9a-hexahydro-1H-carbazol-4a-yl)ethyl]-4-fluorobenzene-1-sulfonamide (12f): TLC (hexanes:ethyl acetate, 3:1 v/v): R$_f$=0.20; colorless oil, 70%; ¹H NMR: δ 7.90 (dd, J=8.6, 5.0 Hz, 2H), 7.81 (dd, J=8.8, 5.1 Hz, 2H), 7.50 (d, J=8.5 Hz, 1H), 7.39-7.34 (m, 1H), 6.98 (d, J=2.0 Hz, 1H), 5.11 (s, 1H), 4.85 (s, 1H), 4.17 (brs, 4.12 (dd, J=8.0, 5.7 Hz, 1H), 2.81-2.76 (m, 1H), 2.73-2.66 (m, 1H), 2.28-2.17 (m, 2H), 2.08-1.98 (m, 1H), 1.93 (q, J=8.9, 8.4 Hz, 1H), 1.95-1.89 (m, 1H), 1.73-1.64 (m, 2H), 1.44-1.41 (m, 1H); ¹³C NMR: δ 144.9, 139.3, 138.4, 131.8, 129.8, 129.7, 129.6, 129.6, 127.0, 117.0, 116.9, 116.68, 116.7, 116.6, 116.3, 113.5, 68.3, 52.1, 39.0, 38.2, 31.6, 30.0, 20.0; m/z: Calcd for C₂₁H₂₁BrFN₂O₂SNa [M+Na]⁺ 487.0462. Found 487.0486; IR: 3298, 3077, 2926, 2855, 1712, 1651, 1592, 1493, 1469, 1358, 1337, 1293, 1238, 907, 839, 738 cm⁻¹. 4-Bromo-N-[2-(6-bromo-4-methylidene-2,3,4,4a,9,9a-hexahydro-1H-carbazol-4a-yl)ethyl]benzene-1-sulfonamide (12h): TLC (hexanes:ethyl acetate, 3:1 v/v): R$_f$=0.30; colorless oil, 81%; ¹H NMR: δ 7.76-7.59 (m, 4H), 7.19 (d, J=8.3 Hz, 1H), 7.02 (d, J=2.0 Hz, 1H), 6.63 (s, 1H), 4.98 (s, 1H), 4.71 (s, 1H), 3.81-3.68 (m, 1H), 3.02-2.90 (m, 2H), 2.26-2.16 (m, 1H), 2.15-2.09 (m, 1H), 2.09-2.01 (m, 1H), 2.00-1.94 (m, 1H), 1.70-1.64 (m, 2H), 1.50-1.44 (m, 1H); ¹³C NMR: δ 149.7, 144.9, 139.3, 139.0, 138.3, 132.9, 132.1, 131.9, 128.4, 127.1, 117.1, 116.7, 114.9, 68.5, 52.1, 39.3, 32.0, 31.6, 30.3, 20.0; m/z: Calcd for C₂₁H₂₂Br₂N₂O₂S [M+H]⁺ 524.9842. Found 524.9839; IR: 3290, 3088, 2924, 2853, 1712, 1638, 1574, 1468, 1389, 1359, 1339, 1231, 1167, 1092, 1068, 1010, 908, 821, 738 cm⁻¹. N-[2-(6-bromo-4-methylidene-2,3,4,4a,9,9a-hexahydro-1H-carbazol-4a-yl)ethyl]-4-iodobenzene-1-sulfonamide (12i): TLC (hexanes:ethyl acetate, 3:1 v/v): R$_f$=0.50; colorless oil, 92%; ¹H NMR: δ 7.88 (d, J=8.5 Hz, 2H), 7.53 (d, J=8.5 Hz, 2H), 7.15 (dd, J=8.3, 2.0 Hz, 1H), 6.99 (d, J=2.0 Hz, 1H), 6.53 (d, J=8.2 Hz, 1H), 4.94 (d, J=1.3 Hz, 1H), 4.92 (brs, 1H), 4.68 (d, J=1.2 Hz, 1H), 3.62 (t, J=4.9 Hz, 1H), 3.01-2.86 (m, 2H), 2.21-2.10 (m, 2H), 2.02-2.01 (m, 1H), 1.98-1.92 (m, 1H), 1.82-1.76 (m, 1H), 1.67-1.57 (m, 2H), 1.51-1.46 (m, 1H); ¹³C NMR: δ 148.8, 148.6, 139.6, 138.4, 135.4, 130.7, 128.4, 127.0, 112.2, 111.9, 110.7, 100.0, 65.4, 52.3, 40.2, 36.3, 32.4, 29.7, 21.6; m/z: Calcd for C₂₁H₂₂BrIN₂O₂SNa [M+Na]⁺ 594.9522. Found 594.9523; IR: 3283, 3082, 2926, 2855, 1716, 1636, 1601, 1570, 1474, 1384, 1329, 1262, 1161, 1090, 1006, 816, 737 cm⁻¹. N-[2-(6-bromo-4-methylidene-2,3,4,4a,9,9a-hexahydro-1H-carbazol-4a-yl)ethyl]-3,4-dichlorobenzene-1-sulfonamide (12j): TLC (hexanes:ethyl acetate, 3:1 v/v): R$_f$=0.50; colorless oil, 72%; ¹H NMR: δ 7.91 (d, J=2.0 Hz, 1H), 7.63 (dd, J=8.4, 2.1 Hz, 1H), 7.60 (s, 1H), 7.15 (dd, J=8.3, 2.0 Hz, 1H), 7.00 (d, J=2.0 Hz, 1H), 6.54 (d, J=8.3 Hz, 1H), 5.12 (t, J=6.3 Hz, 1H), 4.97 (d, J=1.4 Hz, 1H), 4.72 (s, 1H), 3.74 (s, 1H), 3.63 (t, J=5.1 Hz, 1H), 3.07-2.95 (m, 1H), 2.93-2.83 (m, 1H), 2.21-2.11 (m, 2H), 2.08-2.01 (m, 1H), 2.00-1.94 (m, 1H), 1.84-1.77 (m, 1H), 1.68-1.56 (m, 2H), 1.53-1.43 (m, 1H); ¹³C NMR: δ 148.7, 148.4, 139.7, 137.5, 135.3, 133.8, 131.2, 131.2, 130.8, 128.9, 128.6, 126.1, 125.6, 112.2, 111.9, 110.9, 65.4, 52.4, 40.3, 36.5, 32.5, 29.0, 21.6; m/z: Calcd for C₂₁H₂₁BrCl₂N₂O₂S [M+H]⁺ 514.9957. Found 514.9963; IR: 2268, 2960, 2337, 1720, 1601, 1455, 1370, 1260, 1164, 1032, 801, 700 cm⁻¹. N-[2-(6-bromo-4-methylidene-2,3,4,4a,9,9a-hexahydro-1H-carbazol-4a-yl)ethyl]-2,4-dichlorobenzene-1-sulfonamide (12k): TLC (hexanes:ethyl acetate, 2:1 v/v): $R_f$=0.40; colorless oil, 77%; ¹H NMR: δ 8.16-8.03 (m, 1H), 7.87 (dd, J=6.9, 2.4 Hz, 1H), 7.82-7.67 (m, 2H), 7.14 (dd, J=8.3, 2.0 Hz, 1H), 7.02 (d, J=2.1 Hz, 1H), 6.55 (d, J=8.3 Hz, 1H), 5.82 (t, J=6.1 Hz, 1H), 4.96 (s, 1H), 4.71 (s, 1H), 3.68 (t, J=5.0 Hz, 1H), 3.21-2.99 (m, 3H), 2.26-2.15 (m, 2H), 2.15-2.08 (m, 1H), 2.06-2.00 (m, 1H), 1.87-1.80 (m, 1H), 1.74-1.62 (m, 2H), 1.55-1.46 (m, 1H); ¹³C NMR: δ 148.9, 141.7, 139.5, 135.3, 132.3, 131.3, 130.7, 127.6, 126.8, 112.1, 111.9, 111.0, 65.2, 52.3, 40.2, 36.2, 32.4, 31.1, 21.8; m/z: Calcd for $C_{21}H_{21}BrCl_2N_2NaO_2S$ [M+Na]⁺ 536.9776. Found 536.9799; IR: 3292, 3087, 2924, 2853, 1712, 1637, 1600, 1572, 1555, 1456, 1373, 1337, 1260, 1166, 1102, 903, 817, 624 cm⁻¹. N-[2-(6-bromo-4-methylidene-2,3,4,4a,9,9a-hexahydro-1H-carbazol-4a-yl)ethyl]-4-cyanobenzene-1-sulfonamide (12l): TLC (hexanes:ethyl acetate, 3:1 v/v): $R_f$=0.20; colorless oil, 67%; ¹H NMR: δ 7.93 (d, J=8.4 Hz, 2H), 7.83 (d, J=8.4 Hz, 2H), 7.16 (dd, J=8.3, 2.0 Hz, 1H), 6.99 (d, J=2.0 Hz, 1H), 6.54 (d, J=8.2 Hz, 1H), 5.13 (brs, 1H), 4.97 (s, 1H), 4.71 (s, 1H), 3.62 (t, J=5.1 Hz, 1H), 3.04-2.90 (m, 2H), 2.24-2.10 (m, 2H), 2.09-2.01 (m, 1H), 1.99-1.92 (m, 1H), 1.83-1.78 (m, 1H), 1.67-1.61 (m, 2H), 1.50-1.46 (m, 1H); ¹³C NMR: δ 148.8, 148.4, 144.3, 135.2, 133.0, 130.8, 127.6, 126.9, 117.3, 116.4, 112.2, 111.9, 110.8, 65.4, 52.3, 40.3, 36.6, 32.5, 29.7, 29.0, 21.6; m/z: Calcd for $C_{22}H_{22}BrN_3O_2S$ [M+H]⁺ 472.0689. Found 472.0696; IR: 3364, 2923, 2864, 2844, 1653, 1474, 1332, 1275, 1260, 1161, 1054, 1016, 750, 634 cm⁻¹. N-(4-{[2-(6-bromo-4-methylidene-2,3,4,4a,9,9a-hexahydro-1H-carbazol-4a-yl)ethyl]sulfamoyl}phenyl)acetamide (12m): TLC (hexanes:ethyl acetate, 1:3 v/v): $R_f$=0.30; colorless oil, 74%; ¹H NMR: δ 7.76 (d, J=8.8 Hz, 2H), 7.67 (d, J=8.8 Hz, 2H), 7.13 (dd, J=8.2, 2.0 Hz, 1H), 6.99 (d, J=2.0 Hz, 1H), 6.52 (d, J=8.2 Hz, 1H), 4.92 (d, J=1.4 Hz, 1H), 4.82 (t, J=6.3 Hz, 1H), 4.65 (s, 1H), 3.62 (t, J=4.8 Hz, 1H), 2.94 (q, J=7.2 Hz, 2H), 2.23 (s, 3H), 2.17-2.14 (m, 2H), 2.05-2.00 (m, 1H), 1.97-1.91 (m, 1H), 1.80-1.75 (m, 1H), 1.69-1.64 (m, 2H), 1.50 (dt, J=11.7, 6.0 Hz, 1H); ¹³C NMR: δ 169.0, 148.4, 142.1, 135.9, 132.2, 130.8, 130.1, 128.3, 127.9, 127.2, 119.6, 112.3, 112.1, 65.1, 52.4, 39.9, 35.9, 32.3, 24.8, 21.5; m/z: Calcd for $C_{23}H_{26}BrKN_3O_3S$ [M+K]⁺ 542.0510. Found 542.0515; IR: 3318, 3056, 2925, 2854, 1678, 1592, 1533, 1488, 1401, 1371, 1321, 1264, 1155, 094, 1005, 824, 725 cm⁻¹. N-[2-(6-bromo-4-methylidene-2,3,4,4a,9,9a-hexahydro-1H-carbazol-4a-yl)ethyl]-2-nitrobenzene-1-sulfonamide (12n): TLC (hexanes:ethyl acetate, 1:1 v/v): $R_f$=0.50; colorless oil, 87%; ¹H NMR: δ 8.16-8.03 (m, 1H), 7.87 (dd, J=6.9, 2.4 Hz, 1H), 7.82-7.67 (m, 2H), 7.14 (dd, J=8.3, 2.0 Hz, 1H), 7.02 (d, J=2.1 Hz, 1H), 6.55 (d, J=8.3 Hz, 1H), 5.82 (t, J=6.1 Hz, 1H), 4.96 (s, 1H), 4.71 (s, 1H), 3.68 (t, J=5.0 Hz, 1H), 3.21-2.99 (m, 3H), 2.26-2.15 (m, 2H), 2.15-2.08 (m, 1H), 2.06-2.00 (m, 1H), 1.87-1.80 (m, 1H), 1.74-1.62 (m, 2H), 1.55-1.46 (m, 1H); ¹³C NMR: δ 148.9, 148.6, 135.4, 133.7, 133.5, 132.8, 131.0, 130.7, 126.9, 125.4, 112.1, 111.8, 110.6, 65.4, 52.4, 46.0, 40.7, 36.4, 32.5, 28.7, 21.7; m/z: Calcd for $C_{21}H_{21}BrN_3O_4S$ [M+K]⁺ 530.0146. Found 530.0151; IR: 3367, 3091, 2932, 2857, 2360, 1735, 1600, 1540, 1475, 1422, 1362, 1342, 1261, 1166, 812, 738 cm⁻¹. 2-Amino-N-[2-(6-bromo-4-methylidene-2,3,4,4a,9,9a-hexahydro-1H-carbazol-4a-yl)ethyl]benzene-1-sulfonamide (12o): TLC (hexanes:ethyl acetate, 1:1 v/v): $R_f$=0.30; colorless oil, 79%; ¹H NMR: δ 7.70 (d, J=7.9 Hz, 1H), 7.35 (t, J=7.7 Hz, 1H), 7.19-7.12 (m, 1H), 7.01 (s, 1H), 6.84 (t, J=7.6 Hz, 1H), 6.79 (d, J=8.2 Hz, 1H), 6.52 (d, J=8.3 Hz, 1H), 4.97 (d, J=6.8 Hz, 1H), 4.89 (s, 1H), 4.58 (s, 1H), 3.60 (s, 1H), 2.98-2.88 (m, 2H), 2.13 (q, J=4.7 Hz, 2H), 1.98 (ddd, J=15.2, 9.2, 6.2 Hz, 1H), 1.89 (ddd, J=14.5, 9.0, 5.9 Hz, 1H), 1.77-1.73 (m, 1H), 1.69-1.62 (m, 2H), 1.52-1.47 (m, 1H); ¹³C NMR: δ 148.7, 147.4, 138.0, 136.0, 135.8, 134.3, 133.1, 130.6, 129.5, 126.7, 121.7, 117.5, 112.0, 111.7, 110.5, 65.2, 52.2, 40.2, 35.4, 32.2, 28.4, 21.6; m/z: Calcd for $C_{21}H_{24}BrN_3O_2S$ [M+H]⁺ 462.0845. Found 462.0835; IR: 3370, 2924, 2853, 1712, 1599, 1481, 1454, 1318, 1260, 901, 809, 754 cm⁻¹. N-[2-(6-bromo-4-methylidene-2,3,4,4a,9,9a-hexahydro-1H-carbazol-4a-yl)ethyl]pyridine-2-sulfonamide (12p): TLC (chloroform:methanol, 10:1 v/v): $R_f$=0.50; colorless oil, 77%; ¹H NMR: δ 8.82-8.65 (m, 1H), 8.01 (d, J=7.9 Hz, 1H), 7.94 (td, J=7.7, 1.7 Hz, 1H), 7.52 (ddd, J=7.5, 4.7, 1.3 Hz, 1H), 7.13 (dd, J=8.3, 2.0 Hz, 1H), 7.01 (d, J=2.0 Hz, 1H), 6.54 (d, J=8.2 Hz, 1H), 5.32 (t, J=6.1 Hz, 1H), 4.92 (s, 1H), 4.64 (s, 1H), 3.68 (t, J=4.7 Hz, 1H), 3.07 (dtd, J=8.7, 6.2, 2.1 Hz, 2H), 2.1-2.15 (m, 2H), 2.11-2.04 (m, 1H), 2.02-1.96 (m, 1H), 1.88-1.76 (m, 1H), 1.70-1.65 (m, 2H), 1.56-1.49 (m, 1H); ¹³C NMR: δ 157.4, 150.1, 148.9, 148.8, 138.1, 135.7, 130.6, 127.0, 126.7, 122.3, 112.1, 111.8, 110.6, 110.5, 65.3, 52.3, 40.7, 36.0, 32.4, 28.4, 21.8; m/z: Calcd for $C_{20}H_{22}BrN_3O_2S$ [M+H]⁺ 448.0689. Found 448.0695; IR: 3363, 2926, 2854, 1720, 1637, 1578, 1474, 1426, 1331, 1174, 902, 811 cm⁻¹. 2,2,2-trichloroethyl N-[2-(6-bromo-4-methylidene-2,3,4,4a,9,9a-hexahydro-1H-carbazol-4a-yl)ethyl]carbamate (12p): TLC (hexanes:ethyl acetate, 3:1 v/v): $R_f$=0.40; colorless oil, 75%; ¹H NMR: δ 7.18 (d, J=7.1 Hz, 2H), 6.60 (d, J=8.1 Hz, 1H), 5.12 (d, J=5.8 Hz, 1H), 4.98 (s, 1H), 4.75 (s, 1H), 4.72 (s, 2H), 3.75 (d, J=4.9 Hz, 1H), 3.36 (ddt, J=13.8, 10.0, 6.0 Hz, 1H), 3.24 (ddt, J=13.7, 11.2, 5.7 Hz, 1H), 2.25-2.14 (m, 2H), 2.13-2.06 (m, 1H), 2.01 (ddd, J=14.5, 10.0, 5.6 Hz, 1H), 1.86 (td, J=11.7, 11.2, 6.9 Hz, 1H), 1.69 (ddt, J=12.0, 8.8, 4.2 Hz, 2H), 1.55 (dq, J=13.1, 6.7, 6.1 Hz, 1H). 2-(6-Bromo-8-fluoro-4-methylidene-2,3,4,4a,9,9a-hexahydro-1H-carbazol-4a-yl)ethan-1-amine (11b): TLC (choloroform:methanol, 10:1 v/v): $R_f$=0.10; colorless oil, 81%; ¹H NMR: δ 7.01 (d, J=9.0 Hz, 2H), 4.88 (s, 1H), 4.58 (s, 1H), 3.76 (t, J=4.1 Hz, 1H), 2.81 (dt, J=11.5, 5.6 Hz, 1H), 2.68 (td, J=12.0, 11.3, 5.2 Hz, 1H), 2.20 (dt, J=8.9, 4.8 Hz, 2H), 2.01 (ddd, J=13.9, 10.9, 5.4 Hz, 1H), 1.94-1.88 (m, 1H), 1.85-1.69 (m, 3H), 1.62-1.58 (m, 1H); ¹³C NMR: δ 150.7, 149.2, 147.5, 139.7, 139.6, 136.5, 136.3, 123.3, 123.2, 117.7, 117.4, 111.8, 109.1, 109.0, 66.2, 53.1, 53.1, 39.1, 38.8, 32.2, 27.5, 21.9; m/z: Calcd for $C_{15}H_{18}BrFN_2$ [M+H]⁺ 325.0710. Found 325.0714; IR: 3369, 2931, 2857, 1636, 1591, 1471, 1315, 848 cm⁻¹. Benzyl N-[2-(6-bromo-8-fluoro-4-methylidene-2,3,4,4a,9,9a-hexahydro-1H-carbazol-4a-yl)ethyl]carbamate (10b): TLC (hexanes:ethyl acetate, 3:1 v/v): $R_f$=0.40; colorless oil, 92%; ¹H NMR: δ 7.43-7.31 (m, 5H), 7.06-6.97 (m, 2H), 5.10 (s, 2H), 4.96 (s, 1H), 4.84 (t, J=5.8 Hz, 1H), 4.70 (s, 1H), 3.79 (dd, J=8.9, 4.9 Hz, 2H), 3.36-3.29 (m, 1H), 3.21-3.14 (m, 1H), 2.21 (t, J=5.8 Hz, 2H), 2.11-2.05 (m, 1H), 2.01-1.97 (m, 1H), 1.8-1.83 (m, 1H), 1.78-1.69 (m, 2H), 1.60-1.54 (m, 1H); ¹³C NMR: δ 156.3, 150.7, 148.5, 147.5, 139.0, 139.0, 136.5, 136.5, 136.3, 128.5, 128.1, 128.1, 123.1, 123.0, 118.0, 117.7, 112.3, 109.3, 109.2, 77.5, 77.1, 76.7, 66.7, 65.9, 52.8, 52.8, 38.0, 35.4, 32.3, 28.0, 21.8; m/z: Calcd for $C_{23}H_{25}BrFN_2O_2$ [M+H]⁺ 459.1078. Found 459.1090; IR: 3416, 3298, 2923, 2851, 1701, 1577, 1523, 1477, 1454, 1371, 1308, 1255, 1217, 1131, 882, 826 cm⁻¹. N-[2-(6-bromo-4-methylidene-2,3,4,4a,9,9a-hexahydro-1H-carbazol-4a-yl)ethyl]-4-methoxybenzene-1-sulfonamide (13a): TLC (hexanes:ethyl acetate, 2:1 v/v): $R_f$=0.20; colorless oil, 91%; ¹H NMR: δ 7.77 (d, J=8.9 Hz, 2H), 7.10-6.93 (m, 3H), 6.84 (d, J=1.8 Hz, 1H), 4.93 (d, J=1.5 Hz, 1H), 4.65 (t, J=6.3 Hz, 1H), 4.62 (s, 1H), 3.89 (s, 3H), 3.75 (brs, 1H), 3.70 (t, J=4.6 Hz, 1H), 3.00-2.89 (m, 2H), 2.16 (t, J=6.2 Hz, 2H), 2.09-2.01 (m, 1H), 1.99-1.93 (m, 1H), 1.85-1.78 (m, 1H), 1.71-1.64 (m, 2H), 1.56-1.51 (m, 1H).; $^{13}$C NMR: δ 162.9, 150.7, 148.2, 147.5, 138.4, 138.3, 136.4, 136.2, 131.2, 129.2, 122.9, 122.8, 118.1, 117.8, 114.3, 112.38, 109.5, 109.4, 65.9, 55.6, 52.9, 52.9, 40.1, 35.7, 32.3, 28.3, 21.7; m/z: Calcd for $C_{22}H_{24}BrFN_2O_3S$ [M+H]$^+$ 495.0748. Found 495.0759; IR: 3054, 2986, 2924, 2850, 1597, 1421, 1265, 1157, 1094, 896, 835, 740 cm$^{-1}$. N-[2-(6-bromo-8-fluoro-4-methylidene-2,3,4,4a,9,9a-hexahydro-1H-carbazol-4a-yl)ethyl]-4-methylbenzene-1-sulfonamide (13b): TLC (hexanes:ethyl acetate, 3:1 v/v): $R_f$=0.50; colorless oil, 83%; $^1$H NMR: δ 7.72 (d, J=8.3 Hz, 2H), 7.33 (d, J=8.0 Hz, 2H), 7.01 (dd, J=9.6, 1.7 Hz, 1H), 6.84 (d, J=1.7 Hz, 1H), 4.93 (d, J=1.5 Hz, 1H), 4.63 (d, J=7.6 Hz, 1H), 3.73 (brs, 1H), 3.70 (t, J=4.7 Hz, 1H), 3.02-2.90 (m, 2H), 2.45 (s, 3H), 2.16 (dd, J=7.6, 4.7 Hz, 2H), 2.05 (dt, J=14.0, 7.9 Hz, 1H), 1.96 (dt, J=14.5, 7.4 Hz, 1H), 1.81 (td, J=10.9, 5.4 Hz, 1H), 1.75-1.65 (m, 1H), 1.52 (tt, J=10.3, 4.8 Hz, 1H); $^{13}$C NMR: δ 148.2, 143.6, 138.4, 136.7, 129.8, 129.0, 127.1, 122.9, 122.8, 118.1, 117.9, 112.4, 65.9, 52.9, 40.1, 35.8, 32.3, 28.3, 21.7, 21.6; m/z: Calcd for $C_{22}H_{24}BrFN_2O_2S$ [M+H]$^+$ 479.0799. Found 479.0793; IR: 3054, 2925, 2850, 1422, 1265, 971, 896, 741 cm$^{-1}$. N-[2-(6-bromo-8-fluoro-4-methylidene-2,3,4,4a,9,9a-hexahydro-1H-carbazol-4a-yl)ethyl]-4-fluorobenzene-1-sulfonamide (13c): TLC (hexanes:ethyl acetate, 3:1 v/v): $R_f$=0.20; colorless oil, 72%; $^1$H NMR: δ 7.95-7.80 (m, 2H), 7.21 (dd, J=9.5, 7.6 Hz, 2H), 7.02 (dd, J=9.6, 1.7 Hz, 1H), 6.84 (d, J=1.8 Hz, 1H), 4.95 (s, 1H), 4.81 (t, J=6.3 Hz, 1H), 4.66 (s, 1H), 3.76 (brs, 1H), 3.70 (t, J=4.8 Hz, 1H), 3.00-2.90 (m, 1H), 2.21-2.12 (m, 1H), 2.11-2.02 (m, 1H), 2.00-1.94 (m, 1H), 1.89-1.78 (m, 1H), 1.71-1.64 (m, 2H), 1.57-1.47 (m, 1H). $^{13}$C NMR (101 MHz, cdcl$_3$) δ 150.7, 148.1, 147.5, 138.2, 138.2, 136.3, 136.2, 135.8, 135.8, 129.8, 129.7, 122.8, 122.8, 118.2, 117.9, 116.6, 116.3, 112.4, 109.7, 109.6, 66.0, 52.9, 52.9, 40.1, 36.0, 32.4, 28.5, 21.6; m/z: Calcd for C21H22BrF2N2O2S [M+Na]$^+$ 483.0548. Found 483.0553; IR: 3054, 2986, 2925, 2849, 1593, 1495, 1469, 1265, 896, 840 cm$^{-1}$. 4-Bromo-N-[2-(6-bromo-8-fluoro-4-methylidene-2,3,4,4a,9,9a-hexahydro-1H-carbazol-4a-yl)ethyl]benzene-1-sulfonamide (13d): TLC (hexanes:ethyl acetate, 3:1 v/v): $R_f$=0.40; colorless oil, 81%; $^1$H NMR: δ 7.75-7.60 (m, 4H), 6.99 (d, J=9.5 Hz, 1H), 6.82 (s, 1H), 4.93 (s, 1H), 4.82 (t, J=6.3 Hz, 1H), 4.64 (s, 1H), 3.73 (br.s, 1H), 3.66 (t, J=4.9 Hz, 1H), 2.91 (ddd, J=10.0, 8.1, 5.1 Hz, 2H), 2.13 (q, J=5.2 Hz, 2H), 2.02 (q, J=7.9, 7.4 Hz, 1H), 1.94 (ddd, J=14.4, 8.3, 6.2 Hz, 1H), 1.79 (td, J=12.4, 11.3, 5.8 Hz, 1H), 1.64 (p, J=6.4, 5.8 Hz, 2H), 1.49 (dq, J=12.7, 6.3 Hz, 1H); $^{13}$C NMR: δ 150.8, 148.0, 147.5, 138.8, 138.2, 138.1, 136.3, 136.1, 132.5, 128.6, 127.7, 122.8, 122.8, 118.2, 118.0, 112.5, 109.7, 109.6, 66.0, 52.9, 52.9, 40.1, 36.0, 32.4, 28.5, 21.6; m/z: Calcd for $C_{21}H_{21}Br_2N_2O_2S$ [M+H]$^+$ 542.9747. Found 542.9761; IR: 3773, 2929, 2859, 1620, 1528, 1327, 1260, 1222, 1161, 1068, 1010, 902, 822, 764 cm$^{-1}$. N-[2-(6-bromo-8-fluoro-4-methylidene-2,3,4,4a,9,9a-hexahydro-1H-carbazol-4a-yl)ethyl]-4-iodobenzene-1-sulfonamide (13e): TLC (hexanes:ethyl acetate, 3:1 v/v): $R_f$=0.50; colorless oil, 81%; $^1$H NMR: δ 7.89 (d, J=8.5 Hz, 2H), 7.54 (d, J=8.5 Hz, 2H), 7.03 (dd, J=9.5, 1.7 Hz, 1H), 6.85 (d, J=1.7 Hz, 1H), 4.96 (d, J=1.5 Hz, 1H), 4.82 (t, J=6.4 Hz, 1H), 4.67 (s, 1H), 3.75 (brs, 1H), 3.69 (td, J=4.9 Hz, 1H), 3.00-2.88 (m, 2H), 2.23-2.12 (m, 2H), 2.09-2.03 (m, 1H), 2.00-1.95 (m, 2H), 1.87-1.78 (m, 1H), 1.72-1.63 (m, 2H), 1.57-1.47 (m, 1H).; $^{13}$C NMR (101 MHz, cdcl$_3$) δ 150.3, 148.0, 147.9, 139.4, 138.4, 138.2, 138.1, 136.2, 136.1, 128.4, 122.8, 122.8, 118.2, 118.0, 112.5, 109.7, 109.6, 100.1, 65.9, 52.9, 52.8, 40.1, 36.0, 32.3, 28.5, 21.6; m/z: Calcd for C21H21BrFIN2NaO2S [M+H]$^+$ 590.9609. Found 590.9626; IR: 3054, 2986, 2918, 2849, 1624, 1571, 1471, 1336, 1265, 1163, 1125, 896, 819, 740 cm$^{-1}$. N-[2-(6-bromo-8-fluoro-4-methylidene-2,3,4,4a,9,9a-hexahydro-1H-carbazol-4a-yl)ethyl]-3,4-dichlorobenzene-1-sulfonamide (13f): TLC (hexanes:ethyl acetate, 3:1 v/v): $R_f$=0.75; colorless oil, 80%; $^1$H NMR: δ 7.92 (d, J=2.1 Hz, 1H), 7.65 (dd, J=8.4, 2.1 Hz, 1H), 7.61 (d, J=8.4 Hz, 1H), 7.03 (dd, J=9.5, 1.7 Hz, 1H), 6.86 (d, J=1.8 Hz, 1H), 4.98 (d, J=1.5 Hz, 1H), 4.94 (t, J=6.3 Hz, 1H), 4.70 (s, 1H), 3.04-2.89 (m, 2H), 2.22-2.15 (m, 2H), 2.13-2.05 (m, 1H), 2.02-1.95 (m, 1H), 1.86-1.81 (m, 1H), 1.72-1.62 (m, 3H), 1.55-1.49 (m, 1H). $^{13}$C NMR: δ 150.8, 147.9, 147.5, 139.7, 138.1, 138.0, 137.6, 136.3, 133.8, 131.2, 129.0, 126.0, 122.8, 122.7, 118.3, 118.0, 112.53, 109.8, 109.7, 66.0, 52.9, 52.9, 40.2, 36.2, 32.4, 28.7, 21.6; m/z: Calcd for $C_{21}H_{20}BrCl_2FN_2O_2S$ [M+H]$^+$ 532.9863. Found 532.9869; IR: 3365, 3085, 2925, 2855, 1624, 1560, 1456, 1333, 1203, 1164, 1059, 903, 820, 613 cm$^{-1}$. N-(4-{[2-(6-bromo-8-fluoro-4-methylidene-2,3,4,4a,9,9a-hexahydro-1H-carbazol-4a-yl)ethyl]sulfamoyl}phenyl)acetamide (13g): TLC (hexanes:ethyl acetate, 1:3 v/v): $R_f$=0.50; colorless oil, 62%; $^1$H NMR: δ 7.78 (d, J=8.8 Hz, 2H), 7.67 (d, J=8.6 Hz, 2H), 7.43 (brs, 1H), 7.01 (dd, J=9.6, 1.7 Hz, 1H), 6.85 (d, J=1.8 Hz, 1H), 4.94 (s, 1H), 4.70 (t, J=6.3 Hz, 1H), 4.63 (s, 1H), 3.75 (brs, 1H), 3.68 (t, J=4.7 Hz, 1H), 2.98-2.90 (m, 2H), 2.24 (s, 4H), 2.18-2.15 (m, 2H), 2.08-2.02 (m, 1H), 1.99-1.93 (m, 1H), 1.85-1.78 (m, 1H), 1.72-1.63 (m, 2H), 1.55-1.49 (m, 1H); $^{13}$C NMR: δ 168.6, 150.8, 148.1, 141.8, 138.3, 136.4, 136.2, 134.5, 128.4, 128.3, 122.8, 122.8, 119.4, 118.2, 117.9, 112.4, 65.9, 52.9, 40.1, 35.8, 32.3, 28.3, 24.8, 21.6; m/z: Calcd for $C_{23}H_{26}BrN_3O_3S$ [M+H]$^+$ 504.0951. Found 542.0502; IR: 3243, 3092, 2980, 2944, 1695, 1591, 1473, 1399, 1371, 1317, 1261, 1158, 1035, 848, 763 cm$^{-1}$. N-[2-(6-bromo-8-fluoro-4-methylidene-2,3,4,4a,9,9a-hexahydro-1H-carbazol-4a-yl)ethyl]-4-cyanobenzene-1-sulfonamide (13h): TLC (hexanes:ethyl acetate, 3:1 v/v): $R_f$=0.20; colorless oil, 75%; $^1$H NMR: δ 7.94 (d, J=8.4 Hz, 2H), 7.83 (d, J=8.4 Hz, 2H), 7.03 (dd, J=9.5, 1.7 Hz, 1H), 6.84 (d, J=1.8 Hz, 1H), 5.06 (brs, 1H), 4.98 (s, 1H), 4.70 (s, 1H), 3.77 (brs, 1H), 3.69 (t, J=5.1 Hz, 1H), 3.03-2.89 (m, 2H), 2.27-2.11 (m, 2H), 2.10-2.04 (m, 1H), 2.02-1.96 (m, 1H), 1.86-1.81 (m, 1H), 1.74-1.63 (m, 2H), 1.54-1.47 (m, 1H); $^{13}$C NMR: δ 150.3, 147.9, 147.8, 144.1, 138.0, 137.9, 136.2, 136.1, 133.0, 127.6, 122.7, 122.7, 118.3, 118.1, 117.3, 116.4, 112.5, 109.8, 109.8, 66.0, 52.8, 52.8, 40.2, 36.3, 32.4, 28.8, 21.5; m/z: Calcd for $C_{22}H_{21}BrFN_3O_2S$ [M+H]$^+$ 490.0595. Found 490.0600; IR: 3054, 2924, 2849, 1570, 1462, 1421, 1265, 1019, 971, 896, 740 cm$^{-1}$. N-[2-(6-bromo-8-fluoro-4-methylidene-2,3,4,4a,9,9a-hexahydro-1H-carbazol-4a-yl)ethyl]-4-(trifluoromethyl)benzene-1-sulfonamide (13i): TLC (hexanes:ethyl acetate, 3:1 v/v): $R_f$=0.40; colorless oil, 71%; $^1$H NMR: δ 7.93 (d, J=8.1 Hz, 2H), 7.77 (d, J=8.2 Hz, 2H), 6.99 (dd, J=9.4, 1.7 Hz, 1H), 6.82 (d, J=1.7 Hz, 1H), 4.94 (s, 2H), 4.66 (s, 1H), 3.73 (s, 1H), 3.66 (t, J=5.1 Hz, 1H), 3.06-2.81 (m, 2H), 2.13 (dt, J=12.4, 5.8 Hz, 2H), 2.09-1.90 (m, 2H), 1.86-1.73 (m, 1H), 1.68-1.61 (m, 2H), 1.47 (dd, J=11.0, 5.8 Hz, 1H); $^{13}$C NMR: δ 150.8, 147.9, 147.5, 143.4, 138.1, 138.0, 136.3, 136.1, 134.7, 134.2, 127.5, 126.4, 126.4, 126.3, 126.3, 125.0, 122.8, 122.7, 121.4, 118.3, 118.0, 112.5, 109.8, 109.7, 66.0, 52.9, 52.9, 40.2, 36.3, 28.7, 21.6; m/z: Calcd for $C_{22}H_{21}BrF4N_2O_2S$ [M+H]$^+$ 533.0516. Found 533.0520; IR: 3054, 2987, 2926, 2853, 1559, 1507, 1421, 1323, 1265, 1063, 896, 740 cm$^{-1}$. 3,4-

Dibromo-N-[2-(6-bromo-8-fluoro-4-methylidene-2,3,4,4a, 9,9a-hexahydro-1H-carbazol-4a-yl)ethyl]benzene-1-sulfonamide (13j): TLC (hexanes:ethyl acetate, 3:1 v/v): $R_f$=0.50; colorless oil, 77%; $^1$H NMR: δ 8.07 (d, J=2.2 Hz, 1H), 7.78 (d, J=8.3 Hz, 1H), 7.60 (dd, J=8.4, 2.2 Hz, 1H), 7.04 (dd, J=9.5, 1.7 Hz, 1H), 6.87 (s, 1H), 4.99 (s, 1H), 4.91 (t, J=6.2 Hz, 1H), 4.71 (s, 1H), 3.81-3.75 (m, 1H), 3.70 (t, J=5.0 Hz, 1H), 3.09-2.88 (m, 2H), 2.27-2.13 (m, 2H), 2.11-2.05 (m, 1H), 2.02-1.97 (m, 1H), 1.87-1.81 (m, 1H), 1.73-1.62 (m, 2H), 1.56-1.48 (m, 1H).; $^{13}$C NMR: δ 150.8, 147.9, 140.4, 138.1, 138.0, 136.3, 136.1, 134.4, 131.9, 130.2, 128.2, 126.6, 125.9, 122.8, 122.7, 118.3, 118.0, 112.5, 109.8, 109.7, 66.0, 52.9, 52.9, 40.2, 36.2, 32.4, 28.7, 21.6; m/z: Calcd for $C_{21}H_{20}Br3FN_2O_2SNa$ [M+Na]$^+$ 642.8672. Found 642.8661; IR: 3356, 2925, 2850, 1662, 1469, 1333, 1275, 1261, 1161, 1107, 1014, 849, 750 cm$^{-1}$. 4-Bromo-N-[2-(6-bromo-8-fluoro-4-methylidene-2,3,4,4a,9,9a-hexahydro-1H-carbazol-4a-yl)ethyl]-3-fluorobenzene-1-sulfonamide (13k): TLC (hexanes:ethyl acetate, 3:1 v/v): $R_f$=0.40; colorless oil, 71%; $^1$H NMR: δ 7.73 (dd, J=8.3, 6.4 Hz, 1H), 7.59 (dd, J=7.7, 2.0 Hz, 1H), 7.54-7.47 (m, 1H), 7.03 (dd, J=9.5, 1.7 Hz, 1H), 6.86 (d, J=1.7 Hz, 1H), 5.21-5.11 (m, 1H), 4.97 (s, 1H), 4.70 (s, 1H), 3.77 (s, 1H), 3.70 (t, J=5.0 Hz, 1H), 3.02-2.89 (m, 2H), 2.25-2.12 (m, 2H), 2.11-2.06 (m, 1H), 2.03-1.97 (m, 1H), 1.89-1.80 (m, 1H), 1.72-1.65 (m, 2H), 1.55-1.47 (m, 1H) $^{13}$C NMR: δ 160.6, 157.3, 150.8, 148.0, 147.5, 141.1, 141.0, 138.1, 138.1, 136.3, 136.1, 134.5, 132.2, 128.4, 123.7, 123.6, 122.8, 122.8, 118.3, 118.0, 115.5, 115.1, 114.8, 114.5, 112.5, 109.8, 109.7, 66.0, 52.9, 52.9, 40.2, 36.1, 32.4, 28.7, 21.6; m/z: Calcd for C21H21Br2F2N2O2S [M+H]$^+$ 560.9653. Found 560.9659; IR: 3082, 2927, 2854, 1718, 1623, 1590, 1471, 1399, 1333, 1233, 1190, 1038, 848, 820, 738 cm$^{-1}$. 4-Bromo-N-[2-(6-bromo-8-fluoro-4-methylidene-2,3,4,4a,9,9a-hexahydro-1H-carbazol-4a-yl)ethyl]-2-(trifluoromethyl)benzene-1-sulfonamide (13l): TLC (hexanes:ethyl acetate, 3:1 v/v): $R_f$=0.40; colorless oil, 72%; $^1$H NMR: δ 8.05 (d, J=8.5 Hz, 1H), 8.01 (d, J=2.0 Hz, 1H), 7.86 (dd, J=8.5, 2.0 Hz, 1H), 7.03 (dd, J=9.6, 1.7 Hz, 1H), 6.86 (d, J=1.7 Hz, 1H), 5.17-5.10 (m, 1H), 4.97 (d, J=1.4 Hz, 1H), 4.69 (s, 1H), 3.76 (brs, 1H), 3.70 (t, J=4.9 Hz, 1H), 3.06-2.84 (m, 2H), 2.26-2.12 (m, 2H), 2.10-2.06 (m, 1H), 2.03-1.97 (m, 1H), 1.89-1.79 (m, 1H), 1.72-1.63 (m, 2H), 1.55-1.48 (m, 1H); $^{13}$C NMR (101 MHz, cdcl$_3$) δ 150.3, 148.0, 138.0, 138.0, 137.5, 136.3, 136.1, 135.4, 133.1, 131.8, 131.7, 129.0, 128.6, 127.5, 122.7, 122.7, 118.2, 118.0, 112.4, 109.7, 109.6, 65.9, 52.8, 52.8, 40.2, 36.2, 32.4, 31.0, 28.6, 21.6; m/z: Calcd for $C_{22}H_{20}Br2F4N_2O_2S$ [M+H]$^+$ 610.9621. Found 610.9628; IR: 3378, 3054, 2917, 2849, 1582, 1469, 1348, 1298, 1265, 1170, 1122,816, 740 cm$^{-1}$. 4-Bromo-N-[2-(6-bromo-8-fluoro-4-methylidene-2,3,4,4a,9,9a-hexahydro-1H-carbazol-4a-yl)ethyl]-3-(trifluoromethyl)benzene-1-sulfonamide (13m): TLC (hexanes:ethyl acetate, 3:1 v/v): $R_f$=0.40; colorless oil, 75%; $^1$H NMR: δ 8.22-8.11 (m, 1H), 7.90 (d, J=8.3 Hz, 1H), 7.82 (dd, J=8.3, 2.2 Hz, 1H), 7.03 (dd, J=9.6, 1.7 Hz, 1H), 6.86 (d, J=1.8 Hz, 1H), 5.10 (brs, 1H), 4.99 (s, 1H), 4.72 (s, 1H), 3.77 (s, 1H), 3.70 (t, J=5.1 Hz, 1H), 3.04-2.90 (m, 2H), 2.23-2.14 (m, 2H), 2.07 (dd, J=8.5, 6.6 Hz, 1H), 2.03-1.97 (m, 1H), 1.87-1.81 (m, 1H), 1.72-1.60 (m, 2H), 1.55-1.49 (m, 1H); $^{13}$C NMR: δ 150.8, 147.8, 147.5, 139.8, 138.0, 138.0, 136.2, 136.1, 136.0, 131.0, 126.5, 126.4, 126.4, 126.3, 125.3, 125.3, 123.9, 122.8, 122.7, 120.3, 118.3, 118.0, 112.5, 109.9, 109.8, 66.0, 52.9, 52.9, 40.2, 36.4, 32.4, 28.9, 21.5; m/z: Calcd for $C_{22}H_{20}Br2F4N_2O_2S$ [M+H]$^+$ 610.9621. Found 610.9626; IR: 3361, 3294, 2917, 2849, 1675, 1624, 1593, 1468, 1308, 1260, 1160, 1096, 1024, 850, 830 cm$^{-1}$. 3-bromo-N-[2-(6-bromo-8-fluoro-4-methylidene-2,3,4,4a,9,9a-hexahydro-1H-carbazol-4a-yl)ethyl]-4-(difluoromethoxy)benzene-1-sulfonamide (13u): TLC (hexanes:ethyl acetate, 3:1 v/v): $R_f$=0.40; colorless oil, 75%; $^1$H NMR: δ 7.94 (d, J=2.3 Hz, 1H), 7.74 (dd, J=8.5, 2.3 Hz, 1H), 7.38 (d, J=8.5 Hz, 1H), 7.06 (d, J=9.0 Hz, 1H), 6.89 (s, 1H), 5.02 (s, 1H), 4.74 (s, 1H), 3.80 (brs, 1H), 3.06-2.93 (m, 2H), 2.27-2.19 (m, 1H), 2.10 (ddd, J=24.3, 10.6, 4.3 Hz, 2H), 2.04-1.96 (m, 1H), 1.91 (s, 1H), 1.70 (dt, J=8.1, 4.4 Hz, 2H), 1.55 (s, 1H). N-[2-(6-bromo-8-fluoro-4-methylidene-2,3,4,4a,9,9a-hexahydro-1H-carbazol-4a-yl)ethyl]-1-benzofuran-2-sulfonamide (13t): TLC (hexanes:ethyl acetate, 3:1 v/v): $R_f$=0.40; colorless oil, 75%; $^1$H NMR (500 MHz, Chloroform-d δ 7.71 (d, J=7.9 Hz, 1H), 7.57 (d, J=8.4 Hz, 1H), 7.52-7.45 (m, 1H), 7.43-7.32 (m, 2H), 7.00 (dd, J=9.5, 1.8 Hz, 1H), 6.89 (d, J=1.8 Hz, 1H), 5.23-5.10 (m, 1H), 4.96 (s, 1H), 4.68 (s, 1H), 3.73 (s, 1H), 3.13 (dtd, J=9.3, 6.5, 3.0 Hz, 2H), 2.23-1.96 (m, 4H), 1.82 (dq, J=13.3, 6.3, 5.9 Hz, 1H), 1.71-1.62 (m, 2H), 1.54-1.44 (m, 1H); $^{13}$C NMR (100 MHz, CDCl$_3$) δ 155.7, 149.7, 147.7, 127.7, 125.90, 124.3, 122.9, 122.8, 122.8, 118.3, 118.1, 112.6, 112.5, 112.2, 65.9, 52.9, 40.3, 36.1, 32.3, 29.7, 28.4, 21.6. N-[2-(6-bromo-8-fluoro-4-methylidene-2,3,4,4a,9,9a-hexahydro-1H-carbazol-4a-yl)ethyl]-1-methyl-1H-imidazole-4-sulfonamide (13s): TLC (hexanes: ethyl acetate, 3:1 v/v): $R_f$=0.40; colorless oil, 75%; $^1$H NMR: δ 7.22-7.13 (m, 2H), 7.02 (dd, J=9.5, 1.7 Hz, 1H), 6.92 (s, 1H), 5.55 (s, 1H), 4.91 (s, 1H), 4.60 (s, 1H), 3.84 (s, 1H), 3.78 (s, 4H), 3.07 (s, 1H), 2.95 (q, J=9.6, 9.0 Hz, 1H), 2.25-1.99 (m, 5H), 1.86 (tt, J=11.0, 4.3 Hz, 1H), 1.76-1.68 (m, H), 1.57 (q, J=4.3, 3.4 Hz, 1H); $^{13}$C NMR: δ 151.0, 148.3, 147.7, 139.4, 139.1, 139.1, 135.8, 135.7, 128.9, 128.7, 125.0, 124.2, 123.1, 123.1, 118.0, 117.7, 112.4, 109.83, 109.7, 65.8, 53.0, 53.0, 40.3, 35.1, 34.4, 34.3, 32.2, 27.6, 21.8. N-[2-(6-bromo-8-fluoro-4-methylidene-2,3,4,4a, 9,9a-hexahydro-1H-carbazol-4a-yl)ethyl]-6-chloropyridine-3-sulfonamide (13r): TLC (hexanes:ethyl acetate, 3:1 v/v): $R_f$=0.40; colorless oil, 75%; $^1$H NMR: δ 8.83 (d, J=2.5 Hz, 1H), 8.05 (dd, J=8.3, 2.5 Hz, 1H), 7.50 (d, J=8.4 Hz, 1H), 7.06 (dd, J=9.4, 1.8 Hz, 1H), 6.88 (s, 1H), 5.14 (s, 1H), 5.02 (s, 1H), 4.74 (s, 1H), 3.76 (d, J=6.3 Hz, 1H), 3.12-2.91 (m, 2H), 2.21 (td, J=8.7, 4.2 Hz, 1H), 2.17-1.97 (m, 3H), 1.94-1.79 (m, 1H), 1.66 (dddd, J=20.6, 13.7, 7.7, 3.4 Hz, 2H), 1.54-1.44 (m, 1H); $^{13}$C NMR: δ 155.5, 148.3, 137.2, 135.6, 124.8, 122.8, 122.8, 118.6, 118.3, 112.9, 66.0, 53.0, 53.0, 40.2, 36.4, 32.4, 28.6, 21.5. 5-bromo-N-[2-(6-bromo-8-fluoro-4-methylidene-2,3,4,4a,9,9a-hexahydro-1H-carbazol-4a-yl)ethyl]pyridine-3-sulfonamide (13q): TLC (hexanes:ethyl acetate, 3:1 v/v): $R_f$=0.40; colorless oil, 75%; $^1$H NMR: δ 8.91 (d, J=39.7 Hz, 2H), 8.25 (s, 1H), 7.06 (d, J=9.5 Hz, 1H), 6.89 (s, 1H), 5.19 (brs, 1H), 5.03 (s, 1H), 4.76 (s, 1H), 3.77 (d, J=7.3 Hz, 1H), 3.16-2.90 (m, 2H), 2.22 (td, J=8.8, 4.3 Hz, 1H), 2.12 (ddd, J=20.6, 10.5, 6.3 Hz, 2H), 2.06-1.96 (m, 1H), 1.89 (q, J=8.3, 6.4 Hz, 1H), 1.66 (dddd, J=23.9, 13.7, 7.4, 4.0 Hz, 2H), 1.51 (ddd, J=11.1, 7.6, 3.6 Hz, 1H); $^{13}$C NMR: δ 154.4, 147.2, 145.8, 137.0, 122.8, 122.8, 118.7, 118.4, 113.0, 66.0, 53.0, 40.2, 36.5, 32.4, 28.7, 21.6. 4-bromo-N-[2-(6-bromo-8-fluoro-4-methylidene-2,3,4,4a,9,9a-hexahydro-1H-carbazol-4a-yl)ethyl]-2-methylbenzene-1-sulfonamide (13n): TLC (hexanes:ethyl acetate, 3:1 v/v): $R_f$=0.40; colorless oil, 75%; $^1$H NMR: δ 7.81 (d, J=8.3 Hz, 1H), 7.54-7.42 (m, 2H), 7.03 (dd, J=9.6, 1.8 Hz, 1H), 6.85 (d, J=1.8 Hz, 1H), 4.95 (s, 1H), 4.65 (s, 1H), 3.75 (s, 1H), 3.68 (t, J=4.8 Hz, 1H), 2.92 (q, J=7.4 Hz, 2H), 2.60 (s, 3H), 2.16 (d, J=5.2 Hz, 2H), 2.10-2.02 (m, 1H), 1.96 (dt, J=14.3, 6.9 Hz, 1H), 1.86-1.77 (m, 1H), 1.66 (dddd, J=17.4, 9.7, 7.2, 4.0 Hz, 1H), 1.56-1.46 (m, 1H); $^{13}$C NMR: δ 150.8, 148.0, 147.5, 139.0, 138.2, 138.2, 136.8, 136.3, 136.1, 135.4, 131.0, 129.4, 127.5, 122.8, 122.8, 118.2, 118.0, 112.4, 109.7, 109.7, 65.9, 52.9, 52.9, 39.9, 36.2, 32.4, 28.5, 21.6, 20.1. 4,5-dibromo-N-[2-(6-bromo-8-fluoro-4-methylidene-2,3,4,4a,9,9a-hexahydro-1H-carbazol-4a-yl)ethyl]thiophene-2-sulfonamide (13p): TLC (hexanes:ethyl acetate, 3:1 v/v): $R_f$=0.40; colorless oil, 75%; $^1$H NMR: δ 7.37 (s, 1H), 7.05 (dd, J=9.6, 1.7 Hz, 1H), 6.90 (d, J=1.8 Hz, 1H), 5.06 (t, J=6.3 Hz, 1H), 5.01 (d, J=1.4 Hz, 1H), 4.75 (s, 1H), 3.79 (s, 1H), 3.72 (t, J=5.2 Hz, 1H), 3.12-3.04 (m, 1H), 3.00 (hept, J=6.8, 6.2 Hz, 1H), 2.27-1.97 (m, 4H), 1.86 (tt, J=9.2, 4.9 Hz, 1H), 1.68 (ddd, J=17.6, 9.1, 5.2 Hz, 2H), 1.55-1.48 (m, 1H); $^{13}$C NMR: δ 150.8, 147.9, 147.6, 141.6, 138.0, 138.0, 136.2, 136.1, 133.6, 133.3, 129.0, 128.2, 127.5, 122.8, 122.8, 118.4, 118.3, 118.1, 114.7, 112.6, 110.0, 109.9, 66.0, 52.9, 52.9, 40.5, 36.2, 32.5, 28.8, 21.6. 4-bromo-N-[2-(6-bromo-8-fluoro-4-methylidene-2,3,4,4a,9,9a-hexahydro-1H-carbazol-4a-yl)ethyl]-3-methylbenzene-1-sulfonamide (13o): TLC (hexanes:ethyl acetate, 3:1 v/v): $R_f$=0.40; colorless oil, 75%; $^1$H NMR: δ 7.80-7.64 (m, 2H), 7.49 (dd, J=8.5, 2.3 Hz, 1H), 7.02 (dd, J=9.6, 1.7 Hz, 1H), 6.86 (d, J=1.8 Hz, 1H), 4.96 (s, 1H), 4.78 (t, J=6.3 Hz, 1H), 4.67 (s, 1H), 3.75 (s, 1H), 3.70 (t, J=4.9 Hz, 1H), 2.95 (ddq, J=15.6, 8.8, 7.0 Hz, 2H), 2.48 (s, 3H), 2.17 (dt, J=10.1, 5.3 Hz, 2H), 2.07 (ddd, J=14.1, 8.9, 6.8 Hz, 1H), 1.98 (ddd, J=14.3, 8.7, 5.9 Hz, 1H), 1.87-1.78 (m, 1H), 1.67 (tp, J=14.2, 5.0 Hz, 2H), 1.55-1.49 (m, 1H); $^{13}$C NMR: δ 150.8, 148.1, 147.5, 139.6, 138.8, 138.2, 138.2, 136.3, 136.1, 133.2, 130.1, 129.0, 128.9, 128.2, 125.7, 125.3, 122.8, 122.8, 118.2, 117.9, 112.5, 109.7, 109.6, 66.0, 52.9, 52.9, 40.2, 36.0, 32.4, 28.5, 23.1, 21.6. N-[2-(6-bromo-2,4a,9,9a-tetrahydro-1H-carbazol-4a-yl)ethyl]-4-chlorobenzene-1-sulfonamide (16): TLC (hexanes:ethyl acetate, 3:1 v/v): $R_f$=0.40; colorless oil, 75%; $^1$H NMR: δ 7.73 (d, J=8.6 Hz, 2H), 7.47 (d, J=8.5 Hz, 2H), 7.11 (dd, J=8.3, 2.0 Hz, 1H), 7.00 (d, J=2.0 Hz, 1H), 6.50 (d, J=8.2 Hz, 1H), 5.86 (ddd, J=9.9, 4.8, 3.0 Hz, 1H), 5.69-5.54 (m, 2H), 3.73 (dd, J=9.0, 4.2 Hz, 1H), 3.00 (tt, J=12.4, 5.8 Hz, 1H), 2.66 (dt, J=14.1, 7.5 Hz, 1H), 2.18-2.05 (m, 1H), 1.95 (dtd, J=14.2, 5.0, 2.2 Hz, 1H), 1.91-1.76 (m, 2H), 1.71 (dq, J=12.8, 4.8 Hz, 1H), 1.59 (dtd, J=13.6, 9.0, 4.9 Hz, 1H); $^{13}$C NMR: δ 147.6, 139.0, 138.4, 136.2, 130.6, 129.9, 129.4, 128.4, 128.1, 126.3, 112.0, 111.3, 63.0, 48.0, 40.7, 39.9, 26.8, 21.1. benzyl N-(2-{2-bromo-4-fluoro-10-methylidene-5H,5aH,6H,7H,8H,9H,10H,10aH-cyclohepta[b]indol-10a-yl}ethyl)carbamate (18b): TLC (hexanes:ethyl acetate, 3:1 v/v): $R_f$=0.40; colorless oil, 75%; $^1$H NMR: δ 7.40-7.31 (m, 5H), 7.00 (dd, J=9.7, 1.8 Hz, 1H), 6.88-6.79 (m, 1H), 5.09 (s, 2H), 5.07 (s, 2H), 4.82 (s, 1H), 3.89 (dd, J=8.2, 2.4 Hz, 1H), 3.69 (s, 1H), 3.27-3.17 (m, 1H), 2.99 (ddt, J=15.3, 11.0, 5.7 Hz, 1H), 2.20 (ddd, J=12.6, 7.4, 3.6 Hz, 1H), 2.03 (dddd, J=19.0, 13.5, 9.6, 5.6 Hz, 4H), 1.82 (dq, J=16.7, 8.5 Hz, 1H), 1.69 (t, J=10.3 Hz, 1H), 1.58-1.47 (m, 4H); $^{13}$C NMR: δ 156.3, 150.8, 149.7, 146.4, 137.0, 136.8, 136.5, 128.5, 128.2, 128.1, 128.1, 124.0, 123.9, 117.8, 117.6, 114.1, 108.1, 108.0, 68.5, 66.6, 57.38, 57.4, 40.5, 37.5, 34.5, 33.4, 31.4, 24.2. N-(2-{2-bromo-10-methylidene-5H,5aH,6H,7H,8H,9H,10H,10aH-cyclohepta[b]indol-10a-yl}ethyl)-4-chlorobenzene-1-sulfonamide (20): TLC (hexanes:ethyl acetate, 3:1 v/v): $R_f$=0.40; colorless oil, 75%; $^1$H NMR: δ 7.69 (d, J=8.6 Hz, 2H), 7.47 (d, J=8.6 Hz, 2H), 7.12 (dd, J=8.3, 2.0 Hz, 1H), 6.90 (d, J=2.0 Hz, 1H), 6.44 (d, J=8.3 Hz, 1H), 5.12 (dd, J=7.4, 5.2 Hz, 1H), 5.06 (s, 1H), 5.03 (s, 1H), 3.66 (dd, J=8.3, 2.3 Hz, 1H), 2.86 (dtd, J=13.1, 7.7, 5.3 Hz, 1H), 2.72 (dtd, J=13.2, 7.5, 5.2 Hz, 1H), 2.20-2.08 (m, 3H), 1.93 (ddd, J=13.5, 8.1, 5.3 Hz, 1H), 1.76 (dt, J=14.5, 8.9 Hz, 1H), 1.68-1.59 (m, 3H), 1.50 (dt, J=23.3, 21.2, 9.8, 5.9 Hz, 4H); $^{13}$C NMR: δ 150.7, 148.9, 139.3, 138.3, 133.3, 130.8, 129.4, 129.3, 129.2, 128.5, 128.4, 114.1, 110.5, 109.8, 68.3, 57.0, 40.9, 40.3, 34.5, 34.2, 31.4, 24.8. 4-bromo-N-(2-{2-bromo-4-fluoro-10-methylidene-5H,5aH,6H,7H,8H,9H,10H,10aH-cyclohepta[b]indol-10a-yl}ethyl)benzene-1-sulfonamide (21a): TLC (hexanes:ethyl acetate, 3:1 v/v): $R_f$=0.40; colorless oil, 75%; $^1$H NMR: δ 7.63 (d, J=7.7 Hz, 4H), 6.98 (dd, J=9.6, 1.6 Hz, 1H), 6.74 (d, J=1.7 Hz, 1H), 5.08 (s, 1H), 5.02 (s, 1H), 4.98 (s, 1H), 3.75 (d, J=7.9 Hz, 1H), 2.86 (d, J=7.5 Hz, 1H), 2.68 (d, J=7.7 Hz, 1H), 2.18-2.10 (m, 3H), 1.96 (t, J=7.6 Hz, 2H), 1.79 (s, 1H), 1.64 (s, 3H), 1.44 (d, J=7.3 Hz, 1H). N-(2-{2-bromo-4-fluoro-10-methylidene-5H,5aH,6H,7H,8H,9H,10H,10aH-cyclohepta[b]indol-10a-yl}ethyl)-3,4-dichlorobenzene-1-sulfonamide (21b): TLC (hexanes:ethyl acetate, 3:1 v/v): $R_f$=0.40; colorless oil, 75%; $^1$H NMR: δ 7.86 (d, J=1.9 Hz, 1H), 7.58 (d, J=3.5 Hz, 1H), 6.99 (dd, J=9.7, 1.8 Hz, 1H), 6.76 (d, J=1.8 Hz, 1H), 5.10 (d, J=11.0 Hz, 2H), 5.04 (s, 1H), 3.76 (d, J=8.1 Hz, 1H), 3.67 (s, 1H), 2.88 (dq, J=13.5, 7.2 Hz, 1H), 2.68 (dq, J=13.3, 7.1 Hz, 1H), 2.20 (dd, J=14.4, 7.2 Hz, 1H), 2.15 (q, J=6.1 Hz, 3H), 1.98 (ddd, J=13.6, 8.8, 5.9 Hz, 2H), 1.81 (dt, J=15.5, 8.4 Hz, 2H), 1.64 (m, 2H), 1.48 (d, J=10.7 Hz, 2H). N-[3-(6-bromo-4-methylidene-2,3,4,4a,9,9a-hexahydro-1H-carbazol-4a-yl)propyl]-4-chlorobenzene-1-sulfonamide (23): TLC (hexanes: δ 7.80 (d, J=8.6 Hz, 2H), 7.50 (d, J=8.6 Hz, 2H), 7.15 (dd, J=8.3, 2.0 Hz, 1H), 7.05 (d, J=2.0 Hz, 1H), 6.55 (d, J=8.2 Hz, 1H), 4.90 (s, 1H), 4.59 (s, 1H), 4.43 (s, 1H), 3.63 (s, 1H), 2.97 (qd, J=6.5, 2.7 Hz, 2H), 2.15 (dq, J=12.8, 7.0, 5.7 Hz, 2H), 1.77 (ddd, J=15.4, 12.1, 8.4 Hz, 2H), 1.71-1.50 (m, 8H), 1.44 (ddd, J=12.6, 6.5, 4.1 Hz, 2H); $^{13}$C NMR: δ 149.1, 148.9, 138.5, 136.5, 132.2, 132.0, 131.9, 130.4, 129.4, 128.6, 128.5, 128.4, 127.1, 111.8, 111.6, 110.2, 65.2, 53.0, 43.8, 32.3, 32.2, 29.7, 28.0, 25.8, 21.8. N-(2-(6-Bromo-9-methyl-4-methylene-2,3,4,4a,9,9a-hexahydro-1H-carbazol-4a-yl)ethyl)-4-chlorobenzenesulfonamide (1a): TLC (hexanes:ethyl acetate, 15:1 v/v): $R_f$=0.20; colorless oil, 73%; $^1$H NMR (500 MHz, CDCl$_3$) δ 7.83-7.74 (m, 2H), 7.55-7.45 (m, 2H), 7.21 (dd, J=8.3, 2.0 Hz, 1H), 7.00 (d, J=2.0 Hz, 1H), 6.39 (d, J=8.3 Hz, 1H), 4.82 (s, 1H), 4.52 (s, 1H), 3.09-3.00 (m, 2H), 2.98-2.89 (m, 1H), 2.62 (s, 3H), 2.24-2.18 (m, 1H), 2.16-2.06 (m, 2H), 1.99 (ddd, J=14.2, 10.3, 5.6 Hz, 1H), 1.92-1.85 (m, 1H), 1.74-1.64 (m, 1H), 1.61-1.52 (m, 2H); MS (ESI): m/z: [M+H]$^+$ 459.0. N-{2-[6-bromo-9-(4-chlorobenzoyl)-4-methylidene-2,3,4,4a,9,9a-hexahydro-1H-carbazol-4a-yl]ethyl}-4-chlorobenzene-1-sulfonamide (1c): TLC (hexanes:ethyl acetate, 2:1 v/v): $R_f$=0.60; colorless oil, 92%; $^1$H NMR: δ 7.74 (d, J=8.6 Hz, 2H), 7.49 (d, J=8.6 Hz, 2H), 7.44 (q, J=8.2 Hz, 4H), 7.10 (d, J=2.0 Hz, 1H), 5.22 (s, 1H), 5.01 (s, 1H), 4.77-4.68 (m, 1H), 4.30 (brs, 1H), 3.11-3.04 (m, 1H), 2.99-2.87 (m, 1H), 2.29 (d, J=14.5 Hz, H), 2.04 (d, J=10.0 Hz, 1H), 1.97-1.88 (m, 2H), 1.54 (dt, J=13.5, 4.3 Hz, 1H); $^{13}$C NMR: δ 173.0, 144.9, 139.6, 139.4, 138.2, 137.0, 134.1, 131.2, 129.5, 129.2, 128.7, 128.5, 126.5, 117.2, 113.8, 67.4, 51.4, 39.7, 37.7, 32.7, 21.4; m/z: Calcd for C$_{28}$H$_{25}$BrCl$_2$KN$_2$O$_3$S [M+K]$^+$ 656.9778. Found 656.9780; IR: 2916, 2849, 1631, 1587, 1469, 1422, 1380, 1331, 1163, 1089, 1014, 829, 740 cm$^{-1}$. N-{2-[6-bromo-9-(4-chlorobenzenesulfonyl)-4-methylidene-2,3,4,4a,9,9a-hexahydro-1H-carbazol-4a-yl]ethyl}-4-chlorobenzene-1-sulfonamide (1b): TLC (hexanes:ethyl acetate, 2:1 v/v): $R_f$=0.60; colorless oil, 72%; $^1$H NMR: δ 7.82 (d, J=8.6 Hz, 2H), 7.74 (d, J=8.6 Hz, 2H), 7.57-7.45 (m, 5H), 7.38 (dd, J=8.6, 2.1 Hz, 1H), 6.99 (d, J=2.1 Hz, 1H), 5.13 (d, J=2.0 Hz, 1H), 4.86 (d, J=2.0 Hz, 1H), 4.11 (dd, J=7.9, 5.7 Hz, 1H), 3.98 (d, J=5.1 Hz, 1H), 2.83-2.77 (m, 1H), 2.74-2.64 (m, 1H), 2.29-2.24 (m, 1H), 2.05-1.98 (m, 1H), 1.96-1.89 (m, 1H), 1.69-1.61 (m, 2H), 1.21-1.15 (m, 1H); $^{13}$C NMR: δ 144.8, 140.1, 139.4, 139.2, 138.4, 138.2, 137.2, 131.9, 129.8, 129.5, 128.4, 128.3, 127.0, 117.0, 116.8, 113.7, 68.3, 52.1, 39.0, 38.3, 31.6, 29.7, 19.9; m/z: Calcd for $C_{27}H_{25}BrCl_2KN_2O_4S_2$ [M+K]$^+$ 692.9448. Found 692.9451; IR: 2292, 2920, 2850, 1638, 1475, 1360, 1338, 1166, 1093, 826, 756 cm$^{-1}$. benzyl 6-bromo-4a-[2-(4-chlorobenzenesulfonamido)ethyl]-4-methylidene-2,3,4,4a,9,9a-hexahydro-1H-carbazole-9-carboxylate (1d): TLC (hexanes:ethyl acetate, 3:1 v/v): $R_f$=0.40; colorless oil, 75%; $^1$H NMR: δ 7.68 (d, J=8.2 Hz, 2H), 7.49-7.41 (m, 7H), 7.40-7.31 (m, 2H), 7.02 (d, J=2.1 Hz, 1H), 5.30 (s, 2H), 5.18 (s, 1H), 4.99 (s, 1H), 4.34-4.15 (m, 2H), 2.97 (s, 1H), 2.78 (t, J=11.8 Hz, 1H), 2.33-2.21 (m, 2H), 2.06-1.91 (m, 4H), 1.86-1.76 (m, 1H), 1.65 (d, J=7.5 Hz, 1H). N-{2-[6-bromo-4-methylidene-9-(prop-2-en-1-yl)-2,3,4,4a,9,9a-hexahydro-1H-carbazol-4a-yl]ethyl}-4-chlorobenzene-1-sulfonamide (1e): TLC (hexanes:ethyl acetate, 3:1 v/v): $R_f$=0.40; colorless oil, 75%; $^1$H NMR: δ 7.78 (d, J=8.5 Hz, 2H), 7.51 (d, J=8.5 Hz, 2H), 7.18 (dd, J=8.3, 2.1 Hz, 1H), 6.97 (d, J=2.0 Hz, 1H), 6.39 (d, J=8.3 Hz, 1H), 5.78 (dddd, J=17.2, 10.2, 6.9, 4.7 Hz, 1H), 5.24 (dd, J=17.2, 1.7 Hz, 1H), 5.18 (dd, J=10.3, 1.5 Hz, 1H), 4.85 (d, J=1.6 Hz, 1H), 4.57 (s, 1H), 4.48 (t, J=6.2 Hz, 1H), 3.82 (ddt, J=16.2, 4.2, 1.7 Hz, 1H), 3.56-3.48 (m, 1H), 3.35 (t, J=4.2 Hz, 1H), 3.12-2.99 (m, 1H), 2.95 (dddd, J=15.9, 11.5, 8.2, 4.9 Hz, 1H), 2.17 (dqq, J=13.8, 9.8, 5.2 Hz, 3H), 2.10-2.03 (m, 2H), 2.03-1.94 (m, 1H), 1.83-1.76 (m, 1H), 1.73-1.64 (m, 1H), 1.55-1.49 (m, 1H). N-{2-[6-bromo-9-(2-{2-[2-(2-hydroxyethoxy)ethoxy]ethoxy}ethyl)-4-methylidene-2,3,4,4a,9,9a-hexahydro-1H-carbazol-4a-yl]ethyl}-4-chlorobenzene-1-sulfonamide (1f): TLC (hexanes:ethyl acetate, 3:1 v/v): $R_f$=0.40; colorless oil, 75%; $^1$H NMR: δ 7.76 (d, J=8.6 Hz, 2H), 7.49 (d, J=8.6 Hz, 2H), 7.15 (dd, J=8.3, 2.1 Hz, 1H), 6.91 (d, J=2.1 Hz, 1H), 6.30 (d, J=8.3 Hz, 1H), 5.62-5.54 (m, 1H), 4.92 (d, J=1.6 Hz, 1H), 4.70 (s, 1H), 3.72 (dd, J=5.1, 3.2 Hz, 2H), 3.67-3.51 (m, 17H), 3.35 (h, J=5.2 Hz, 2H), 3.20 (dt, J=15.0, 5.6 Hz, 1H), 3.08-2.98 (m, 1H), 2.93-2.81 (m, 1H), 2.26-2.14 (m, 2H), 2.12-2.04 (m, 2H), 2.03-1.89 (m, 3H), 1.71 (ddt, J=14.1, 9.2, 4.4 Hz, 1H), 1.65-1.51 (m, 4H); $^{13}$C NMR: δ 149.4, 148.4, 138.9, 138.7, 135.4, 130.6, 129.4, 129.3, 128.6, 126.4, 111.7, 108.5, 108.0, 72.5, 70.6, 70.4, 70.3, 70.3, 68.7, 68.5, 61.6, 51.8, 44.2, 39.9, 36.4, 32.5, 29.7, 24.9, 21.0. N-[2-(6-bromo-4-methylidene-2,3,4,4a,9,9a-hexahydro-1H-carbazol-4a-yl)ethyl]-4-chloro-N-methylbenzene-1-sulfonamide (1g): TLC (hexanes:ethyl acetate, 2:1 v/v): $R_f$=0.45; colorless oil, 89%; $^1$H NMR: δ 7.70 (d, J=8.5 Hz, 2H), 7.50 (d, J=8.5 Hz, 2H), 7.16 (dd, J=8.2, 2.0 Hz, 1H), 7.09 (s, 1H), 6.55 (d, J=8.2 Hz, 1H), 4.95 (s, 1H), 4.66 (s, 1H), 3.70 (t, J=4.5 Hz, 1H), 3.18 (ddd, J=13.6, 11.2, 5.4 Hz, 1H), 2.97 (ddd, J=13.6, 11.0, 5.1 Hz, 1H), 2.78 (s, 3H), 2.14-2.00 (m, 3H), 1.87-1.79 (m, 1H), 1.73-1.66 (m, 2H); $^{13}$C NMR: δ 149.4, 139.1, 135.9, 130.6, 129.5, 129.4, 129.1, 128.7, 126.7, 111.8, 110.0, 109.6, 61.7, 51.4, 47.4, 37.9, 35.2, 33.1, 32.8, 21.8; m/z: Calcd for $C_{22}H_{24}BrClKN_2O_2S$ [M+K]$^+$ 533.0062. Found 533.0068; IR: 3371, 2925, 2853, 2359, 1636, 1474, 1344, 1260, 1160, 1104, 1014, 804 cm$^{-1}$. 2-(6-Bromo-4-methylidene-2,3,4,4a,9,9a-hexahydro-1H-carbazol-4a-yl)-N-(4-chlorobenzenesulfonyl)-S-(4-chlorophenyl)ethane-1-sulfonamido (1h): TLC (hexanes:ethyl acetate, 2:1 v/v): $R_f$=0.75; colorless oil, 52%; $^1$H NMR: δ 7.94 (d, J=8.7 Hz, 4H), 7.55 (d, J=8.7 Hz, 4H), 7.25-7.12 (m, 2H), 6.57 (d, J=8.2 Hz, 1H), 4.97 (s, 1H), 4.71 (s, 1H), 3.83 (ddd, J=15.4, 12.5, 5.3 Hz, 1H), 3.68 (t, J=4.4 Hz, 1H), 3.51 (ddd, J=15.2, 12.3, 4.6 Hz, 1H), 2.33-2.12 (m, 4H), 1.89-1.79 (m, 1H), 1.75-1.67 (m, 3H); $^{13}$C NMR: δ 148.9, 148.1, 141.0, 138.0, 135.0, 130.8, 129.8, 127.7, 124.6, 112.3, 111.9, 110.2, 65.1, 52.1, 39.4, 35.5, 32.3, 20.0; m/z: Calcd for $C_{27}H_{25}BrCl2N_2O_4S2$ [M+H]$^+$ 654.9889. Found 654.9871; IR: 2922, 2851, 1736, 1655, 1476, 1377, 1167, 1080, 826, 756, 620 cm$^{-1}$. N-[2-(6-bromo-4-methylidene-2,3,4,4a,9,9a-hexahydro-1H-carbazol-4a-yl)ethyl]-4-chloro-N-(4-chlorobenzenesulfonyl)benzamide (1i): TLC (hexanes:ethyl acetate, 2:1 v/v): $R_f$=0.70; colorless oil, 92%; $^1$H NMR: δ 7.84 (d, J=8.6 Hz, 2H), 7.51 (d, J=8.6 Hz, 2H), 7.41 (s, 5H), 7.14 (dd, J=8.2, 2.0 Hz, 1H), 6.88 (d, J=2.0 Hz, 1H), 6.51 (d, J=8.2 Hz, 1H), 4.91 (s, 1H), 4.60 (s, 1H), 3.97-3.86 (m, 1H), 3.76-3.66 (m, 1H), 3.62 (t, J=4.6 Hz, 1H), 2.21-2.09 (m, 4H), 2.08-2.06 (t, J=4.6 Hz, 1H), 1.82-1.76 (m, 1H), 1.70-1.64 (m, 4H); $^{13}$C NMR: δ 170.2, 144.4, 140.8, 139.7, 138.4, 136.7, 133.0, 131.2, 129.6, 129.5, 129.5, 129.1, 129.0, 128.6, 126.5, 119.1, 117.1, 114.0, 67.5, 51.4, 44.3, 36.6, 32.8, 21.6; m/z: Calcd for $C_{28}H_{25}BrCl_2KN_2O_3S$ [M+K]$^+$ 656.9778. Found 656.9777; IR: 3374, 2921, 2851, 1637, 1465, 1376, 1261, 1165, 1091, 1013, 827, 758 cm$^{-1}$. benzyl N-[2-(6-bromo-4-methylidene-2,3,4,4a,9,9a-hexahydro-1H-carbazol-4a-yl)ethyl]-N-(4-chlorobenzenesulfonyl)carbamate (1j): TLC (hexanes:ethyl acetate, 3:1 v/v): $R_f$=0.40; colorless oil, 35%; $^1$H NMR: δ 7.76 (d, J=8.6 Hz, 2H), 7.40-7.33 (m, 7H), 7.25-7.21 (m, 1H), 7.17 (dd, J=8.2, 2.0 Hz, 1H), 6.56 (d, J=8.3 Hz, 1H), 5.14 (s, 1H), 5.11 (s, 2H), 4.94 (s, 1H), 4.70 (s, 1H), 4.01 (ddd, J=14.2, 11.8, 5.2 Hz, 1H), 3.85-3.79 (m, 1H), 3.76 (t, J=4.2 Hz, 1H), 2.24 (td, J=12.4, 5.0 Hz, 2H), 2.18 (t, J=6.2 Hz, 2H), 1.83-1.77 (m, 1H), 1.74-1.66 (m, 3H). N-[2-(6-bromo-4-methylidene-2,3,4,4a,9,9a-hexahydro-1H-carbazol-4a-yl)ethyl]-4-chloro-N-(prop-2-en-1-yl)benzene-1-sulfonamide (1k): TLC (hexanes:ethyl acetate, 3:1 v/v): $R_f$=0.40; colorless oil, 75%; $^1$H NMR: 7.73 (d, J=8.6 Hz, 2H), 7.49 (d, J=8.6 Hz, 2H), 7.18-7.13 (m, 1H), 7.12 (d, J=2.0 Hz, 1H), 6.54 (d, J=8.2 Hz, 1H), 5.67 (ddt, J=16.9, 10.2, 6.6 Hz, 1H), 5.28-5.17 (m, 2H), 4.89 (s, 1H), 4.58 (s, 1H), 3.81 (d, J=6.6 Hz, 2H), 3.66 (t, J=4.3 Hz, 1H), 3.20 (ddd, J=14.3, 12.2, 5.2 Hz, 1H), 3.00 (ddd, J=19.5, 11.1, 4.9 Hz, 1H), 2.37 (q, J=7.8, 7.0 Hz, 1H), 2.25-2.16 (m, 2H), 2.15-2.00 (m, 3H), 1.84-1.76 (m, 1H), 1.76-1.66 (m, 3H), 1.62 (d, J=16.8 Hz, 1H). benzyl 4a-(2-{N-[(benzyloxy)carbonyl]4-chlorobenzenesulfonamido}ethyl)-6-bromo-4-methylidene-2,3,4,4a,9,9a-hexahydro-1H-carbazole-9-carboxylate (1l): TLC (hexanes:ethyl acetate, 3:1 v/v): $R_f$=0.60; colorless oil, 24%; $^1$H NMR: δ 7.65 (d, J=8.3 Hz, 2H), 7.45 (d, J=7.3 Hz, 2H), 7.36 (dd, J=8.6, 6.3 Hz, 8H), 7.30 (s, 2H), 7.20-7.14 (m, 2H), 7.10 (d, J=2.1 Hz, 1H), 5.39-5.35 (m, 4H), 5.30 (s, 1H), 5.19 (d, J=7.4 Hz, 2H), 5.03 (s, 2H), 4.60-4.43 (m, 1H), 4.01-3.90 (m, 1H), 3.71 (t, J=13.2 Hz, 1H), 2.35-2.29 (m, 1H), 2.24 (t, J=7.7 Hz, 1H), 2.05-1.94 (m, 4H), 1.65 (d, J=7.6 Hz, 2H).

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. An indoline alkaloid compound that is capable of re-sensitizing the susceptibility of methicillin-resistant *S. aureus* to a β-lactam antibiotic, wherein said indoline alkaloid compound is of the formula:

A

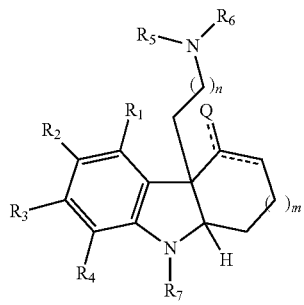

wherein
  each of m and n is independently 1 or 2;
  one of the dotted lines is a double bond, provided Q is $CH_2$ when the double bond is exocyclic, and Q is H when the double bond is endocyclic;
  each of $R_1$, $R_3$ and $R_4$ is independently hydrogen or halide, or $R_3$ and $R_4$ together with the carbon atoms to which they are attached form phenyl;
  $R_2$ is hydrogen, halide, alkyl, or alkoxide;
  $R_5$ is hydrogen, alkyl, —S(O)$_2$Ar$^1$ or —COAr$^1$;
  $R_6$ is hydrogen, —S(O)$_2$Ar$^2$, —COAr$^2$ or —COR$^8$;
  $R_7$ is hydrogen, alkyl, —S(O)$_2$Ar$^3$ or —COAr$^3$;
  $R_8$ is alkyl or haloalkyl;
  each of Ar$^1$ and Ar$^3$ is independently optionally substituted aryl; and
  Ar$^2$ is optionally substituted aryl or optionally substituted heteroaryl provided when $R_6$ is —S(O)$_2$-Ph-p-Cl and $R_2$ is Br, at least one of $R_1$, $R_3$, $R_4$, $R_5$ and $R_7$ is not hydrogen.

2. The compound of claim 1, wherein $R_1$ is hydrogen or Br; $R_2$ is Br, Cl, F, alkyl, or alkoxy; $R_3$ is hydrogen or Br; $R_4$ is hydrogen, Br, Cl or F; or $R_3$ and $R_4$ together with the carbon atoms to which they are attached form phenyl.

3. The compound of claim 1, wherein $R^5$ is hydrogen or $R^7$ is hydrogen.

4. An antibiotic composition comprising an indoline alkaloid compound of claim 1.

5. The antibiotic composition of claim 4, further comprising a β-lactam antibiotic.

6. The antibiotic composition of claim 5, further comprising a β-lactamase inhibitor or other resistance-modifying agent or a combination thereof.

7. A method for treating bacterial infection in a subject comprising administering to the subject in need of such a treatment a therapeutically effective amount of a β-lactam antibiotic and an indoline alkaloid compound of claim 1.

8. A method for treating MRSA infection in a subject comprising administering to the subject having a MRSA infection a therapeutically effective amount of a β-lactam and a compound of claim 1.

9. The method of claim 8, wherein the β-lactam comprises amoxicillin, clavulanic acid, cefazolin, meropenem, or a combination thereof.

* * * * *